US008852593B2

(12) United States Patent
Baurin et al.

(10) Patent No.: US 8,852,593 B2
(45) Date of Patent: Oct. 7, 2014

(54) ANTAGONIST ANTIBODIES AND THEIR FAB FRAGMENTS AGAINST GPVI AND USES THEREOF

(75) Inventors: Nicolas Baurin, Arpagjon (FR); Francis Blanche, Paris (FR); Beatrice Cameron, Paris (FR); Carsten Corvey, Frankfurt (DE); Tarik Dabdoubi, Le Coudray Montceaux (FR); Christian Engel, Frankfurt (DE); Peter Florian, Frankfurt (DE); Ingo Focken, Hochheim (DE); Katja Kroll, Frankfurt (DE); Jochen Kruip, Erzhausen (DE); Christian Lange, Frankfurt (DE); Thomas Langer, Frankfurt (DE); Martin Lorenz, Frankfurt (DE); Vincent Mikol, Charenton-le-Pont (FR); Ercole Rao, Moerfelden-Waldorf (DE); Peter Wonerow, Wildau (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/515,650

(22) PCT Filed: Dec. 17, 2010

(86) PCT No.: PCT/IB2010/055917
§ 371 (c)(1),
(2), (4) Date: Jun. 13, 2012

(87) PCT Pub. No.: WO2011/073954
PCT Pub. Date: Jun. 23, 2011

(65) Prior Publication Data
US 2012/0244152 A1    Sep. 27, 2012

(30) Foreign Application Priority Data

Dec. 18, 2009   (EP) .................................. 09306283.4
Jun. 21, 2010   (EP) .................................. 10305660.2
Jul. 1, 2010    (EP) .................................. 10305721.2

(51) Int. Cl.
*A61K 39/395* (2006.01)
*C07K 16/28* (2006.01)
*A61K 39/00* (2006.01)

(52) U.S. Cl.
CPC ....... *C07K 16/2803* (2013.01); *C07K 2317/565* (2013.01); *C07K 2317/24* (2013.01); *C07K 2317/33* (2013.01); *A61K 2039/505* (2013.01); *C07K 2317/92* (2013.01); *C07K 2317/41* (2013.01); *C07K 2317/34* (2013.01); *C07K 2317/76* (2013.01); *C07K 2317/55* (2013.01)
USPC .................. 424/139.1; 424/133.1; 424/143.1; 424/153.1; 530/387.3; 530/388.22; 530/388.7; 514/13.8

(58) Field of Classification Search
None
See application file for complete search history.

(56) References Cited

U.S. PATENT DOCUMENTS

| 6,833,131 | B1* | 12/2004 | Smith ........................ 424/130.1 |
| 2002/0141992 | A1* | 10/2002 | Nieswandt ................. 424/143.1 |
| 2003/0049701 | A1* | 3/2003 | Muraca ........................ 435/7.23 |
| 2006/0088531 | A1* | 4/2006 | Smethurst et al. ......... 424/145.1 |
| 2006/0224331 | A1* | 10/2006 | Watson Michnick et al. .. 702/20 |
| 2009/0041783 | A1 | 2/2009 | Takayama |
| 2010/0119511 | A1* | 5/2010 | Wang et al. ................ 424/134.1 |

FOREIGN PATENT DOCUMENTS

| EP | 1228768 A1 | 7/2002 |
| EP | 1369128 A1 | 12/2003 |
| EP | 1538165 A1 | 6/2005 |
| EP | 1647596 A1 | 4/2006 |
| EP | 1224942 A1 | 7/2007 |
| EP | 1876240 A1 | 1/2008 |
| EP | 1916259 A1 | 4/2008 |
| EP | 2000802 A1 | 12/2008 |
| WO | WO0100810 A1 | 1/2001 |
| WO | WO 01/32688 A1 * | 5/2001 |
| WO | WO0280968 A1 | 1/2002 |
| WO | WO03054020 A2 | 7/2003 |
| WO | WO2005090407 A1 | 9/2005 |
| WO | WO2005111083 A2 | 11/2005 |
| WO | WO2006061650 A2 | 6/2006 |
| WO | WO2006131512 A2 | 12/2006 |
| WO | WO2007091719 A1 | 8/2007 |
| WO | WO2009058326 A1 | 5/2009 |

OTHER PUBLICATIONS

Nieswandt et al., J Exp Med. Feb. 19, 2001;193(4):459-69.*
Kwong et al., Curr Protoc Protein Sci. Feb. 2009;Chapter 6:Unit 6.10. doi: 10.1002/0471140864.ps0610s55.*
O'Brien et al., Protein Expr Purif. Feb. 2002;24(1):43-50.*
Schulte et al., J Biol Chem. Jan. 5, 2001;276(1):364-8.*

(Continued)

*Primary Examiner* — Michael Szperka
(74) *Attorney, Agent, or Firm* — Lathrop & Gage LLP; James H. Velema, Esq.

(57) ABSTRACT

The present invention discloses novel antibodies that specifically bind to the human platelet membrane protein Glycoprotein VI (GPVI) and their monovalent fragments or derivatives. The antibodies of the invention are antibodies from hybridoma clone 390 and fragment antibodies thereof able to induce a GPVI depletion phenotype. These antibodies and Fab fragments are able to block collagen binding and thus preventing platelet activation by collagen. The invention also relates to hybridoma clones and expression plasmids for the production of disclosed antibodies and Fab fragments. The present invention further refers to the uses of monovalent antibody fragments to manufacture research, diagnostic and immunotherapeutic agents for the treatment of thrombosis and other vascular diseases. The invention also concerns a Fab bearing a molecule at the C-terminal extremity, as well as method for prevention of recognition of Fab by antibodies using such modified Fab. The invention concerns a method for prevention of platelet activation when an anti-GP VI Fab is used.

8 Claims, 23 Drawing Sheets

(56) References Cited

OTHER PUBLICATIONS

Schulte et al., Blood. May 15, 2003;101(10):3948-52. Epub Jan. 16, 2003.*

Tiwari, et al.; Generation and Characterization of High Affinity Humanized Fab Against Hepatitis B Surface Antigen; Molecular Biotechnology, vol. 43, No. 1, Sep. 1, 2009, pp. 29-40.

Nieswandt, et al.; Long-term antithrombotic protection by in vivo depletion of platelet glycoprotein VI in mice; J. of Experimental Medicine, vol. 193, No. 4, Feb. 19, 2001, pp. 459-469.

Schulte, et al.; Two-phase antithrombotic protection after anti-glycoprotein VI treatment in mice; Arteriosclerosis, Thrombosis, and Vascular Biology,; Highwire Press, Philadelphia, PA, vol. 26, No. 7, Jul. 1, 2006, pp. 1640-1647.

International Preliminary Report on Patentability, PCT/IB2010/055917, dated Jun. 19, 2012.

Pluckthun: Strategies for the Expression of Antibody Fragments in *Escherichia coli*; Methods; Apr. 1991, vol. 2, No. 2, pp. 88-96.

* cited by examiner

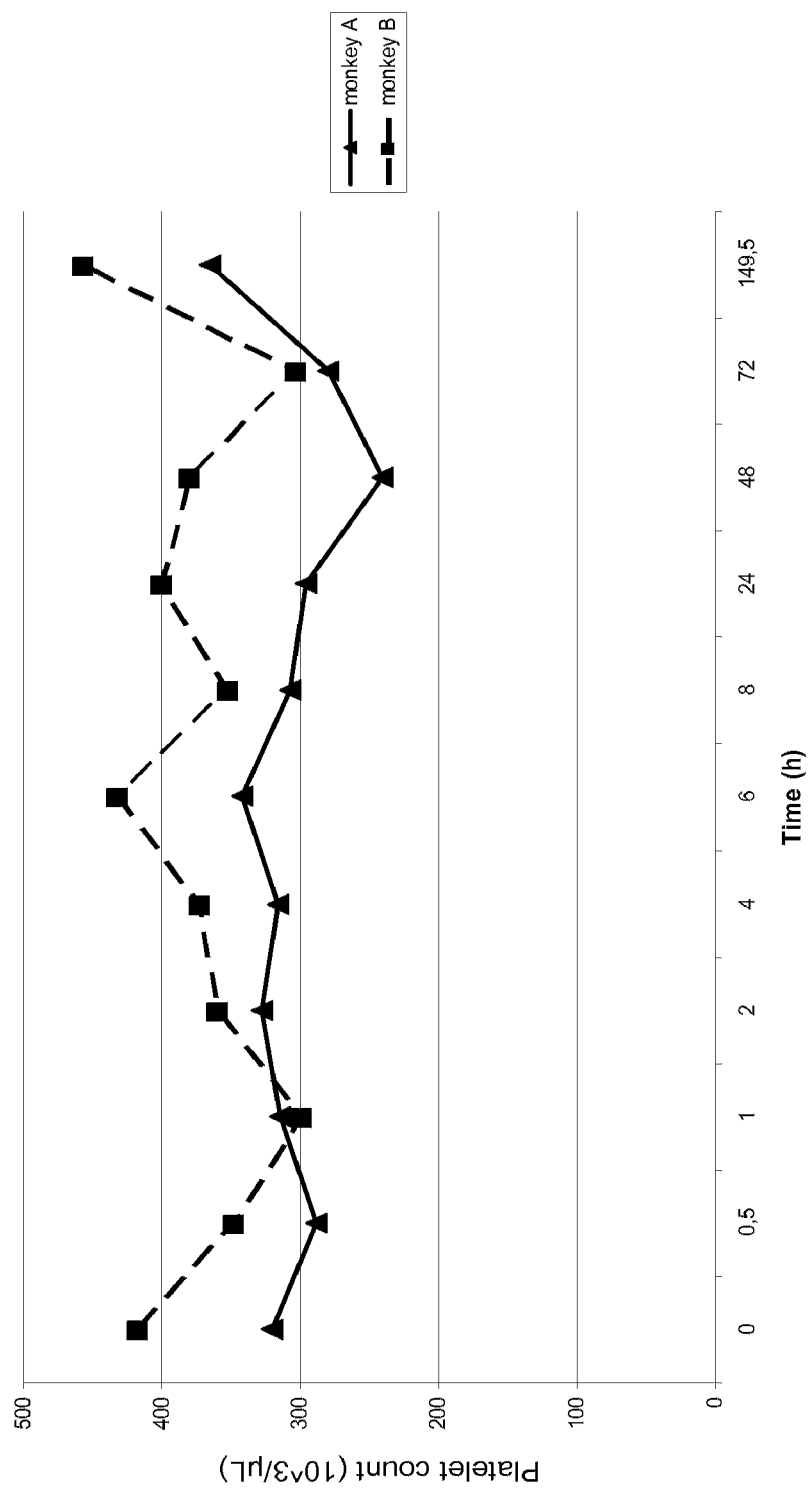

FIGURE 16

```
  1  QSGPLPKPSL QALPSSLVPL EKPVTLRCQG PPGVDLYRLE KLSSSRYQDQ
 51  AVLFIPAMKR SLAGRYRCSY QNGSLWSLPS DQLELVATGV FAKPSLSAQP
101  GPAVSSGGDV TLQCQTRYGF DQFALYKEGD PAPYKNPERW YRASFPIITV
151  TAAHSGTYRC YSFSSRDPYL WSAPSDPLEL VVTGTSVTPS RLPTEPPSSV
201  AEFSEATAEL TVSFTNKVFT TETSRSITTS PKESDSPAGP ARQYTKGNL
251  VRICLGAVIL IILAGFLAED WHSRRKRLRH RGRAVQRPLP PLPPLPQTRK
301  SHGGQDGGRQ DVHSRGLCS
```

ANTAGONIST ANTIBODIES AND THEIR FAB FRAGMENTS AGAINST GPVI AND USES THEREOF

FIELD OF THE INVENTION

The present invention discloses novel antibodies that specifically bind to the human platelet membrane protein Glycoprotein VI (GPVI) and their monovalent fragments or derivatives. The antibodies of the invention are antibodies from hybridoma clone 390 and antibodies that bind to an epitope which is similar to the conformational epitope recognized by the antibody from hybridoma clone 390. These antibodies and Fab fragments are able to block collagen binding and thus preventing platelet activation by collagen. The invention also relates to hybridoma clones and expression plasmids for the production of disclosed antibodies and Fab fragments. The present invention further refers to the uses of monovalent antibody fragments to manufacture research, diagnostic and immunotherapeutic agents for the treatment of thrombosis and other vascular diseases. In another aspect, the invention concerns a method to prevent receptor activation through patient specific anti-Fab antibodies induced receptor clustering.

BACKGROUND OF THE INVENTION

Platelet function is of fundamental importance in the development of arterial thrombosis and cardiovascular diseases. Nowadays it is a matter of course that patients suffering from cardiovascular diseases are treated with antiplatelet drugs. Despite the availability of various clinically successful antiplatelet therapies, there is still a large unmet medical need for new treatments. This deficiency is mainly caused by the limited efficacy of the currently available drugs, particularly in regard to the drugs efficacy—safety (bleeding) correlation. Interfering with early events of platelet activation and adhesion, a mechanism not targeted by drugs currently in use, would be an attractive approach for the improvement of the efficacy—safety margin. The collagen receptor glycoprotein (GPVI) is of central importance in these early events of platelet activation, and therefore a major target for the interference with this mechanism (Nieswandt B and Watson S P, Blood. 2003 Jul. 15; 102(2):449-61). The antiplatelet and antithrombotic effects of GPVI have been described in several in vitro and in vivo systems, using platelets from mice and men. Platelets deficient in GPVI are rendered unresponsive to collagen, one of the most important thrombogenic components of the subendothelial matrix (Lockyer S. et al, Thromb Res. 2006; 118(3):371-80). Moreover, mouse studies have shown that GPVI deficiency causes an effective inhibition of arterial thrombus formation at the damaged vessel wall without increasing the susceptibility to spontaneous bleeding. All these data suggest that GPVI represents an effective and safe target for the treatment of arterial thrombosis. The central role of GPVI in the initiation of thrombus formation indicates that inhibition of this receptor may be beneficial in syndromes of arterial thrombosis. This makes the use of biotherapeutic proteins such as antibodies a clinically meaningful strategy for the inhibition of GPVI. All the more since the interaction of GPVI and its ligand collagen seems to involve an expanded protein surface, a successful interference with this protein-protein interaction is more likely with inhibitory GPVI-binding proteins as compared to other strategies. An in vivo proof of concept for the inhibition of GPVI function by antibodies and Fab fragments has been shown in several animal models.

There is still a need for clinically effective inhibitors of GPVI activity.

GPVI is a major collagen receptor expressed exclusively on platelets and megacaryocytes. Binding to collagen induces receptor clustering and subsequent platelet activation. This is one of the initial events in thrombus formation. Current antiplatelet drugs interfere with thrombus formation through targeting late events in this process. A serious side effect of these drugs is prolonged bleeding which limits their use. There are several lines of evidence that targeting early events in thrombus formation (such as GPVI) can be highly antithrombotic without a major impact on bleeding liability. The interaction between collagen and GPVI can be successfully inhibited by neutralizing monoclonal antibodies (mAb). However as mAb's are bivalent molecules, they can induce GPVI-receptor clustering and therefore platelet activation. To circumvent this, monovalent antibody fragments such as Fab fragments have been developed.

Unfortunately, in depth safety profiling of these monovalent anti-GPVI Fab fragments reveals a potential to still induce platelet activation in a patient specific manner. To offer a safe therapeutic for the treatment of ischemic events, this activatory potential of the developed Fab molecules had to be abolished. Until now, this problem has not been resolved.

SUMMARY OF THE INVENTION

In a first aspect, this invention provides a novel monoclonal antibody (from clone 390) which specifically binds to human GPVI, as well as to primate GPVI.

In another aspect, the invention concerns recombinant Fab fragments derived from the variable domain sequences of anti-GPVI mAb from clone 390. These anti-GPVI antibody and Fab fragments recognize a specific conformational epitope in D1 and D2 domains of the human GPVI protein.

Both the anti-GPVI mAb and the Fab fragments are able to inhibit collagen binding to GPVI. The anti-GPVI Fab fragments have been humanized and engineered with the aim to improve their affinity to human GPVI. The biophysical characteristics of the humanized variants are described.

In addition to the inhibition of collagen, the anti-GPVI Fab fragments are able to inhibit platelet aggregation induced by collagen both in human platelet rich plasma and in human whole blood. These Fab Fragments are also able to inhibit the thrombus formation under flow on a collagen coated surface.

Thus, inhibition of GPVI by antibodies in humans appears as an attractive antithrombotic strategy.

Surprisingly, the anti-GPVI Fab of the invention induces a GPVI depletion phenotype. Thus, anti-GP VI Fab fragments able to induce GPVI depletion phenotype constitute another object of the invention.

The invention also provides a method for prevention of recognition of Fab fragments by pre-existing antibodies consisting in masking the C-terminal extremity of the Fab by addition of a molecule. The invention also provides a method for prevention of recognition of Fab fragments by new antibodies directed toward Fab C-terminal extremity consisting in masking the C-terminal extremity of the Fab by addition of a molecule.

The invention also provides a method for prevention of platelet activation when an anti-GPVI Fab is used, where the C-terminal extremity of the Fab is masked by addition of a molecule.

Another object of the invention is a Fab fragment bearing a molecule at the C-terminal extremity.

DNA and protein sequences as well as vectors for expression of the anti-GPVI and Fab fragments of the invention are also provided.

The antithrombotic agents of the invention may be used for the treatment of thrombotic or vascular diseases.

The invention also provides an antithrombotic composition comprising a pharmaceutically effective amount of a GPVI specific monoclonal antibody fragment of the invention with appropriate excipients.

In another aspect of the invention, the antibodies can be used for diagnosis of patients at risk requiring anti-thrombotic treatment. The invention also encompasses a kit for diagnosis including anti-GPVI antibodies or fragments thereof.

The invention also provides a method for the preparation of GPVI antibody, antibody fragments and masked antibody Fab fragments of the invention.

DETAILED DESCRIPTION OF THE INVENTION

In a first aspect, this invention provides a novel monoclonal antibody and fragments thereof which specifically binds to human GPVI, in particular the anti-GPVI mAb from hybridoma clone 390. The antibodies of the present invention antagonize, totally or partially, the activity of GPVI.

In a second aspect of the invention, the inventors have demonstrated that the addition of a peptide at the C-terminal extremity of the heavy chain (HC) of a Fab has a masking effect that avoids recognition of Fab molecules by preexisting anti-Fab antibodies in some patients and therefore prevents platelet activation and associated side effects.

As used herein, "monoclonal antibody from hybridoma clone 390" or "monoclonal antibody from clone 390" refers to an antibody defined by SEQ ID NO.6 and SEQ ID NO.8 as well as its derivatives including humanized antibodies, Fab fragments and humanized Fab fragments or any improved version of these molecules especially as described in the present application.

The term "antibody" is used herein in the broadest sense and specifically covers monoclonal antibodies (including full length monoclonal antibodies) of any isotype such as IgG, IgM, IgA, IgD and IgE, polyclonal antibodies, multispecific antibodies, chimeric antibodies, and antigen binding fragments. An antibody reactive with a specific antigen can be generated by recombinant methods such as selection of libraries of recombinant antibodies in phage or similar vectors, or by immunizing an animal with the antigen or an antigen-encoding nucleic acid.

A typical IgG antibody is comprised of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are usually referred to as CDR1, CDR2, and CDR3, numbered sequentially from the N-terminus. The more highly conserved portions of the variable regions are called the "framework regions".

In a particular embodiment, the antibodies and fragments thereof of the invention, including the antibody Fab fragment, comprise the 6 CDR defined by SEQ ID NO:18, SEQ ID NO:19, SEQ ID NO:20, SEQ ID NO:21, SEQ ID NO:22 and SEQ ID NO:23.

In another embodiment, the antibodies and fragments thereof of the invention, including the antibody Fab fragment, comprise the 6 CDR defined by SEQ ID NO:18, SEQ ID NO:19, SEQ ID NO:38, SEQ ID NO:21, SEQ ID NO:39 and SEQ ID NO:23. In another particular aspect, the antibody Fab fragment of the invention comprises:

(a) complementarity determining regions (CDRs) of a heavy chain variable region (HCVR) having amino acid sequences defined by SEQ ID NO: 18, SEQ ID NO: 19, and SEQ ID NO: 20 (or SEQ ID NO:38); and (b) complementarity determining regions (CDRs) of a light chain variable region (LCVR) having amino acid sequences defined by SEQ ID NO: 21, SEQ ID NO: 22 (or SEQ ID NO:39), and SEQ ID NO: 23; and wherein at least 2 amino acid residues of each CDR can be changed to another amino acid residue without directly disrupting a contact with a GPVI epitope residue.

As used herein, "directly disrupting a contact with the GPVI epitope residue" refers to changing an antibody amino acid residue that is in contact with a GPVI epitope residue and described in the crystal structure of the examples provided herein.

As used herein, "VH" refers to the variable region of an immunoglobulin heavy chain of an antibody, including the heavy chain of an Fv, scFv, dsFv, Fab, Fab' or F(ab')2 fragment. Reference to "VL" refers to the variable region of the immunoglobulin light chain of an antibody, including the light chain of an Fv, scFv, dsFv, Fab, Fab' or F(ab')2 fragment.

A "polyclonal antibody" is an antibody which was produced among or in the presence of one or more other, non-identical antibodies. In general, polyclonal antibodies are produced from a B-lymphocyte in the presence of several other B-lymphocytes producing non-identical antibodies. Usually, polyclonal antibodies are obtained directly from an immunized animal.

A "monoclonal antibody", as used herein, is an antibody obtained from a population of substantially homogeneous antibodies, i.e. the antibodies forming this population are essentially identical except for possible naturally occurring mutations which might be present in minor amounts. These antibodies are directed against a single epitope and are therefore highly specific.

As used herein, the terms "antigen-binding portion" of an antibody, "antigen-binding fragment" of an antibody, and the like, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Non-limiting examples of antigen-binding fragments include: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR)). Other engineered molecules, such as diabodies, triabodies, tetrabodies and minibodies, are also encompassed within the expression "antigen-binding fragment," as used herein.

As used herein, the term "Fab fragment" corresponds to the light chain (LC) plus part of the heavy chain (HC) of the antibody. Fab molecules are produced either by proteolytic cleavage of IgG molecules or made through expression of recombinant molecules. Usually parts of the constant domain of the heavy chain (Fc part) are removed.

As used herein, the term "masked Fab fragment" or "masked Fab" corresponds to a Fab fragment containing the light chain (LC) plus part of the heavy chain (HC) of the antibody and where the C-terminus of the HC has been extended by a peptide to mask recognition of the Fab by preexisting antibodies in a patient.

The antibodies of the invention have been obtained by the generation of hybridoma through mouse immunization technique using a human recombinant GPVI protein containing only extracellular D1 and D2 domains. The sequences of the protein used for immunization correspond to SEQ ID NO.3 and SEQ ID NO.4.

The obtained mAbs have been selected first for their ability to recognize the human GPVI protein, but also for their capability to block the binding of collagen to the human GPVI protein and to bind the GPVI protein with a high affinity.

The antibodies show cross-reactivity to primate GPVI (as shown in FIG. 2) whereas no cross-reactivity exists against murine, rat, dog, swine or rabbit GPVI.

The selected mAb is able to bind to the human GPVI protein with a pM affinity (as shown in Table 1) and to block collagen binding to the human GPVI protein with IC50 values of less than 10 μg/mL (as shown in FIG. 1A). This antibody is also able to block collagen binding to non-human primate GPVI (as shown in FIG. 1B).

In another aspect, the invention concerns recombinant Fab fragments derived from the variable domain sequences of anti-GPVI mAb from clone 390. Fab fragments can be prepared by any method know in the art. For example proteolytic Fab fragments can be obtained by Ficin cleavage or recombinant Fab fragments can be prepared by cloning the required sequences into an expression vector (for example as described in Example 3B). Like the anti-GPVI mAb, the Fab fragments are able to inhibit collagen binding to GPVI.

The Fab fragments have been co-crystallized with GPVI and analyzed by X-ray crystallography to determine the epitope recognized by the Fab on the GPVI protein. This analysis allowed defining a conformational epitope involving both D1 and D2 domains in the extracellular domain of the human GPVI. The numbering system used in the eptiope corresponds to GPVI with the 20 residue signal sequence removed and as shown in FIG. 16 and SEQ ID NO:32.

In one aspect of the invention, an isolated antibody or antigen binding fragment that specifically binds a conformational epitope of human GPVI and contacts human GPVI residues comprising Ser 43, Arg 67 and Asp 81. In another aspect of the invention, the antibody or antigen binding fragment makes additional contacts with two or more GPVI residues selected from the group consisting of Pro4, Lys7, Glu40, Lys41, Leu42, Ser44, Ser45, Arg46, Arg65, Trp76, Leu78, Pro79, Ser80, Gln82, Ser165, and Arg166. In another aspect of the invention, the antibody or antigen binding fragment makes additional contacts with three or more, four or more, five or more, six or more, seven or more, eight or more, nine or more, ten or more, eleven or more, twelve or more, thirteen or more, fourteen or more, fifteen or more GPVI residues selected from the group consisting of Pro4, Lys7, Glu40, Lys41, Leu42, Ser44, Ser45, Arg46, Arg65, Trp76, Leu78, Pro79, Ser80, Gln82, Ser165, and Arg166.

As used herein, "contacting residues" are defined as residues with a distance of less than 4.5 A to GPVI antigen residues or the reverse and as measured in a crystal structure between an antibody to GPVI or antigen binding fragment of the antibody and a GPVI antigen using a software program such as NCONT of the CCP4 Software package or an equivalent software program.

In one embodiment, the antibody Fab fragment binds a conformational epitope of human GPVI and contacts human GPVI residues comprising Ser 43, Arg 67 and Asp 81.

In another embodiment, the antibody Fab fragment binds a conformational epitope of human GPVI and contacts human GPVI residues comprising:
Pro4, Lys7, Glu40, Lys41, Leu42, Ser43, Ser44, Ser45, Arg46, Arg65, Arg67, Trp76, Leu78, Pro79, Ser80, Asp81, Gln82, Ser165, Arg166

The mAb of the invention recognize the same conformational epitope since the Fab fragments contain the variable domain sequences of anti-GPVI mAb from clone 390.

Thus, in another aspect, the invention provides an anti-GPVI antibody including Fab fragment, which recognizes a conformational epitope comprised in the extracellular D1 and D2 domains of the human GPVI protein.

Thus in another aspect, the invention provides a monoclonal anti-GPVI antibody which recognizes a conformational epitope comprising the following amino acids:
Glu40, Lys41, Leu42, Ser43, Ser44, Ser45, Arg46.

In another aspect, the invention provides an anti-GPVI antibody which recognizes a conformational epitope comprising the following amino acids:
Trp76, Leu78, Pro79, Ser80, Asp81, Gln82.

In another embodiment, the anti-GPVI antibody recognizes a conformational epitope comprising the following amino acids:
Glu40, Lys41, Leu42, Ser43, Ser44, Ser45, Arg46, Trp76, Leu78, Pro79, Ser80, Asp81, Gln82.

In another embodiment, the anti-GPVI antibody recognizes a conformational epitope, comprising the following amino acids:
Pro4, Lys7, Glu40, Lys41, Leu42, Ser43, Ser44, Ser45, Arg46, Arg65, Arg67, Trp76, Leu78, Pro79, Ser80, Asp81, Gln82, Ser165, Arg166.

In another embodiment, the anti-GPVI antibody recognizes a conformational epitope consisting in the following amino acids:
Pro4, Lys7, Glu40, Lys41, Leu42, Ser43, Ser44, Ser45, Arg46, Arg65, Arg67, Trp76, Leu78, Pro79, Ser80, Asp81, Gln82, Ser165, Arg166.

In a particular embodiment, the antibody Fab fragment of the invention involves mainly D1 domain of the human GPVI.

The antibody of the present invention can be defined as a monoclonal anti-GPVI antibody which (i) competitively inhibits the binding of an antibody comprising a HC of SEQ ID NO.6 and a LC of SEQ ID NO.8 to human GPVI and (ii) binds to an epitope similar to the conformational epitope recognized by antibody comprising a HC of SEQ ID NO.6 and a LC of SEQ ID NO.8, or a part of this conformational epitope, with an affinity of at least 10 nM (KD≤$10^{-8}$ M) as determined by a biophysical methods as for example Surface Plasmon Resonance (Biacore as described in Karlsson R, Larsson A. (2004), *J. Mol. Biol.* 248, 389-415).

As used herein, the term "$K_D$" refers to the dissociation constant of a particular antibody/antigen interaction.

The $K_D$ reflecting the interaction between the human GPVI protein and the antibody and Fab of the invention is comprised in the [$10^{-7}$; $10^{-10}$] interval. An antibody specific for human GPVI present a $K_D$=$10^{-7}$ M, preferably a $K_D$=$10^{-8}$ M, more preferably a $K_D$=$10^{-9}$ M. The antibody with the highest affinity may have a $K_D$=$10^{-10}$ M or below, for example $10^{-11}$ M or $10^{-12}$ M. The term "specifically binds," or the like, means that an antibody or antigen-binding fragment thereof forms a complex with a GPVI antigen that is relatively stable under physiologic conditions. Specific binding can be characterized by a dissociation constant of $1\times10^{-6}$ M or less. Methods for determining whether two molecules specifically bind are well known in the art and include, for example, equilibrium dialysis, surface plasmon resonance as in Examples 2 and 3, and the like. For example, an antibody that "specifically binds" human GPVI, as used in the context of the present invention, includes antibodies that bind human GPVI or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, such as measured in a surface plasmon resonance assay.

An "epitope" is the site on the antigen to which an antibody binds. If the antigen is a polymer, such as a protein or polysaccharide, the epitope can be formed by contiguous residues or by non-contiguous residues brought into close proximity by the folding of an antigenic polymer. In proteins, epitopes formed by contiguous amino acids are typically retained on exposure to denaturing solvents and are known as "linear epitopes", whereas epitopes formed by non-contiguous amino acids are typically lost under said exposure and are known as "conformational epitopes".

As used herein, the term "similar epitope" concern a set of amino acids located in the same region as the amino acids described by crystallography analysis as being involved physically in the interaction between antibodies derived from clone 390 and the extracellular domain of the human GPVI protein. A similar epitope can include several differences, for example up to five amino acids differences in the vicinity of the epitope of reference. A similar epitope can also present one or more modifications in the amino acids identified as forming the epitope, i.e. the amino acids interacting with the GPVI protein. One or more amino acid identified as part of the epitope of reference may be absent, and one or more additional amino acid residues may be present to form the similar epitope. For example, up to five amino acids may be changed without affecting the characteristics of the antibody compared to antibody from hybridoma clone 390. Thus, the region wherein the epitope is located for one specific antibody encompasses some potentially additional interacting amino acids. In this view, a similar epitope can be defined as a region for competitive binding with the antibody of reference". When a neutralizing antibody binds to such region, one or more cellular signalling pathway(s) of the receptor is/are inhibited leading to a specific impairment of one or more biological function(s) of the targeted receptor or more generally effective protein.

A "neutralizing" or "blocking" antibody, as used herein, is intended to refer to an antibody whose binding to GPVI: (i) interferes with the interaction between GPVI and collagen, (ii) and/or (iv) results in inhibition of at least one biological function of GPVI. The inhibition caused by a GPVI neutralizing or blocking antibody needs not to be complete as long as it is detectable using an appropriate assay. Exemplary assays for detecting GPVI inhibition are described herein The existence of topographic regions in proteins linked to specific biological activities is for example illustrated in U.S. Pat. No. 6,448,380.

Antibodies recognizing a similar epitope as antibodies derived from clone 390 can be selected by a competitive ELISA assay using GPVI-Fc fusion protein as capturing antigen. Plates coated with GPVI-Fc fusion protein are incubated with hybridoma supernatants or antibody or antigen binding fragments derived from clone 390. A lack of binding of different anti-GPVI antibodies (labelled by any standard technique) to epitope blocked GPVI indicates the recognition of a similar epitope. An equivalent selection strategy can be pursued by competitive Biacore analysis in which GPVI is immobilized and the antibody (fragments) derived from clone 390 is used to block the epitope. Other GPVI binding antibodies candidate are now analysed for binding to epitope blocked GPVI. Thus antibodies that recognize a similar epitope as epitope recognized by the antibody of the invention can be selected and further characterized by analysis of co-crystal structures using X-ray analysis.

The invention also concerns a humanized and engineered anti-GPVI antibody and fragment thereof.

In the context of the invention, the anti-GPVI Fab fragments have been humanized using a method previously described in WO2009/032661, but any humanization method known in the art can be used.

Based on the analysis of the crystallographic complex of the Fab with the GPVI, several mutations have been introduced both for humanization and with the aim to improve the affinity of the Fab to the human GPVI.

As a result, 3 variants for the LC and 5 variants for the HC have been generated. These Fab variants are summarized in Table 6 and in Table 7, respectively for LC (VL) and HC (VH).

Among all possible combinations, the invention concerns in particular the following combinations:

VL1 with VH1 which correspond to SEQ ID NO.15 and SEQ ID NO.10 respectively
VL1 with VH2 which correspond to SEQ ID NO.15 and SEQ ID NO.11 respectively
VL1 with VH3 which correspond to SEQ ID NO.15 and SEQ ID NO.12 respectively
VL1 with VH4 which correspond to SEQ ID NO.15 and SEQ ID NO.13 respectively
VL1 with VH5 which correspond to SEQ ID NO.15 and SEQ ID NO.14 respectively
VL2 with VH2 which correspond to SEQ ID NO.16 and SEQ ID NO.11 respectively
VL3 with VH2 which correspond to SEQ ID NO.17 and SEQ ID NO.11 respectively
VL3 with VH4 which correspond to SEQ ID NO.17 and SEQ ID NO.13 respectively In a preferred embodiment, the humanized variant of anti GPVI Fab is association of VL1 with VH3 corresponding to SEQ ID NO.15 with SEQ ID NO.12.

In one aspect of the invention, the VH of the anti-GPVI antibodies can be further modified by the addition of tags or amino acid extensions (peptide) to mask the antibody from recognition by preexisting antibodies. A sequence of six or more histidine residues, in particular $(His)_6$, or $(His)_7$, or $(His)_8$, or a unit such as GlyGlyGlyGlySer or $(GlyGlyGlyGlySer)_2$ can be added at the C-terminus of the heavy chain.

As used herein, "engineered Fab Fragment" refers to Fab fragments that have been genetically engineered to contain a peptide extension of the heavy chain at the c-terminus. The extension causes the previous c-terminus to be obscured and prevents recognition and binding of the Fab fragments to pre-existing anti-Fab antibodies.

In another embodiment of the invention, an engineered Fab fragment comprising a combination of a humanized heavy chain (HC) amino acid sequence and a humanized light chain (LC) amino acid sequence and a c-terminal extension is provided. The engineered Fab fragment further comprises a combination of a heavy chain variable region (HCVR) amino acid sequence and a light chain variable region (LCVR) amino acid sequence, selected from the group consisting of (a) LCVR (SEQ ID NO.15) and HCVR (SEQ ID NO.10);
(b) LCVR (SEQ ID NO.15) and HCVR (SEQ ID NO.11);

(c) LCVR (SEQ ID NO.15) and HCVR (SEQ ID NO.12);
(d) LCVR (SEQ ID NO.15) and HCVR (SEQ ID NO.13);
(f) LCVR (SEQ ID NO.16) and HCVR (SEQ ID NO.11);
(g) LCVR (SEQ ID NO.17) and HCVR (SEQ ID NO.11); and
(h) LCVR (SEQ ID NO.17) and HCVR (SEQ ID NO.13).
wherein the c-terminal extension is selected from the group consisting of SEQ ID NO:35; SEQ ID NO:36; and SEQ ID NO:37.

In a particular embodiment, the invention concerns a monoclonal antibody comprising the HC of SEQ ID NO.6 and the LC of SEQ ID NO.8 or a sequence having at least 80%, 85%, 90%, 95% or 99% identity with these sequences but which retains the same activity as the said monoclonal antibody.

In a more particular embodiment, the antibody Fab fragment of the invention comprises (a) heavy chain variable region having amino acid sequences defined by SEQ ID NO:6; and (b) light chain variable region having amino acid sequences defined by SEQ ID NO: 8.

The invention also concerns nucleic acids encoding anti-GPVI antibodies and Fab of the invention. In one embodiment, the nucleic acid molecule encodes a HC and/or a LC of an anti-GPVI antibody. In a preferred embodiment, a single nucleic acid encodes a HC of an anti-GPVI antibody and another nucleic acid molecule encodes the LC of an anti-GPVI antibody.

In a particular embodiment, nucleic acids or polynucleotides encoding polypeptides of the HC and LC from the antibody from hybridoma 390 correspond to SEQ ID NO.5 and SEQ ID NO.7 respectively, or a sequence having at least 80%, 85%, 90%, 95% or 99% identity with these sequences but which retains the same activity as the said monoclonal antibody.

The polynucleotide encoding a polypeptide selected from the group consisting in SEQ ID NO.6, SEQ ID NO.8, SEQ ID NO.9, SEQ ID NO.10, SEQ ID NO.11, SEQ ID NO.12, SEQ ID NO.13, SEQ ID NO.14, SEQ ID NO.15, SEQ ID NO.16, and SEQ ID NO.17 or a sequence having at least at least 80%, 85%, 90%, 95% or 99% identity with these sequences but which retains the same activity as the said monoclonal antibody are also part of the present invention.

The invention provides vectors comprising the polynucleotides of the invention. In one embodiment, the vector contains a polynucleotide encoding a HC of an anti-GPVI antibody. In another embodiment, said polynucleotide encodes the LC of an anti-GPVI antibody. The invention also provides vectors comprising polynucleotide molecules encoding, fusion proteins, modified antibodies, antibody fragments, and probes thereof.

A vector of the invention contains polynucleotides of SEQ ID NO.5 or SEQ ID NO.7 or any polynucleotide encoding a polypeptide selected from the group consisting in SEQ ID NO.6, SEQ ID NO.8, SEQ ID NO.9, SEQ ID NO.10, SEQ ID NO.11, SEQ ID NO.12, SEQ ID NO.13, SEQ ID NO.14, SEQ ID NO.15, SEQ ID NO.16, and SEQ ID NO.17 or a sequence having at least at least 80%, 85%, 90%, 95% or 99% identity with these sequences but which retains the same activity as the said monoclonal antibody.

In order to express the HC, fragment of HC and/or LC of the anti-GPVI antibodies or Fab of the invention, the polynucleotides encoding said HC and/or LC are inserted into expression vectors such that the genes are operatively linked to transcriptional and translational sequences. Expression vectors include plasmids, YACs, cosmids, retrovirus, EBV-derived episomes, and all the other vectors that the skilled man will know to be convenient for ensuring the expression of said heavy and/or light chains. The skilled man will realize that the polynucleotides encoding the HC/or HC fragment and the LC can be cloned into different vectors or in the same vector. In a preferred embodiment, said polynucleotides are cloned in the same vector.

Polynucleotides of the invention and vectors comprising these molecules can be used for the transformation of a suitable mammalian or microbial host cell. Transformation can be by any known method for introducing polynucleotides into a cell host. Such methods are well known of the man skilled in the art and include dextran-mediated transformation, calcium phosphate precipitation, polybrene-mediated transfection, protoplast fusion, electroporation, encapsulation of the polynucleotide into liposomes, biolistic injection and direct microinjection of DNA into nuclei.

The humanized and engineered variants of the invention are fully functional to antagonize the GPVI pathway activities. In particular, they are able to inhibit the binding of collagen to GPVI. They are also able to inhibit platelet aggregation induced by collagen both in human platelet rich plasma and in human whole blood. Further, they are also able to inhibit thrombus formation under flow on a collagen coated surface.

The binding of anti-GPVI Fab fragments of the invention to GPVI is characterized by the development of a GPVI depletion phenotype on the platelet surface. This is a new and unexpected mechanism of action for anti-GPVI Fab fragments. This unique characteristic of the Fab fragments described here, may be determined by the new epitope targeted by these molecules.

As used herein, "GPVI depletion phenotype" refers to the cellular state that results when an antibody or an antigen binding fragment binds to GPVI receptor molecules on the surface of a platelet, it prevents, the activation of the GPVI pathway on platelets. This GPVI depletion phenotype may rely on two different mechanisms: (i) either GPVI receptors are removed or depleted from the cell surface, or (ii) the antibody or an antigen binding fragment binds to GPVI receptor molecule in a non reversible way so that inhibition of the receptor is maintained for the life span of the cell. The phenotype will in both situations revert only with the renewal of platelets.

The fact that these anti-GPVI Fab fragments induce a GPVI depletion phenotype presents two advantages in term of efficacy:

i) If receptor shedding is—at least part of the mechanism, the process is generally independent of Fab binding to GPVI. This means if occupation of a fraction of cell surface GPVI by the Fab (e.g. 30%) will induce shedding, the shedding process will not be restricted to the 30% of GPVI receptors occupied by the Fab but also extended to free GPVI. This implies that one can achieve 100% of GPVI blockage (by depletion) with significantly less Fab.

ii) The inhibition effect has a long term effect: It is known that Fab fragments have a very short plasma half life of approximatively 1-2 hours, which may be problematic for several indications where a long lasting inhibition of the target is required. With the described mechanism of depletion or non-reversible occupancy of the receptors, the duration of the effect (based on pharmacodynamics properties) will be uncoupled from the pharmacokinetics properties of the Fab. This is because platelets are not able to replace the affected receptors, once depletion or non-reversible inhibition is induced Then the receptors remain absent or unavailable for the life span of the platelet. That corresponds to an extension of the duration of action to several days, depending on the half life of platelets (10 days for human platelets).

All these properties demonstrate that Fab of the present invention are suitable candidates to the treatment of thrombotic and vascular diseases.

Important target classes for antibody based biologics are membrane receptors that can be blocked with high specificity by monoclonal antibodies. Full length antibodies in the IgG format bind and also block their target through their Fv part. The Fc part add further functionality to these molecules that lead to antibody derived cellular cytotoxicity (ADCC) or complement dependent cytotoxicity (CDC). These activities are often an important part of the mAb mode of action (MoA) especially for oncology applications. However, in other application areas ADCC/CDC activities need to be minimized or are not necessary. Therefore, a number of antibody fragments lacking the Fc part such as Fab molecules are desireable.

Another reason for developing monovalent antibody fragments derives from the target biology. Many membrane receptors initiate signaling after receptor clustering (e.g. GPVI). If such a receptor should be blocked, a monovalent antibody fragment is the natural format of choice.

Antibody fragments such as Fab fragments are much more suitable formats than whole antibodies for many clinical applications. This advantage relies on several unique characteristic of Fab fragments which differentiate them from whole antibodies, in particular:
- monovalancy: required if cross-linking of molecules should be avoided
- lack of Fc domain: required if Fc-functions are not needed or undesireable
- lower molecular weight: determines pharmacokinetic and pharmacodynamic behavior as well as tissue distribution In order to maintain these desired properties of antibody Fab fragments following the administration to a patient, interaction of Fab fragments with non-target molecules should be avoided.

As previously mentioned, the Fab fragments are obtained by deletion of the constant domain of the heavy chain (Fc part) of IgG molecule. Unfortunately, removal of the Fc exposes a novel C-terminal (or C-terminal) peptide, i.e. a neoepitope. A specific class of proteins, able to specifically interact with the C-terminal extremity of Fab fragments has been reported in humans and have been identified as preexisting antibodies against antibody fragments such as Fab (Kormeier et al. (1968) J. Immunol. 100(3); 612-21; Persselin and Stevens (1985) J. Clin. Invest. 76; 723-30). These preexisting antibodies are being formed early in life and are patient dependant. With the development of monoclonal antibodies and antibody fragments as novel therapeutics, the existence of preexisting anti-Fab antibodies restricts and complicates the usage of therapeutic Fab molecules for the reasons mentioned above.

In addition, the C-terminal extremity of the Fab is a preferred epitope for generation of antibodies as previously described (Christopoulos C., et al 1994). However, even in cases were the patient has no or low amounts of pre-existing antibodies against the C-terminus, the generation of new antibodies directed toward this epitope may appear after therapeutic Fab administration, leading to this same limitations as described with preexisting antibodies.

Indeed, binding of therapeutic Fab molecule by preexisting or new antibodies against Fab C-terminal epitope can change the pharmacokinetic and pharmacodynamic behavior of the molecules (e.g. receptor activation instead of inhibition based on the change from a monovalent to bivalent molecules), create new complexes and functions (e.g. adding an antibody Fc-part with all its effector functions) and changes the size of the complex which may also have consequences for tissue distribution. Therefore, this phenomenon represents a significant safety and efficacy risk which needs to be avoided.

In order to avoid such limitations, the neoepitope that is recognized by anti-Fab antibodies can be masked by addition of a molecule at the C-terminal end of the Fab as presently described for anti-GPVI Fab molecules. This principle is essential for development of all therapeutic antibody fragments in which the target biology prevents the use of bivalent molecules (e.g. in case of receptor activation through clustering) and where it is therefore strictly required to employ mono-valent molecules.

Therefore, in order to enable the safest treatment for all patients as well as to avoid patient specific pharmacokinetic and pharmacodynamic variability, Fab molecules should be modified to mask Fab specific neoepitopes created at the C-terminal extremity that could be recognized by preexisting or newly generated antibodies against Fab fragments.

This invention concerns a Fab fragment where a molecule has been added to the C-terminus. This molecule can be a peptide or any other kind of molecule able to mask the epitope but without interfering with the binding of the Fab to the target.

In a particular embodiment, the said molecule able to mask the neoepitope of the Fab fragment is a peptide which can comprise 1 to 100 amino acids, 1 to 50 amino acids, 1 to 20 amino acids, 1 to 15 amino acids or 1 to 10 amino acids.

For example, a His-tag, a G4S or (G4S)2 stretches peptide will constitute an appropriate molecule.

In another aspect, the invention concerns a Fab bearing a molecule at the C-terminal extremity of its heavy chain.

In particular embodiment, the Fab fragment bearing a molecule at its C-terminal extremity specifically recognizes GPVI. In a preferred embodiment, this Fab fragment is chosen among those previously described.

In a particular embodiment, the sequence of the Fab heavy chain corresponds to a sequence comprising SEQ ID NO. 29 or SEQ ID NO.30 or SEQ ID NO.31.

In another embodiment, the sequence of the Fab heavy chain corresponds to a sequence consisting in SEQ ID NO. 29 or SEQ ID NO.30 or SEQ ID NO.31.

This invention also concerns a method to prevent recognition of Fab fragments by preexisting antibodies or new antibodies directed toward the C-terminal extremity consisting in masking the C-terminal end by addition of a molecule. As such, this molecule allows prevention of unwanted generation of Fab-antibody complexes.

This invention is also directed toward a method of prevention of platelet activation when an anti-GPVI Fab is used consisting in masking the C-terminal extremity of the Fab by addition of a molecule.

In another aspect, the invention concerns a method for preparation of a modified Fab bearing a molecule at its C-terminal extremity comprising the steps of:
  a. Addition of a molecule to the C-terminal extremity of the Fab
  b. Production of the modified Fab in an appropriate system, including in bacteria, yeast or mammalian cell lines
  c. Purification of the modified Fab The produced Fab can further be formulated in an appropriate solution.

In another aspect, the inventions consists in the use of an anti-GPVI antibody, in particular Fab fragments as described in the present description, to prevent thrombotic events in the treatment of certain clinical indications, as for example acute coronary syndrome, percutaneous coronary intervention, ischemic stroke, carotid artery stenosis or peripheral arterial occlusive disease. Furthermore it could be used for the prevention of restenosis and atherosclerosis.

The invention concerns also a composition containing an anti-GPVI antibody of the invention, and in particular Fab fragments with appropriate excipients. This composition can be used to treat thrombotic and vascular diseases.

In another aspect, the invention concerns a method of manufacture of an antibody according to the invention In another aspect of the invention, the antibodies can be used for diagnosis of GPVI expression changes. It is described that changes in the expression of GPVI on the platelet surface as well as the occurrence and concentration of soluble GPVI (cleaved extracellular domain of GPVI) in plasma may well be associated with pathophysiological conditions such as acute coronary syndromes, transient ischemic attacks or stroke (Bigalke B, et al., Eur J Neurol., 2009 Jul. 21; Bigalke B. et al., Semin Thromb Hemost. 2007 March; 33(2): 179-84).

Thus, measurement of these parameters could be used to identify patients at risk for the aforementioned conditions requiring anti-thrombotic treatment and being possibly particularly susceptible for anti-GPVI treatment. Therefore, antibodies and antibody fragments described here can be used as diagnostic tool and be part of a diagnostic kit which determines the presence and quantitative changes of GPVI on the platelet surface as well as in plasma samples.

The antibodies and fragments thereof can be used to diagnosis patients at risk who could benefit of an anti-thrombotic treatment.

Such method for diagnosing of GPVI changes in a patient, may comprise (i) contacting platelets or plasma sample of said patient with an antibody or Fab fragments thereof according to the invention, (ii) measuring the binding of said antibody or Fab to the cells present in said sample, and (iii) comparing the binding measured in step (ii) with that of a normal reference subject or standard.

The invention also encompasses a diagnosis kit for the detection of changes in the human GPVI expression including an antibody of the invention or a fragment thereof. In a particular embodiment, a kit according to the invention can be provided as an ELISA assay kit.

In another aspect of the invention, patients are screened for the presence of anti-Fab antibodies prior to administration of either a masked Fab or other antibody of the invention.

The invention also provides a method for the preparation of anti-GPVI antibody or Fab fragments of the invention comprising the steps of:
  a. Culture of a cell line containing DNA sequences encoding one HC or HC fragment and one LC of the invention
  b. Purification of the antibody or Fab expressed in the culture medium
  c. Formulation of the antibody in a convenient form Any expression cell line able to produce immonuglobulin can be used in order to express the antibodies of the invention. Expression cell lines derived from mammalian can be used as well as any other expression system as for example yeast cells (A. H. Horwitz, et al PNAS. 1988 November; 85(22): 8678-82) or bacterial cells (Chiba Y, Jigami Y. Curr Opin Chem Biol. 2007 December; 11(6): 670-6).

The purification of the antibody can be realized by any method known by the person skilled in the art as for example.

The formulation of the antibody depends on the intended use of such antibody. Depending on the use, for example pharmaceutical use, veterinary or diagnosis use, it can be lyophilized or not, be solubilized in an appropriate solution.

It should be noticed that this general description as well as the following detailed description are exemplary and explanatory only and should not be restrictive on the invention. The drawings included in the description illustrate several embodiments of the invention intended to explain the principles of the invention.

BRIEF DESCRIPTION OF THE FIGURES

FIG. 16: GPVI with the 20 residues signal sequence removed (corresponds to SEQ ID NO: 32). Bolded residues represent the conformational epitope making contact with antibody CDRs

EXAMPLES

Example 1

Figure 1A:
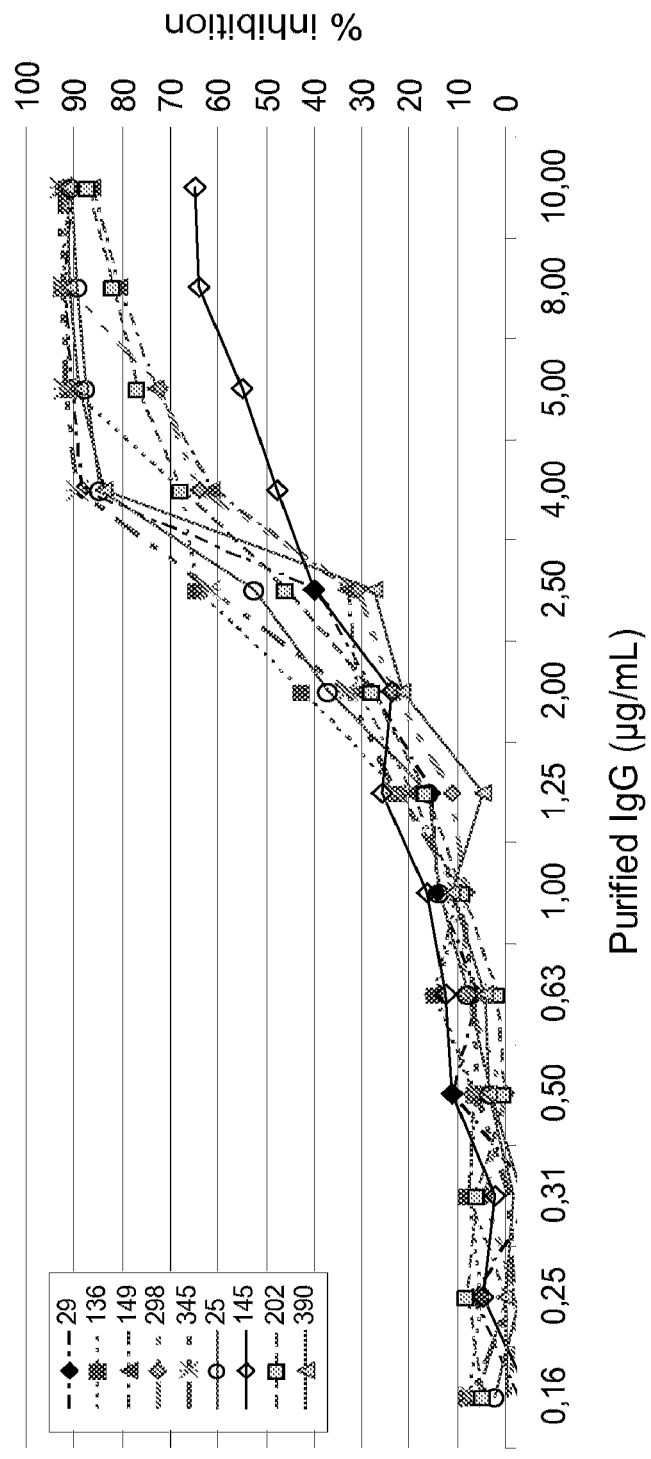
FIG. 1: Inhibition of collagen binding by competition ELISA. (A) Dose-dependency (IC50) against hGPVI-Fc and (B) against Maccaca GPVI-Fc

Generation of Recombinant Extracellular D1 and D2 Domain of GPVI

A—Construction of hGPVI-hFc Fusion Expression Plasmid (hGPVI-hFc)

Using human cDNA containing plasmids as a PCR template, a DNA fragment encoding a 237 amino acid residue heavy chain constant region including the hinge region, CH2 and CH3 domains of human immunoglobulin IgG was amplified.

Using human genomic DNA as PCR template, a DNA fragment encoding a 205 amino acid residue human GPVI D1 and D2 extracellular domains was amplified. This human GPVI D1 and D2 fragment includes the signal sequence and corresponds to amino acids M1 to T205 in the wild type protein (NP_057447/Q9HCN6). The resulting amplified, cleaved and purified PCR products encoding human GPVI D1 and D2 and a human Fc region were combined by ligation PCR and ligated into baculovirus expression vector pVL1393 by InFusion method using EcoRI and NotI site. The resulting GPVI-Fc ORF is listed as SEQ ID NO.1 and its corresponding protein sequence as SEQ ID NO.2.

B—Construction of GPVI-tev-his Expression Plasmid (GPVI-tev-his)

Using the previously described GPVI-Fc containing plasmid as PCR template, human GPVI D1 and D2 extracellular domains were amplified, including the signal sequence corresponding to amino acids M1 to T205 in the wild type protein (Swissprot: Q9HCN6). The reverse primer contained DNA coding for a tev cleavage recognition sequence and 7 histidine residues representing the His-tag at the C-terminus of the construct. The resulting amplified PCR fragment was cleaved with the restriction endonucleases EcoRI+NotI and was ligated into baculovirus expression vector pVL1393. The resulting ORF is listed as SEQ ID NO.3 and its corresponding protein sequence as SEQ ID NO.4.

C—Expression and Purification of hGPVI-hFc and GPVI-tev-his Protein

SF9 cells growing in SF900 II serum free suspension culture (Invitrogen) were cotransfected with the expression plasmid and FlashBac baculovirus DNA (Oxford Expression Technologies). Transfection was performed using Cellfectin transfection reagent (Invitrogen). After 5 h, 5% total bovine fetal serum was added to the transfected culture. The cells were cultured at 28° C. for 5 days. The culture supernatant containing recombinant virus was used for larger scale virus amplification in SF900 II suspension culture containing 5% bovine fetal serum.

For protein expression HighFive (Invitrogen) cells growing in ExCell 405 (SAFC) were transduced with an appropriate amount of virus stock and grown at 27° C. for 72 h. After harvest the cell culture supernatant was clarified by filtrated (0.22 μm).

For purification the Fc-fusion GPVI protein variants were captured on protein A matrix (GE Healthcare) and eluted by pH shift. After polishing the protein by SEC using a Superdex 200 (GE Healthcare) and a final ultrafiltration concentration step the protein was used for ELISA and further assays.

For purification the His-tagged GPVI protein variants were directly captured from supernatant on IMAC matrix (His-Trap, GE Healthcare) and eluted by an imidazol gradient. After polishing the protein by SEC using a Superdex 75 (GE Healthcare) and ultrafiltration the protein was used in indicated experiments.

Example 2

Generation and Selection of Functional Anti-GPVI mAbs

A—Generation of Anti-GPVI mAbs

GPVI-specific antibodies were generated using the RIMMS method as described by Kilpatrick et al. (1997. Hybridoma 16: 381389).

6-8 weeks old female BALB/c mice (S082342; Charles River Labs, Bar Harbor, Me.) each received four rounds of immunization with purified soluble his-tagged GPVI protein (prepared as described in Example 1) over a course of 14 days at intervals of 3-4 days.

For the first immunization on day zero, 5 μg antigen emulsified in Titermax's adjuvant (TierMax Gold Adjuvant; Sigma #T2684) was administered subcutaneously to six sites proximal to draining lymph nodes, along the back of the mice. Another 5 μg of antigen emulsified in RIBI's adjuvant (Sigma Adjuvant system; Sigma #S6322) was administered to six juxtaposed sites along abdomen. Booster immunizations were given on days 4, 7 and 11 in a similar fashion.

Four days after the last injection, mice were sacrificed. Bilateral popliteal, superficial inguinal, axillary and branchial lymph nodes were isolated aseptically and washed with fresh RPMI medium. Lymphocytes were released from the lymph nodes and the resulting single-cell suspension was washed twice with RPMI medium before being fused with P3X63-AG8.653 myeloma cells using polyethylene glycol. After fusion, the cell mixture was incubated in an incubator at 37° C. for 16-24 hours. The resulting cells preparation was transferred into selective semi-solid medium and aseptically plated out into 100 mm Petri plates and incubated at 37° C.

Ten days after initiation of selection, the plates were examined for hybridoma growth, and visible colonies were picked-up and placed into 96-well plates containing 200 μL of growth medium. The 96-well plates were kept in an incubator at 37° C. for 2 to 4 days.

B—Screening for mAbs Recognizing the Human GPVI Protein

Primary screening for anti-GPVI IgG production was performed by ELISA using GPVI-Fc fusion protein (prepared as described in Example 1) as capturing antigen. Plates were coated with GPVI-Fc fusion protein and hybridoma supernatants were added to the plate and detected by using rabbit anti-mouse IgG conjugated with horseradish peroxidase (Sigma; #A9044). Antibody binding was visualized by adding TMB-H2O2 buffer and read at a wavelength of 450 nm.

Among 367 hybridomas selected from 96-well plates, 129 hybridomas were positive for anti-human GPVI antibody production and then 111 were confirmed after cell amplification.

C—Ability of Anti-GPVI mAbs to Block Binding of Collagen to Human GPVI

A secondary screening was performed to characterize functional properties of all human GPVI-specific mAbs for their ability to block the binding of collagen to human GPVI-Fc fusion protein in a competition ELISA binding assay. Custom-made collagen coated 96-well plates (Pierce) were used. Pre-incubated mixture of human GPVI-Fc fusion protein and hybridoma supernatants were added to the plate and collagen-human GPVI-Fc complex was detected by using goat anti-human IgG-Fc conjugated with horseradish peroxidase (Sigma; #A0170). The antibody binding was visualized by adding TMB-H2O2 buffer and read at a wavelength of 450 nm. Among the 100 GPVI-binding hybridomas, 22 hybridomas blocked the binding of GPVI-Fc to collagen (threshold: 90% inhibition). The blocking properties of pre-selected mAbs to human GPVI were confirmed to be dose-dependent using a competition ELISA assay as shown in FIG. 1A.

All antagonist mAbs were isotyped as IgG1, kappa, as determined by using a mouse IgG isotyping kit (SEROTEC; #MMT1) (data not shown).

D—Binding Properties of the Anti-GPVI mAbs

A last screening was performed by Surface Plasmon Resonance (BIAcore 2000) to evaluate binding properties of GPVI blocking antibodies. In this analysis, we evaluated the interaction of the human GPVI protein with the anti-human GPVI mAbs fixed to anti-Fc antibody covalently linked to CM chips. Binding kinetics of the individual mAbs were performed using the protocol described by Canziani et al 2004. Anal. Biochem. 325: 301-307.

All blocking mAbs displayed affinities in the (sub)nanomolar range to human GPVI (Table 1). Based on target affinities, the antibody from hybridoma clone 390 was selected for further development.

TABLE 1

Affinity and association/dissociation rates of selected anti-hGPVI mAbs

| | Biacore | | |
|---|---|---|---|
| Hybridoma | ka (1/Ms) | kd (1/s) | $K_D$ (M) |
| 25 | 6.05E+04 | 2.57E−04 | 4.2E−09 |
| 29 | 15.4E+04 | 3.28E−04 | 2.1E−09 |
| 136 | 15.2E+04 | 3.16E−04 | 2.0E−09 |
| 145 | 5.87E+04 | 8.63E−04 | 14.7E−09 |
| 149 | 1.27E+04 | 1.49E−04 | 11.7E−09 |
| 202 | 1.33E+04 | 2.10E−04 | 15.8E−09 |
| 298 | 85E+04 | 18.2E−04 | 2.1E−09 |
| 345 | 16.7E+04 | 3.29E−04 | 1.9E−09 |
| 390 | 10.8E+04 | 0.04E−04 | 0.04E−09 |

Figure 1B:
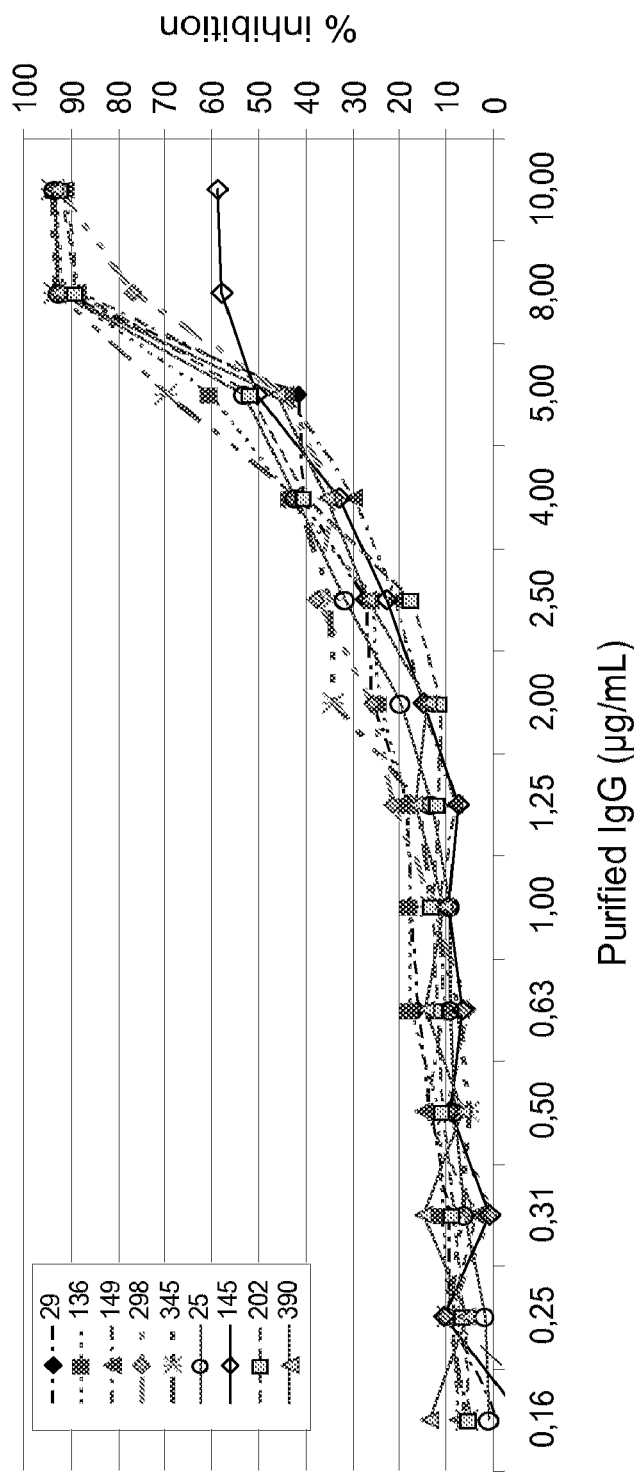
Figure 2:
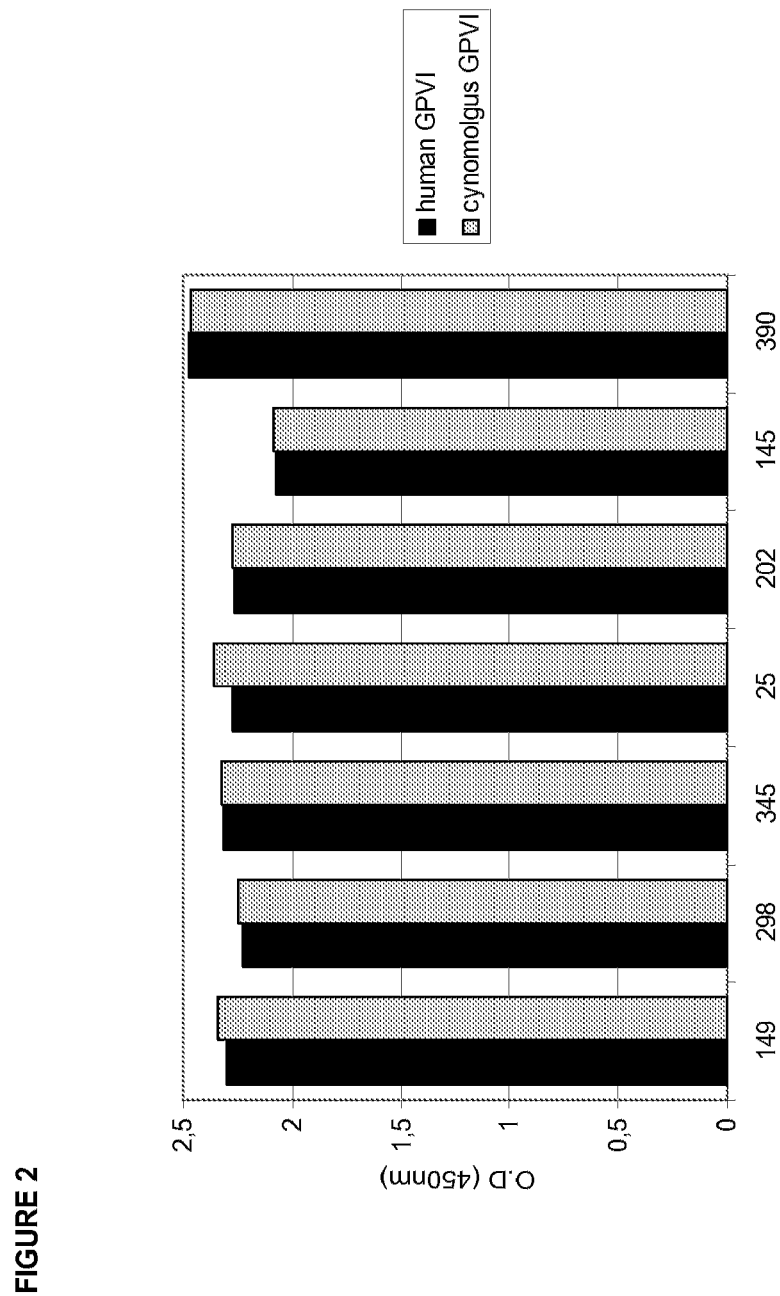
FIG. 2: Cross-reactivity analysis of selected hybridoma mAb against human and primate GPVI by ELISA

E—Cross-Reactivity Properties of the Anti-GPVI mAbs with the Primate GPVI Protein GPVI-specific mAbs listed in table 1 were assessed for their ability to bind primate GPVI-Fc protein by ELISA. Plates were coated with primate GPVI-Fc fusion protein, anti-hGPVI mAbs were added to the plate and detected with rabbit anti-mouse IgG conjugated with horseradish peroxidase (Sigma; #A9044). The antibody binding was visualized by adding TMB-H2O2 buffer and read at a wavelength of 450 nm. The pre-selected hybridomas were cloned by growth in semi-solid medium. Petri plates were seeded at 125 cell/mL and clones showing significant growth were screened for GPVI binding, GPVI blocking activity and cross reactivity with primate GPVI. As shown in FIG. 1B and FIG. 2, all mAbs were cross-reactive with primate GPVI.

The sequences used for extracellular domain of primate (*Macaca fascicularis* or cynomolgus) GPVI are described as SEQ ID NO.27 and SEQ ID NO.28.

F—Determination of the Sequence of the Heavy and Light Chains of the Anti-GPVI mAbs The cDNA encoding the variable domains of the monoclonal antibodies were obtained as follows: mRNA was extracted from hybridoma cells with the Oligotex kit from Qiagen. The corresponding cDNA was amplified by RT-PCR by the RACE method utilizing the Gene Racer kit (Invitrogen), the transcriptase SuperScript III at 55° C. (Invitrogen) and primers described on Table 2 (RACEMOG1 or CKFOR). The cDNA fragments were amplified by PCR with the polymerase Phusion at 55° C. (Finnzymes) and primers also described in Table 2.

TABLE 2

Primers used for RT-PCR and PCR

| Primer | Sequence number |
|---|---|
| 5'-GeneRacer Primer | SEQ ID NO. 24 |
| RACEMOG1: 3'-Primer internal to murin hinge murin | SEQ ID NO. 25 |
| CKFOR: 3'-Primer internal to murin Ck murin | SEQ ID NO. 26 |

The amplified fragments encoding the variable regions of heavy (VH) and light (VL) chains were cloned into the pGEM-T Easy plasmid from Promega or pCR4-Topo plasmid from Invitrogen which were amplified in *E. coli*. Cloned cDNA was then sequenced on both strands.

Protein sequences were translated from plasmid coding sequences and the masses of the heavy (HC) and light (LC) chains were calculated (Table 3). The values obtained were in perfect agreement with mass spectrometry data obtained from preparations of mAbs purified from cultures of the corresponding hybridoma, see Table 3. In particular, the occupancy of a N-glycosylation site in the variable region of the heavy chain (NST) of anti-GPVI antibody 390 was confirmed. Amino acid sequence of HC and LC are reported in the sequence listing as follows: SEQ ID NO.5 and SEQ ID NO. 6 corresponds to the HC of anti-GPVI mAb from clone 390 and SEQ ID NO.7 and SEQ ID NO. 8 correspond to the LC of anti-GPVI mAb from clone 390.

TABLE 3

Mass spectrometry analysis of Anti-GPVI mAbs from hybridoma

| Anti-GPVI mAb | Chain | Mass (Da) by LC/MS | Mass (Da) in silico value |
|---|---|---|---|
| 390 | LC | 23417 | 23414 |
| | HC | 51127 | 49586 (G0)* |

*Compatible with additional high mannose N-glycan. Mass of 49586 Da confirmed by LC/MS analysis after deglycosylation.

G—Determination of the Sequences of the CDR of the Anti-GPVI mAbs

The sequences for the CDR regions were deduced from the protein sequence using the KABAT nomenclature.

For the HC, CDR1 corresponds to SEQ ID NO.18, CDR2 corresponds to SEQ ID NO.19 CDR3 corresponds to SEQ ID NO.20

For the LC, CDR1 corresponds to SEQ ID NO.21, CDR2 corresponds to SEQ ID NO.22 CDR3 corresponds to SEQ ID NO.23

Example 3

Figure 3:
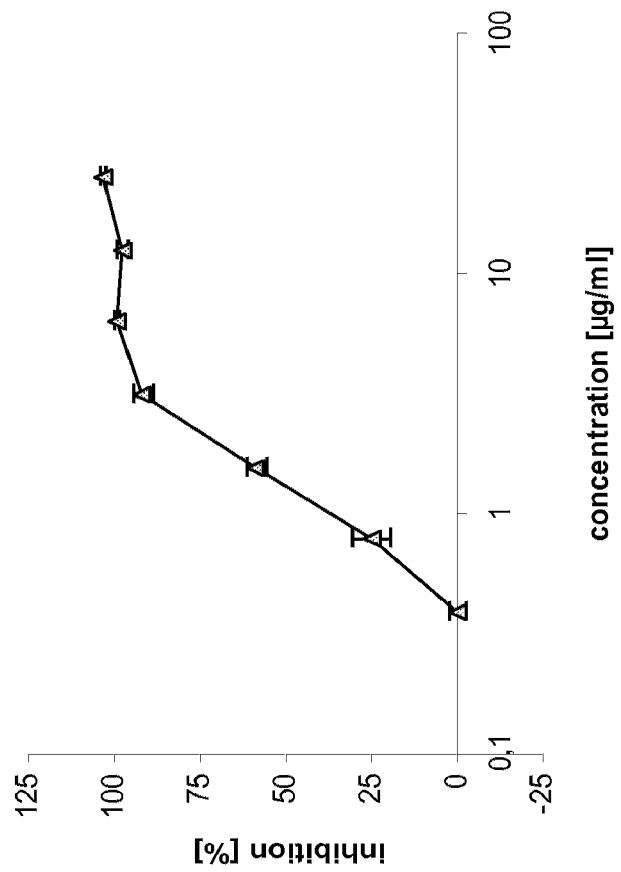
FIG. 3: Fab produced by Ficin cleavage of IgG from hybridoma clone 390
Figure 4:
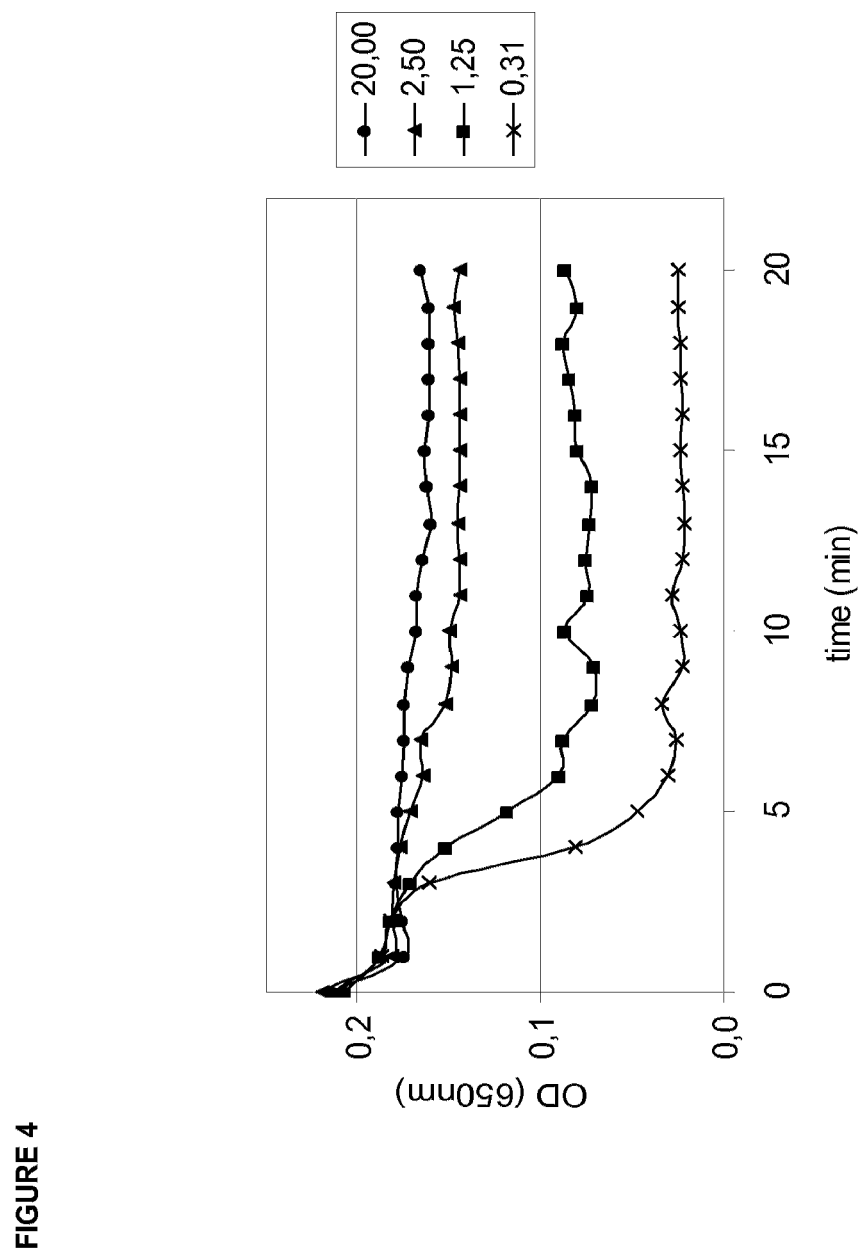
FIG. 4: Inhibition of collagen induced platelet aggregation by anti-GPVI Fab fragments (VL1 with VH3).

Preparation and Biophysical Properties of Anti-GPVI mAbs and their Fab Fragments A—Inhibition of Collagen Binding to Recombinant GPVI by Anti-GPVI IgG's or their Proteolytic Fab Fragments Collagen coated 384well plates (Pierce) were blocked with 3% BSA for 2 h. Increasing concentrations of IgG or its corresponding Fab fragment produced by Ficin cleavage (0.3-20 µg/ml) were incubated with recombinant GPVI (Fc-fusion protein of the extracellular GPVI domain; 3 µg/ml) for 30 min. The GPVI-IgG mixture was added to collagen coated plates and incubated for 1 h at RT. Next, 384well plates were washed (DELFIA wash buffer, Perkin Elmer) five times and Eu-labelled anti-human IgG (100 ng/ml Perkin Elmer) was added. Following 1 h incubation at room temperature plates were washed again five times, enhancement solution (Perkin Elmer) was added and incubated for 10 min. Fluorescence was detected at 360/612 nm using a Tecan Ultra reader. FIG. 3 shows a typical readout. Table 4 shows calculated IC50 values (µg/ml) for inhibition of collagen binding to GPVI of two independent experiments.

TABLE 4

Calculated IC50 values (μg/ml) for inhibition of collagen binding to GPVI of two independent experiments.

| Hybridoma | IgG | | Fab (Ficin cleavage) | |
|---|---|---|---|---|
| Clone ID | Test 1 | Test 2 | Test 1 | Test 2 |
| 390 | 5.6 | 5.0 | 1.3 | 1.1 |

B—Production of Recombinant Fab Fragments

1. Construction of Expression Plasmids for Recombinant Production of Anti-GPVI Fab Amino acid sequences of the variable heavy and light chains of the anti-human GPVI antibodies were backtranslated into nucleotide sequence and generated respectively using either a modified protocol of the overlap extension PCR (OE-PCR) described by Young L. and Dong Q. (Nucl. Acids Res. (2004), 32(7), e59) or by gene synthesis (Geneart). PCR products were cloned into the pCR Blunt II TOPO vector using the Invitrogen TOPO cloning kit and sequenced using M13 forward and M13 reverse primers. Each variable heavy chain was fused to the CH1 domain of IGHG1 (Genebank accession number Q569F4) and the variable light chain was fused to the constant kappa chain (IGKC, Genebank accession number Q502W4) respectively. These fragments were digested with NheI and HindIII and each ligated into the NheI/HindIII sites of the episomal expression vector pXL, an analogon of the pTT vector described by Durocher et al. (2002), Nucl. Acids Res. 30(2), E9, creating the plasmids for transient mammalian expression of the chimeric and humanized anti-GPVI Fabs. The expression plasmids encoding the heavy and light chain of the antibody were propagated in $E.\ coli$ NEB 10-beta (DH10B derivative). Plasmids used for transfection were prepared from $E.\ coli$ using the Qiagen EndoFree Plasmid Mega Kit.

2. Transient Expression and Purification of Recombinant Anti-GPVI Fab Fragments

Hek 293-FS cells growing in Freestyle Medium (Invitrogen) were transfected with indicated LC and HC plasmids using Fugene (Roche) transfection reagent. After 7 days the cells were removed by centrifugation, 10% Vol/Vol 1M Tris HCl pH 8.0 was added and the supernatant was passed over a 0.22 μm filter to remove particles. The Fab proteins were captured using KappaSelect matrix (GE Healthcare) and eluted via pH shift. The protein containing fractions were pooled and desalted using PD-10 or Sephadex columns. Concentrated and sterile filtered (0.22 μm) protein solutions were adjusted to 1 mg/ml and kept at 4° C. until use.

C—Biophysical Characterization of Recombinant Fab

Surface plasmon resonance technology on a Biacore 3000 (GE Healthcare) was used for detailed kinetic characterization of purified antibody fragments. A direct binding assay was used with the anti-GPVI Fab as the ligand and human GPVI as analyte. Typically, 500 RU of anti-GPVI Fab were immobilized on a research grade CM5 chip by amine reactive coupling, resulting in an Rmax of 200 RU for the bound GPVI molecule. Binding kinetics were measured over a concentration range typically between 0.8 to 208 nM in HBS-EP (10 mM HEPES pH 7.4, 150 mM NaCl, 3 mM EDTA, 0.005% Surfactant P20) at a flow rate of 30 μl/min. Chip surfaces were regenerated with 10 mM glycine pH 2.0. Kinetic parameters were analyzed and calculated in the BIAevaluation program package (version 4.1) using a flow cell without immobilized Fab as reference. A 1:1 binding model with mass transfer was applied for a global fit of the data for curves.

In order to investigate functional consequences of the additional glycosylation motif present in the original sequence as derived from glycosylated clone 390 (Fab 390-G), the conserved glycosylation motif was removed by amino acid replacement (Fab 390-nG). For this purpose, two heavy chain fragments based on clone 390 were constructed: the first one does not have any modification and corresponds to SEQ ID NO.9, and the second one has a point mutation N→Q at position 60 of SEQ ID NO.9.

It is known that glycosylation can be very heterogeneous and produce glycoprotein heterogeneity; such source of heterogeneity should be avoided as much as possible.

In the present case, the removal of the additional glycan does not impact the binding affinity for GPVI as shown in Table 5. Thus, the non-glycosylated Fab 390-nG construct has been chosen for further experiment.

TABLE 5

Determination of binding characteristics for recombinant anti-GPVI Fab molecules by SPR (Biacore) Recombinant Fab

| Construct | ka (1/Ms) E+04 | kd (1/s) E−04 | KD (M) E−09 |
|---|---|---|---|
| Fab 390-G | 32 | 0.15 | 0.05 |
| Fab 390-nG | 34.8 | 0.22 | 0.06 |

D—Determination of the Epitope Recognized by the Anti-GPVI mAb by Co-Crystallization of Anti-GPVI Fab with GPVI and X-Ray Crystallography For epitope characterization a co-crystallization strategy has been applied. A complex between Fab 390-nG (expressed in HEK293 cells) and human glycoprotein VI (extracellular domain of human GPVI (Met1-Thr205), expressed in Insect cells High five) was formed by incubation of both proteins at equal molar ratio. The complex was digested with trypsin, re-purified by gelfiltration, concentrated and subjected to crystallization screening. Well diffracting crystals were obtained by mixing 100 nl of protein solution (Fab-antigen complex at 6.5 mg/ml in 20 mM Tris pH 8.0, 150 mM NaCl) with 100 nl of reservoir solution containing 0.1M BisTris pH 5.5, 25% PEG3350 and 0.2M ammonium acetate and incubating the protein drop against 200 μl reservoir solution at 4° C. in a sealed sitting drop vapour diffusion crystallization plate. One crystal was flash frozen in liquid nitrogen using reservoir solution supplemented with 25% ethylene glycol for cryoprotection. Crystallographic data was collected at the European Synchrotron Radiation Facility, Grenoble, France, at beamline ID14-4. The structure was solved by Molecular Replacement using the Fab fragment of the pdb-entry 1FDL as model for Fab 390-nG and one monomer of the crystal structure of human platelet glycoprotein VI, pdb-entry 2G17, as model for GPVI. The resolution and final R-factor of the refined structure are 1.72 Å, R-factor 17.2% and R-free 19.9%. The GPVI-binding epitope is a conformational epitope characterized by interactions (defined as distance <4.5 Å) of Fab 390-nG to the following residues of the antigen hGPVI:

Pro4, Lys7, Glu40, Lys41, Leu42, Ser43, Ser44, Ser45, Arg46, Arg65, Arg67, Trp76, Leu78, Pro79, Ser80, Asp81, Gln82, Ser165, Arg166

Figure 5C:
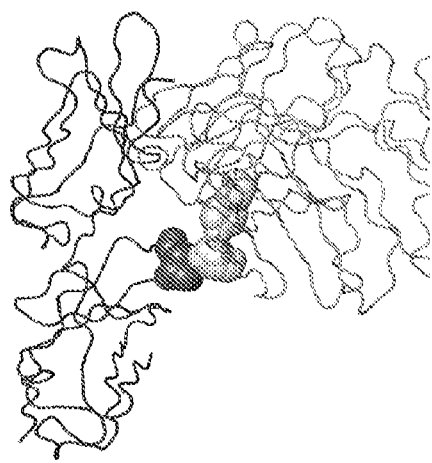
FIG. 5: Crystallographic data showing the interaction between the Fab and the extracellular domain of the human GPVI protein. (A) Interaction between D2 domain of GPVI protein and the Fab. (B) Interaction between D1 domain of GPVI protein and the Fab. (C) Interaction between D1-D2 domain of GPVI protein and the Fab.
Figure 5B:
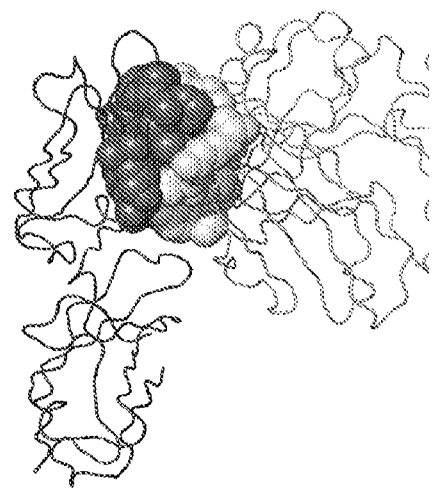
Figure 5A:
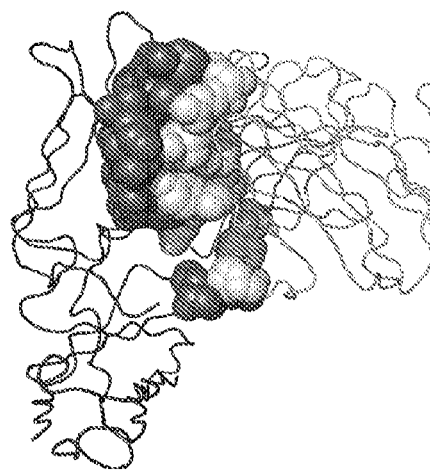

These residues belong either to the D1 domain (up to amino acid 84) or constitute parts of the D2 domain (amino acids 94 to 176) and therefore representing a conformational epitope. The numbering system for GPVI epitope residues corresponds to the protein with the signal sequence removed as shown in FIG. 16 and SEQ ID NO: 32. The interaction of Fab anti GPVI from clone 390 with the extracellar D1-D2 domain of GPVI is illustrated on FIG. 5.

The antibody residues contacting GPVI epitope residues are described in Tables 6 through Table 11 below.

As used herein, "contacting residues" were defined as antibody residues with a distance of less than 4.5 Å to GPVI antigen residues or the reverse and as measured in the crystal structure between antibody to GPVI and GPVI antigen. The distances were determined using the software program NCONT of the CCP4 Software package.

The X-ray structure highlights residues from the CDRs that can be mutated, that should not impact binding to GPVI.

In the following descriptions, residues from the CDRs might be modified as indicated, without disruption of the binding to GPVI. It is also understood that mutations in the CDRs should not affect the conformation and orientation of the residues from the CDRs to preserve binding to GPVI. Residue numbering is sequential and does not follow Kabbat conventions as used in Al-Lazikani ((1997) J. Mol. Biol. 273, 927-948). "X" represents "any residue", while "-" indicates that no modification should be made at this position.

CDRH1 sequence as defined in SEQ ID NO: 18 spans ten residues. As shown in Table 6, six of ten or 60% of CDRH1 residues do not make contact with GPVI. All of the GPVI residues in contact with antibody residues are serine residues.

CDRH3 sequence is defined in SEQ ID NO: 20 and spans five antibody residues. Based on the fact the definition of the CDR sequence can slightly vary depending on the software used, it has been found that CDRH3 may include one additional residue. Thus CDRH3 can be as defined in SEQ ID NO:38, spanning six antibody residues. As shown in Table 8 two of six or 33% of CDRH3 residues do not make contact with GPVI. Arginine 65 was found to be in contact with three different GPVI antigen residues. There are three different arginine residues of GPVI contacting CDRH3 residues.

TABLE 8

Antibody CDRH3 residues contacting GPVI antigen residues

|  | 98 | 99 | 100 | 101 | 102 | 103 |
|---|---|---|---|---|---|---|
| CDRH3 Initial sequence | D | L | P | M | D | Y |
| Suggested mutations | D/N | L/I/V | — | — | D/N | X |
| GPVI | L42 S43 R65 | L42 S43 R65 R67 | R65 | | | R166 |

TABLE 6

Antibody CDRH1 residues contacting GPVI antigen residues

|  | H26 | H27 | H28 | H29 | H30 | H31 | H32 | H33 | H34 | H35 |
|---|---|---|---|---|---|---|---|---|---|---|
| CDRH1 Initial sequence | G | F | S | L | T | G | Y | G | V | N |
| Suggested mutations | — | — | X | — | X | X | Y/F | — | — | — |
| GPVI |  |  |  |  | S44 | S43 S44 | S43 S44 | S43 S44 |  |  |

CDRH2 sequence is defined in SEQ ID NO: 19 and spans sixteen antibody residues. As shown in Table 7, nine of sixteen or 56% of CDRH2 residues do not make contact with GPVI. Tryptophan 52 was found to be in contact with seven different GPVI antigen residues. Arginine 46 of GPVI was found in contact with five different CDRH2 residues.

CDRL1 sequence is defined in SEQ ID NO: 21 and spans eleven antibody residues. As shown in Table 9, seven of eleven or 64% of CDRL1 residues do not make contact with GPVI. Tyrosine 32 was found to be in contact with five different GPVI residues.

TABLE 7

Antibody CDRH2 residues contacting GPVI antigen residues

|  | 50 | 51 | 52 | 53 | 54 | 55 | 56 | 57 | 58 | 59 | 60 | 61 | 62 | 63 | 64 | 65 |
|---|---|---|---|---|---|---|---|---|---|---|---|---|---|---|---|---|
| CDRH2 Initial sequence | M | I | W | G | D | G | S | T | D | Y | Q | S | T | L | K | S |
| Suggested mutations | — | I/V/L | — | — | — | — | S/T | X | — | Y/F | — | X | X | L/I | X | X |
| GPVI | S43 |  | E40 K41 L42 S43 S44 S45 R46 | S43 S44 S45 | S44 S45 R46 |  | R46 | R46 | R46 |  |  |  |  |  |  |  |

TABLE 9

Antibody CDRL1 residues contacting GPVI antigen residues

| | 24 | 25 | 26 | 27 | 28 | 29 | 30 | 31 | 32 | 33 | 34 |
|---|---|---|---|---|---|---|---|---|---|---|---|
| CDRL1 Initial sequence | K | A | S | Q | D | I | N | K | Y | I | A |
| Suggested mutations | X | — | X | G/E | D/N | — | — | X | — | — | — |
| GPVI | | | | P4 | L78 | | K7 P79 S80 D81 | | R67 P79 S80 D81 Q82 | | |

CDRL2 sequence is defined in SEQ ID NO: 22 and spans seven antibody residues. Based on the fact the definition of the CDR sequence can slightly vary depending on the software used, it has been found that CDRL2 may include one additional residue. Thus CDRL2 can be as defined in SEQ ID NO: 39 spanning eight antibody residues. As shown in Table 10, six of eight or 75% of CDRL2 residues do not make contact with GPVI. This CDR is in contact with residues in both D1 and D2 domains of GPVI. Tyrosine 50 is in contact with asp 81 and gln 82 in D1, while proline 56 is in contact with arg 166 and ser 165 of GPVI D2 domain.

TABLE 10

Antibody CDRL2 residues contacting GPVI antigen residues

| | 50 | 51 | 52 | 53 | 54 | 55 | 56 | 57 |
|---|---|---|---|---|---|---|---|---|
| CDRL2 Initial sequence | Y | T | S | T | L | Q | P | G |
| Suggested mutations | — | T/S | X | X | X | X | — | X |
| GPVI | D81 Q82 | | | | | | S165 R166 | |

CDRL3 sequence is defined in SEQ ID NO: 23 and spans eight antibody residues. As shown in Table 11, five of eight or 63% of CDRL3 residues do not make contact with GPVI.

TABLE 11

Antibody CDRL3 residues contacting GPVI antigen residues

| | 89 | 90 | 91 | 92 | 93 | | 94 | 95 | 96 |
|---|---|---|---|---|---|---|---|---|---|
| CDRL3 Initial sequence | L | Q | Y | A | N | | L | L | T |
| Suggested mutations | — | — | — | — | N/D/Q/E/S/T/R/K | | X | — | T/S |
| GPVI | | | L42 R67 | R67 P79 | W76 | | | | |

A summary of the contacts between GPVI residues interacting with antibody residues revealed that ser 43 has 8 contacts, ser 44 has 7 contacts, arg 46 has 4 contacts, arg 67 has 4 contacts, arg 65 has 3 contacts, asp 81 has 3 contacts, and Arg 166 has two contacts. Most GPVI residues favor either the light chain or the heavy chain, but R67 and R166 have contact with both.

E—Humanization of the Fv Domain of Anti-GPVI Fab

The humanization protocol described in the patent application WO 2009/032661 was used to humanize the Fab 390-nG clone. In addition, analysis of the crystallographic complex between Fab 390-nG and the human GPVI led to several mutations with the aim of improving or at least retaining the affinity of Fab 390-nG to human GPVI within the humanization campaign.

The VL & VH sequences of Fab 390-nG were blasted against the August 2007 version of the Protein Data Bank (PDB). The PDB structure 1L71 was used to build up a homology model of the light chain. The PDB structures 1YY8 and 1ZA6 were both used to build up a homology model of the heavy chain. The 1ZA6 structure was specifically used to model the CDR3 subregion, while the 1YY8 structure was used for the remaining part of the heavy chain. The resulting VL and VH models were used to build up a homology model of the variable domains which was subsequently energy minimized using the standard procedure implemented in Molecular Operating Environment (MOE). MOE is a software for computer assisted drug design distributed by the Chemical Computing group. The minimized model of Fab 390-nG was subsequently submitted to Molecular Dynamics simulations in order to identify the most flexible residues which are more likely to interact with T-cell receptors and responsible for activation of the immune response. The simulations were run with the AMBER software distributed by the University of California. 57 amino-acids are finally identified as flexible in the Fab 390-nG. The motion of the most 60 flexible Fab 390-nG amino-acids (excluding the CDR+5 Å region), during the 20 ns (10×2 ns), were then compared to the motion of the corresponding flexible amino-acids of 49 human germlines homology models, for each of which were run the 10×2 ns MD simulations. The 49 human germlines models were built by systematically combining the 7 most common human germline light chains (vk1, vk2, vk3, vk4, vlambda1, vlambda2, vlambda3) and 7 most common human germline heavy chains (vh1a, vh1b, vh2, vh3, vh4, vh5, vh6). The vk1-vh6 human germline sequences showed a 84% 4D similarity of its flexible amino-acids compared to the flexible amino-acids of the Fab 390-nG sequences; the vk1-vh6 germline sequences were therefore used to humanize the Fab 390-nG sequences focusing on the flexible amino-acids. For the pairwise amino-acid association between Fab 390-nG and vk1-vh6 amino-acids, the 2 sequences were aligned based on the optimal 3D superposition of the alpha carbons of the 2 corresponding homology models. The following motifs of potentially problematic sequences were considered in some cases: Asp-Pro (acide labile bond), Asn-X-Ser/Thr (glycosylation, X=any amino-acid but Pro), Asp-Gly/Ser/Thr (succinimide/iso-asp formation in flexible areas), Asn-Gly/His/Ser/Ala/Cys (exposed deamidation sites), Met (oxidation in exposed area). The resulting engineered sequences were blasted for sequence similarity against UniProtKB/Swiss-Prot database providing confidence that reasonable assumption has been made. In addition none of the sequences contains any known B- or T-cell epitope listed in the Immune Epitope Database and Analysis Resource (IEDB database).

Five versions for the heavy chain (Fab 390-nG VH1, VH2, VH3, VH4, VH5) and three versions were suggested for the light chain (VL1, VL2, VL3). All versions derive from the sequences of the ANTI-GPVI Fab 390-nG construct. The starting sequences for unhumanized Fab 390-nG are provided in SEQ ID NO33: for VH and SEQ ID NO:34 for VL. The L1 version has 4 mutations. The L2 version includes one additional mutation (N93H) to potentially improve the binding to human GPVI. The L3 version derives from L1 and includes an additional mutation to potentially improve the binding to human GPVI (N93L).

Version H1 contains 5 humanizing mutations derived from the closest human heavy chain germline sequence, VH6, as found following the previously described procedure. Version H2 contains 4 humanizing mutations and derives from H1 without mutating the amino-acid in position 73 (Asn73), which was found to be important for a potent affinity as seen in the crystallographic complex between Fab 390-nG and the human GPVI. Version H3 contains 5 humanizing mutations derived from the human heavy chain germline sequence VH3. VH3 was found to be close to the VH chain of Fab 390-nG, following the previously described procedure, and to have an asparagine (Asn) residue in position 73. The H4 version derives from H2 and includes one additional mutation (G31Y) to potentially improve the binding to human GPVI. The H5 version derives from H2 and includes one additional mutation (Y103E) to potentially improve the binding to human GPVI.

Eight combinations of VL and VH variants were recommended for generation of engineered antibodies: VL1 with VH1, VL1 with VH2, VL1 with VH3, VL2 with VH2, VL3 with VH2, VL1 with VH4, VL1 with VH5 and VL3 with VH5. As shown in Table 12 and Table 13, the amino acid changes were made in engineered VL and VH variants of the Fab 390-nG, using the methodology set forth in the detailed description section of the instant application. The left column indicates the original amino acids and their positions in the murine Fab 390-nG.

Besides the engineering of the variable domain, the antibodies and their fragments can be further modified by the addition of tags or amino acid extensions. For example a sequence of six or more histidine residues, in particular (His)$_6$, or (His)$_7$, or (His)$_8$, could be added at the C-terminus of the heavy chain or the terminus could be extended in sequence by addition of amino acids such as GlyGlyGlyGlySer or (GlyGlyGlyGlySer)$_2$ units. Similarly the framework of the antibodies and their fragments could be changed from an IgG1 backbone to another IgG backbone like IgG4.

TABLE 12

Summary of the mutations introduced into SEQ ID NO: 34 for the humanized light chain of the anti-GPVI Fab 390-nG construct

| | Light Chain (Sequential numbering as shown in SEQ ID NO: 34) | | |
|---|---|---|---|
| | L1 | L2 | L3 |
| LEU15 | VAL | VAL | VAL |
| LYS18 | ARG | ARG | ARG |
| ILE58 | VAL | VAL | VAL |
| GLU79 | GLN | GLN | GLN |
| ASN93 | ASN | HIS | LEU |
| | 4 mutations | 5 mutations | 5 mutations |

TABLE 13 summary of the mutations introduced into SEQ ID NO: 33 for the humanized heavy chain of the anti-GPVI Fab 390-nG construct

| | Heavy Chain (Sequential numbering as shown in SEQ ID NO: 33) | | | | |
|---|---|---|---|---|---|
| | H1 | H2 | H3 | H4 | H5 |
| GLN1 | GLN | GLN | GLU | GLN | GLN |
| LYS5 | GLN | GLN | LEU | GLN | GLN |
| GLN16 | GLN | GLN | GLY | GLN | GLN |
| GLY31 | GLY | GLY | GLY | TYR | GLY |
| GLY42 | SER | SER | GLY | SER | SER |
| LYS43 | ARG | ARG | LYS | ARG | ARG |
| ASN73 | THR | ASN | ASN | ASN | ASN |

TABLE 13-continued summary of the mutations introduced into SEQ ID NO: 33 for the humanized heavy chain of the anti-GPVI Fab 390-nG construct

| | Heavy Chain (Sequential numbering as shown in SEQ ID NO: 33) | | | | |
|---|---|---|---|---|---|
| | H1 | H2 | H3 | H4 | H5 |
| GLN86 | THR | THR | ARG | THR | THR |
| TYR103 | TYR | TYR | TYR | TYR | GLU |
| GLN106 | GLN | GLN | LEU | GLN | GLN |
| | 5 mutations | 4 mutations | 5 mutations | 5 mutations | 5 mutations |

F—Biophysical Characterization of Humanized Variants

Surface plasmon resonance technology on a Biacore 3000 (GE Healthcare) was used for detailed kinetic characterisation of purified antibody fragments. An assay with immobilised human GPVI was used. Typically, 300 RU of GPVI were immobilised on a research grade CM5 chip by amine reactive coupling, resulting in an Rmax of 200 RU for the bound antibody fragment. Binding kinetics were measured over a concentration range between 3.2 to 112 nM in HBS-EP (10 mM HEPES pH 7.4, 150 mM NaCl, 3 mM EDTA, 0.005% Surfactant P20) at a flow rate of 30 µl/min. Chip surfaces were regenerated with 10 mM glycine pH2.0. Kinetic parameters were analysed and calculated in the BIAevaluation program package (version 4.1) using a flow cell without immobilised GPVI as reference. A 1:1 binding model with mass transfer was applied for a global fit of the data for curves corresponding to analyte concentrations from 3-56 nM of Fab fragment.

The binding kinetics of anti-GPVI antibody fragments from the humanisation campaign are shown in Table 14. Note that the Biacore assay used to measure the data in this example is different in terms of immobilized binding partner (GPVI versus the mAb/Fab fragment) and this leads to the different Biacore affinities as reported in Table 5.

TABLE 14

Determination of binding characteristics of humanized variants of Fab 390-nG against extracellular domain of human GPVI by SPR (Biacore)

| LC/HC-Combination | ka (1/Ms) E+04 | kd (1/s) E−04 | KD (M) E−09 |
|---|---|---|---|
| Fab 390-nG | 10.2 | 0.2 | 0.2 |
| VL1/VH1 | 11.1 | 0.4 | 0.4 |
| VL1/VH2 | 11.3 | 0.3 | 0.2 |
| VL1/VH3 | 14.8 | 0.2 | 0.1 |
| VL1/VH4 | 12.4 | 0.2 | 0.2 |
| VL1/VH5 | 8.1 | 0.3 | 0.4 |
| VL2/VH2 | 10.8 | 0.3 | 0.3 |
| VL3/VH2 | 13.2 | 0.3 | 0.2 |
| VL3/VH4 | 15.1 | 0.4 | 0.3 |

Example 4

Inhibition of Collagen Binding and of Platelet Aggregation by Anti-GPVI Fab Fragments A. Inhibition of Binding of Recombinant GPVI to Collagen by Recombinant Anti-GPVI Fab Fragments Collagen coated 384well plates (Pierce) were blocked with 3% BSA for 2 h. Increasing concentrations of anti GPVI Fab fragments (0.3-20 µg/ml) were incubated with recombinant GPVI (Fusion protein of the extracellular domain of GPVI and Fc-Part of human IgG; 3 µg/ml). The GPVI-Fab mixture was added to collagen coated plates and incubated for 1 h at RT. 384well plates were washed (DELFIA wash buffer, Perkin Elmer) five times and Eu-labelled anti-human IgG (100 ng/ml Perkin Elmer) was added. Following 1 h incubation at room temperature plates were washed again five times, enhancement solution (Perkin Elmer) was added and incubated for 10 min. Fluorescence was detected at 360/612 nm using a Tecan Ultra reader. Shown in Table 15 are examples of the inhibitory effect of recombinantly produced anti-GPVI Fab fragments on GPVI collagen binding.

TABLE 15

Measured IC50 values (µg/ml) for the inhibition of collagen binding to GPVI of three independent experiments.

| Variant | Test 1 | Test 2 | Test 3 |
|---|---|---|---|
| Based on clone 390* | 0.49 | 0.56 | 0.99 |
| VL1/VH1 | 1.10 | 0.75 | 1.00 |
| VL1/VH2 | 1.17 | 0.82 | — |
| VL1/VH3 | 0.63 | 1.24 | 0.87 |
| VL1/VH4 | 1.01 | 1.14 | 1.06 |
| VL1/VH5 | 1.41 | 1.58 | 1.24 |
| VL2/VH2 | 0.81 | 0.73 | 1.05 |
| VL3/VH2 | 0.67 | 0.90 | 1.04 |
| VL3/VH4 | 0.72 | 0.72 | 1.02 |

*Note: This variant corresponds to a non-humanized construct based on the original clone 390 without the His-tag. Therefore this construct is exactly in the same format as the humanized variants (DKTHT at the C-terminus of HC) mentioned in the same table.

B. Inhibition of Collagen Induced Platelet Aggregation by Recombinant Anti-GPVI Fab Fragments (Human Platelet Rich Plasma)

For platelet rich plasma (PRP), blood was collected into syringes containing ACD-A to a final concentration of 10%. After centrifugation at 200×g for 20 min at room temperature without brake, supernatant (PRP) was separated. Platelet poor plasma (PPP) was separated from the remaining blood by centrifugation for 10 min at 1500×g. PRP was set to a platelet count of 3.0×108 cells/ml by dilution with PPP. Fab fragments were used at final concentration of 0.15-20 µg/ml and incubated with PRP for 5 min at 37° C. Thereafter collagen was added at a concentration of 1-1.5 µg/ml and the aggregation response was monitored by the measurement of light transmission by either using a 96well plate reader (96well plate aggregation) or Born aggregometer (classical aggregation). The aggregation response was monitored for 20 min. As shown in Table 16 all investigated Fab fragments were able to inhibit collagen induced platelet aggregation in a concentration dependent manner.

TABLE 16

Calculated IC50 values (µg/ml) for inhibition of collagen induced platelet aggregation of three independent experiments.

| Variant | Test 1 | Test 2 | Test 3 |
|---|---|---|---|
| Based on clone 390* | 1.6 | 6.4 | 1.3 |
| VL1/VH1 | 1.5 | 2.3 | — |
| VL1/VH2 | 2.3 | 2.0 | 1.1 |
| VL1/VH3 | 1.7 | 1.5 | 1.5 |
| VL1/VH4 | 1.6 | 1.8 | 1.2 |
| VL1/VH5 | 1.9 | 2.3 | 1.2 |
| VL2/VH2 | 1.4 | 2.4 | 2.3 |
| VL3/VH2 | 1.9 | 0.9 | 2.1 |
| VL3/VH4 | 1.0 | 2.3 | 2.0 |

*Note: This variant corresponds to a non-humanized construct based on the original clone 390 without the His-tag. Therefore this construct is exactly in the same format as the humanized variants (DKTHT at the C-terminus of HC) mentioned in the same table.

C. Inhibition of Collagen Induced Platelet Aggregation by Anti GPVI Fab Fragments (Human Whole Blood)

Figure 6:
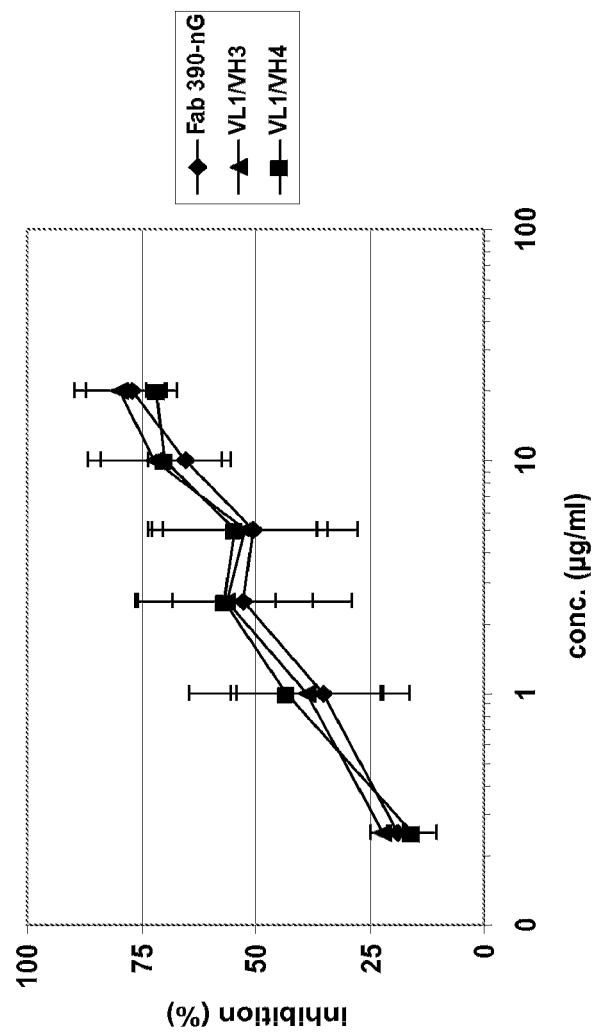
FIG. 6: Examples of IC50 curves for the inhibitory activity of anti-GPVI Fab-fragments in collagen induced whole blood aggregation.
Figure 7:
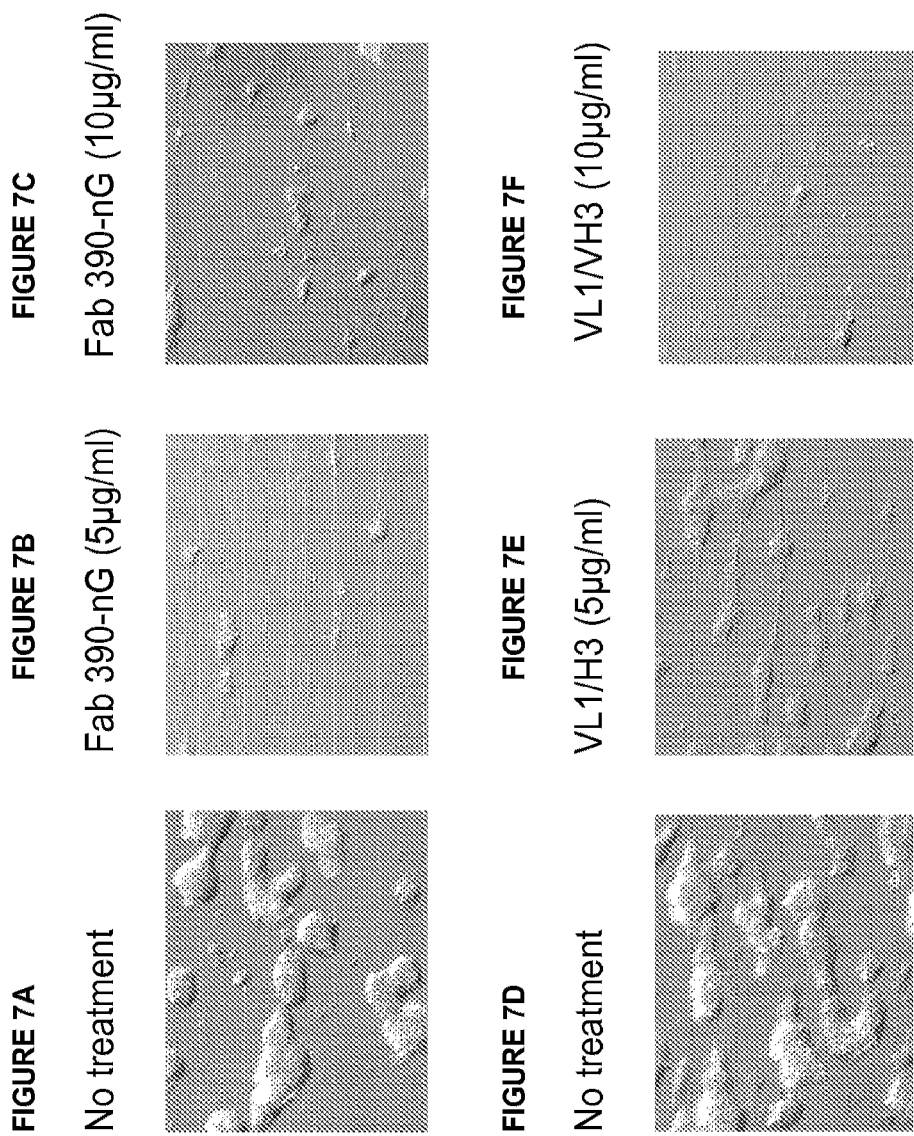
FIG. 7: Examples of inhibition of thrombus formation under flow by anti GPVI-Fab fragments.

For the experiments blood was anticoagulated with 20 µg/ml hirudin and used immediately. Before measurement whole blood was diluted 1:1 with NaCl. Fab fragments were used at final concentration of 0.15-20 µg/ml and incubated with blood for 5 min at 37° C. Thereafter collagen was added at a concentration of 1 µg/ml and the aggregation response was monitored by the measurement of the impedance using Multiplate® analyzer. The reaction was monitored for 6 min. The aggregation response was quantified by the area under the aggregation curve (AUC) as specified by the manufacturer. As shown in FIG. 6 investigated Fab fragments were able to inhibit collagen induced platelet aggregation in a concentration dependent manner.

D. Inhibition of Thrombus Formation Under Flow by Anti GPVI Fab Fragments

For the experiments blood was anticoagulated with 20 µg/ml hirudin and used immediately. Rectangular capillary glass microslides with an inner diameter of 1×0.1 mm (Camlab, Cambridge, UK) were coated overnight with 100 µg/ml Horm collagen and blocked with heat-inactivated 0.5% fatty acid-free BSA at room temperature for 1 h. Blood platelets were fluorescently labeled with 2 µM DiOC6(3) and treated with Fab fragments for 5 min at 37° C. Perfusion through the collagen coated coverslip was performed for 2 minutes at 2000 s-1. After blood perfusion, Tyrodes buffer 1 was perfused through the microslides for 5 min at the same shear rate. Thrombus formation was quantified by determination of platelet (thrombus) surface coverage. For this purpose ten final fluorescence images were recorded from different areas in the middle of the capillary. Additionally, phase contrast and DIC pictures were recorded. Imaging recording and analysis was performed using ImagePro plus imaging software (Mediacy, Silver Spring, USA) connected to a black-and-white CCD camera (CoolSnap cf, Ropers Scientific GmbH/Photometrics, Ottobrunn). FIG. 7A-E show examples of inhibition of thrombus formation under flow by anti GPVI-Fab fragments.

E. Effect of the Anti-GPVI Fab-Fragment in a Mouse Model of Arterial Thrombosis

For this in vivo investigation, mice humanized for the GPVI receptor have been used. The Carotid artery occlusion was photochemically induced resulting in vascular endothelial injury at the inner vessel side without affecting the outer vessel wall. By this technique the red dye, rose bengal, is systemically administered and the endothelium of the carotid artery was irradiated by green laser light resulting in an "inside-out" injury. The anti GPVI Fab-fragment was administered at 10 mg/kg as an intravenous bolus via the jugular vein catheter. After a 15 min incubation period the laser light source was placed 12 cm away from the carotid artery distal to the flow probe and laser irradiation was started. Blood flow was continuously monitored for an observation period of 90 min. The measured thrombosis parameters were the length of time to complete arterial occlusion following vascular injury (time to occlusion, TTO) and the area under the blood flow curve (AUC).

For thrombosis evaluation, two measured parameters were used: a) time to occlusion (TTO) and b) the area under the blood flow curve. The time from thrombotic challenge until vessel occlusion (TTO) was 78 min for anti-GPVI Fab fragment versus 33 min for the control group resulting in a 2.4-fold increase (table 17). The area under the flow curve was 2.3-fold increased for the group treated with anti-GPVI Fab fragment compared to the control group (table 18). Intravenous bolus administration of 10 mg/kg anti-GPVI Fab fragment resulted in a significant antithrombotic effect in the photochemical induced arterial thrombosis model in humanized GPVI mice.

TABLE 17

Thrombosis parameter: Time to occlusion (min)

| TTO (min) | Control group | Fab 10 mg/kg iv |
|---|---|---|
| Mean | 32.9 | 77.9 |
| SEM | 1.4 | 5.0 |
| Lower 95% CI of mean | 29.5 | 65.0 |
| Upper 95% CI of mean | 36.4 | 90.8 |
| Number of animals | 6 | 6 |

TABLE 18

Thrombosis parameter: Area under the blood flow curve

| AUC (au) | Control group | Fab 10 mg/kg iv |
|---|---|---|
| Mean | 1154 | 2605 |
| SEM | 189.2 | 515.2 |
| Lower 95% CI | 667.1 | 1280 |
| Upper 95% CI | 1640 | 3929 |
| Number of animals | 6 | 6 |

F. GPVI Depletion from the Platelet Surface Induced by Anti-GPVI Fab Fragments

For the experiments, blood was anticoagulated with 20 μg/ml hirudin and used immediately. Anti GPVI-Fab fragments were used at indicated concentrations. Blood or platelet rich plasma (PRP) samples were incubated with the Fab fragments for 5 min, 15 min, 1 h and 2 h, respectively. Thereafter samples were fixed using paraformaldehyde and GPVI receptor expression was determined. GPVI density on the platelet surface was measured using a different, fluorescently labelled anti-GPVI antibody and determined in a flow cytometer (BD LSR II). As a control, it was previously shown that this antibody is able to bind GPVI independently (and in the presence) of the investigated Fab fragment.

Figure 8:
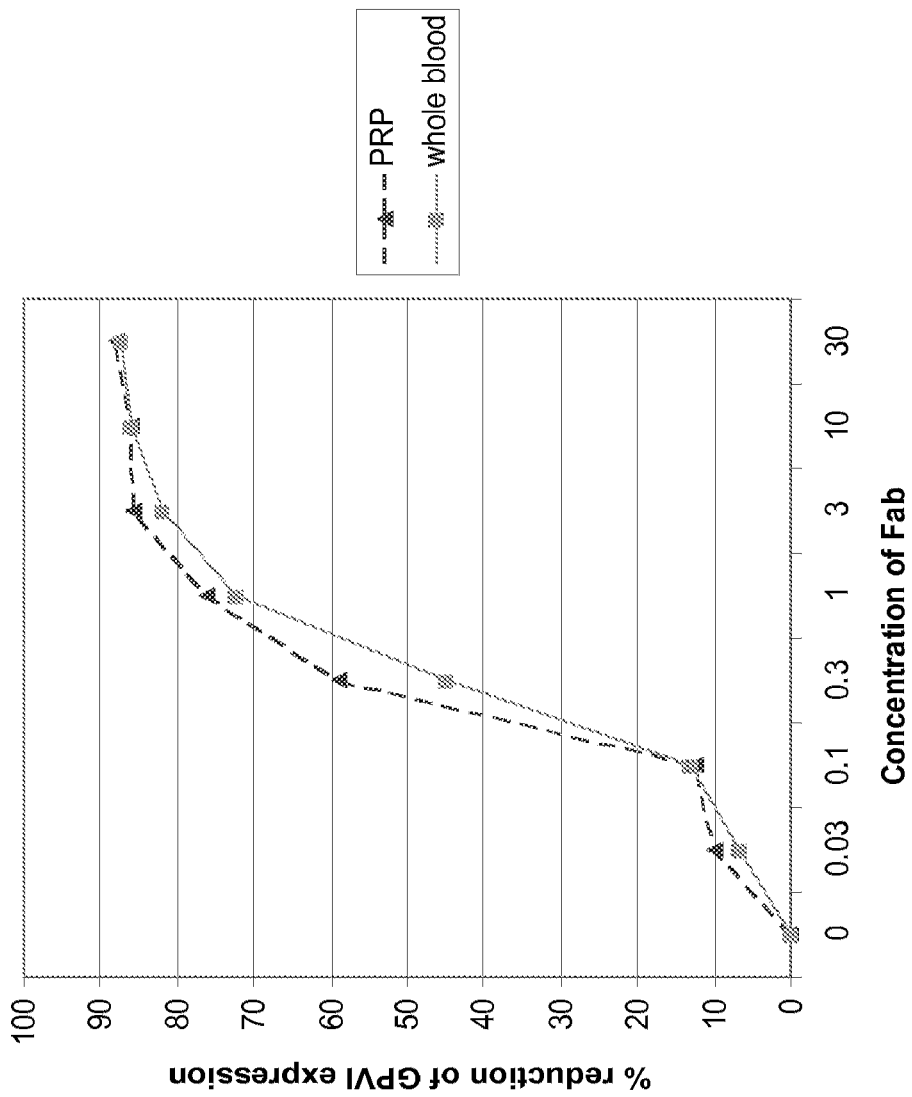
FIG. 8: Anti-GPVI Fab causes a reduction of GPVI surface expression in a concentration dependent manner.
Figure 9:
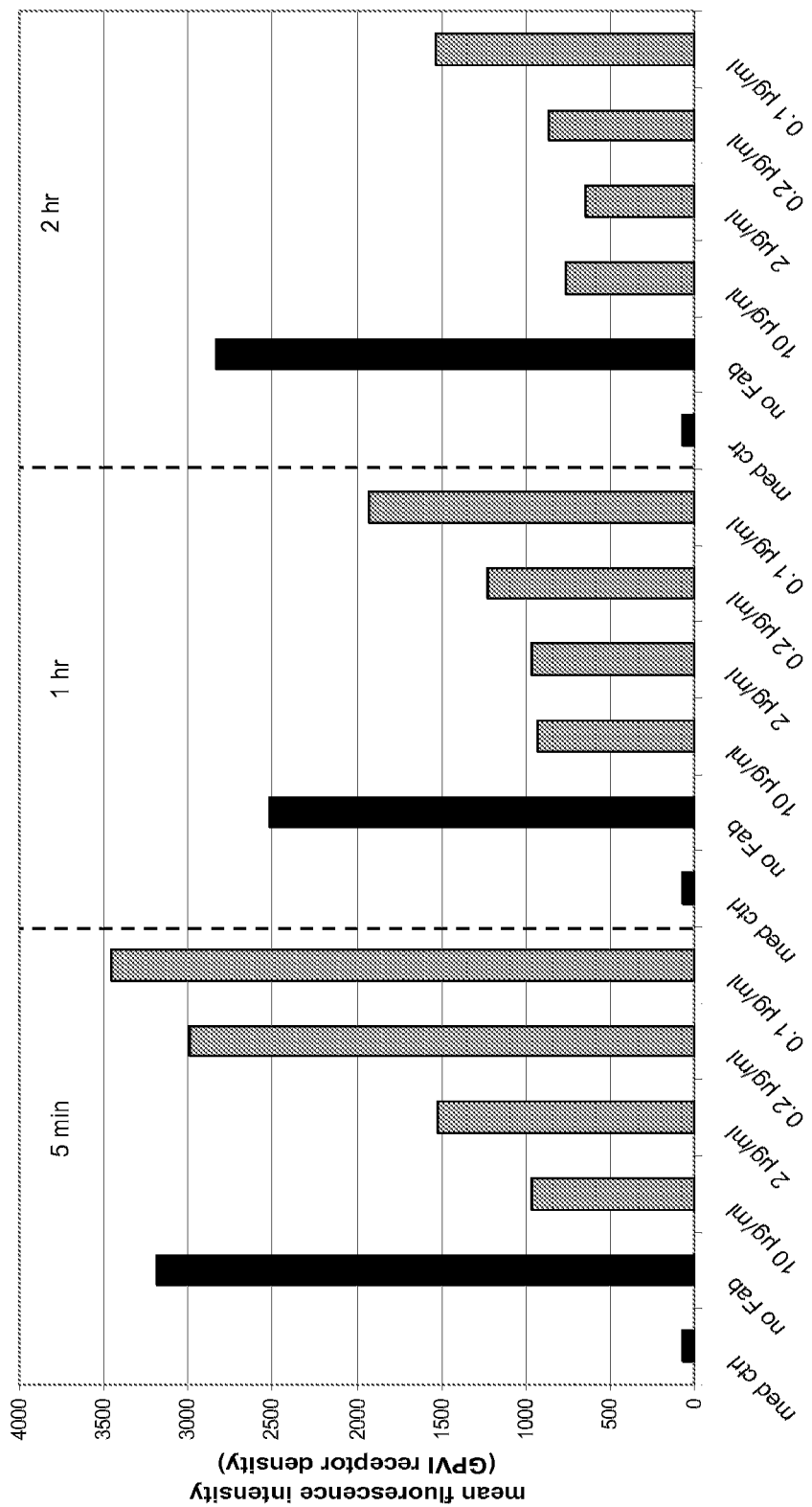
FIG. 9: Anti-GPVI Fab causes a significant GPVI depletion in a time dependent manner.

As shown in FIG. 8, the anti-GPVI Fab causes a reduction of GPVI surface expression in a concentration dependent manner. Further experiments show that 5 min of anti GPVI Fab exposure already caused a significant GPVI depletion at 10 μg/ml and 2 μg/m (FIG. 9). Also lower concentrations of the anti-GPVI Fab were able to decrease the GPVI surface density, although with a delayed time course.

These results support the fact that the anti-GP VI Fab induces the GP VI depletion at the platelet surface.

G. In Vitro and Ex Vivo Effect of an Anti GPVI Fab on Collagen-Induced Whole Blood Aggregation in Cynomolgus Monkey (*Macaca fascicularis*) with Concomitant Hematology Assessment.

1. Animal Details and Dose Regimen:

Animal studies were conducted in an AAALAC (Association for Assessment and Accreditation of Laboratory Animal Care)-accredited facility according to the local animal welfare regulations and registered by the veterinary authorities. The species/strain used in the study was cynomolgus monkeys (*Macaca fascicularis*). Only female monkeys were used for the study. Two animals per dose group were studied. Doses studied included phosphate buffered saline (PBS) vehicle control, 0.01, 0.1, 1, and 3 mg/kg of anti GPVI Fab all administered at 2 ml/kg IV bolus. The bodyweight of the included monkeys ranged between 3.52 and 7.34 kg. One of the animals (monkey D) used in the 1 mg/kg dose group did not show any platelet aggregation response at pre-dose sample. Hence, no calculation of intra-individual relative change of aggregation response (inhibition of aggregation in % compared to pre-dose) over time was possible and no data is provided.

2. Blood Sampling and Processing for Hematology and Plasma Preparation

Whole blood was collected from healthy conscious single-housed cynomolgus monkeys from the antecubital vein after needle puncture at various time intervals before and after drug or vehicle administration (pre-dose, 0.5, 1, 2, 4, 6, 8, 24, 48, 72, 149.5 hours) into tubes containing 3.13% sodium citrate (Eifelfango, Bad Neuenahr-Ahrweiler, Germany) at 1/10 of the total tube volume after blood sampling. From the PBS vehicle treated group the sampling schedule varied slightly and the following time points were sampled: pre-dose, 0.5, 1, 2, 4, 6, 8, 24, 48, 126 hours. Whole blood cell counts with a particular focus on platelet count were determined to monitor the physiological state of hematology by using an automated hematology analyzer Scil Vet abc (Scil animal care Company GmbH, Viernheim, Germany). The remaining blood sample after whole blood aggregation assays was centrifuged for plasma preparation from each time point. For plasma preparation blood was centrifuged at 5000 U/min for 15 min and the supernatant collected in a separate tube and frozen at −20° C. for analysis of plasma levels of anti GPVI Fab at a later time point.

3. Measurements of Whole Blood Platelet Aggregation

Whole blood platelet aggregation assays were performed using the Multiplate® platelet function analyzer (Dynabyte lnformationssysteme GmbH, Munich, Germany). The agonist used was equine type I collagen (Horm collagen, Nycomed, Munich, Germany) at a final concentration of 1 μg/ml. The analysis was performed according to the manufactures instruction and percent inhibition of whole blood aggregation was calculated relative to each individual whole blood aggregation response at pre-dose. Briefly described, the cartridge was preloaded with 297 μl $CaCl_2$ and 297 μl of whole blood was added. After five minutes of equilibration 6 μL of the agonist collagen was added in a 100-fold concentration and the measurement started. The recording took place for 7 min and the result was expressed as area under the curve (AUC, arbitrary unit) over time in minutes. Relative change of AUC over time compared to the pre-dose value was calculated to percent inhibition of platelet aggregation and plotted in a graph.

With a separate set of blood samples from other monkeys out of the same colony in vitro dose-response measurements were performed to determine an in vitro $IC_{50}$ for the anti GPVI Fab. Therefore blood samples were handled in the same way as described above for ex vivo measurement. Briefly, different concentrations of anti GPVI Fab (30, 10, 3, 1, 0.3, 0.1, 0.03, 0.01 μg/ml) were added to the $CaCl_2$/whole blood mixture in the test cell of the Multiplate® analyzer and incubated for 5 minutes. After adding the agonist collagen at 1 μg/ml the measurement was started and the AUC recorded for 7 min. By plotting the respective dose-response an $IC_{50}$ was calculated using an in-house statistical software tool (Speed 2.0 LTS).

4. Measurement of GPVI Receptor Surface Expression

Whole blood was collected from healthy conscious single-housed cynomolgus monkeys from the antecubital vein after needle puncture at various time intervals before and after drug or vehicle administration into tubes containing 3.13% sodium citrate at 1/10 of the total tube volume after blood sampling and used immediately. Samples were fixed using 5% paraformaldehyde and GPVI receptor expression was determined. GPVI density on the platelet surface was measured using a different, fluorescently labelled anti-GPVI antibody and determined in a flow cytometer. As a control, it was previously shown that this antibody is able to bind GPVI independently (and in the presence) of the investigated Fab fragment.

5. Results on Whole Blood Platelet Aggregation.

Figure 10A:
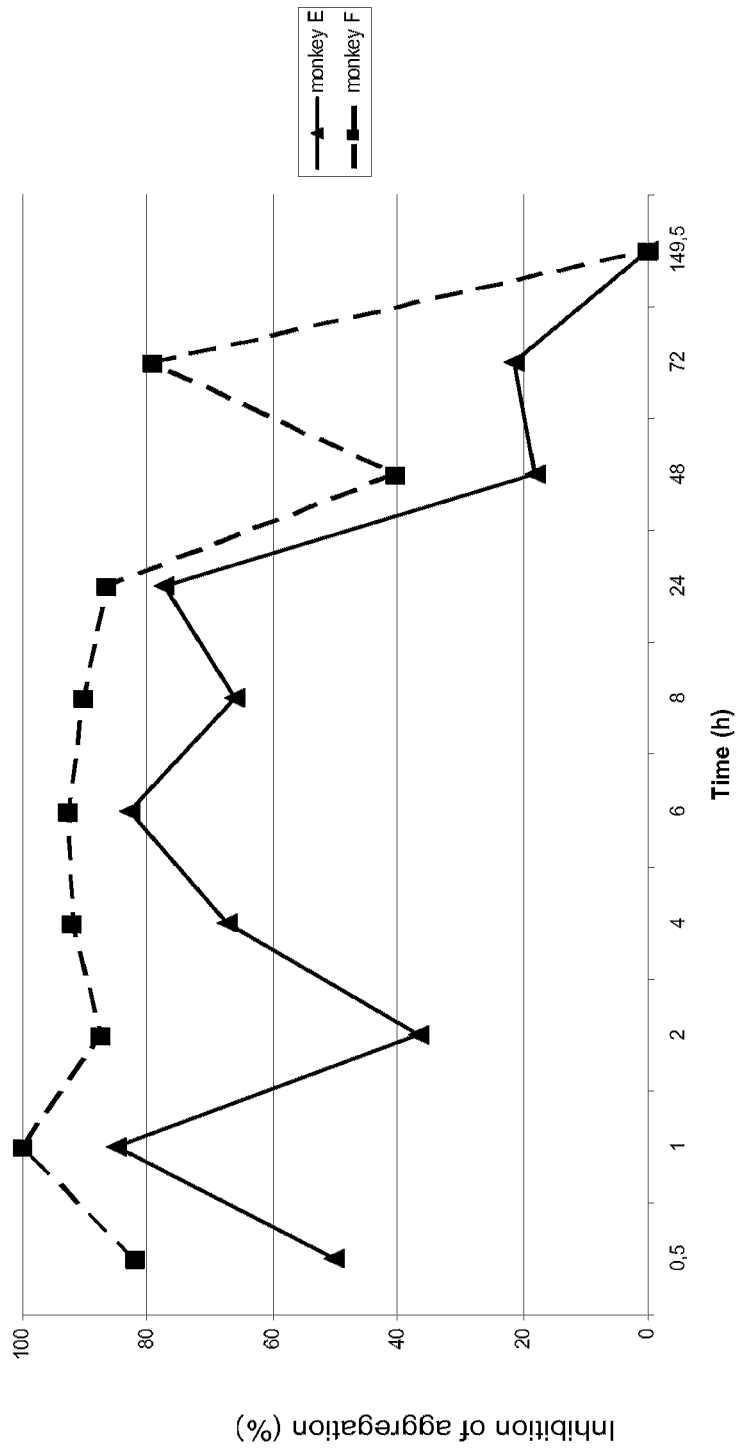
FIG. 10: Effect of anti-GPVI Fab on ex vivo whole blood platelet aggregation (agonist: 1 µg/ml). A—after 1 mg/kg IV bolus administration. B—after 3 mg/kg IV bolus administration.
Figure 10B:
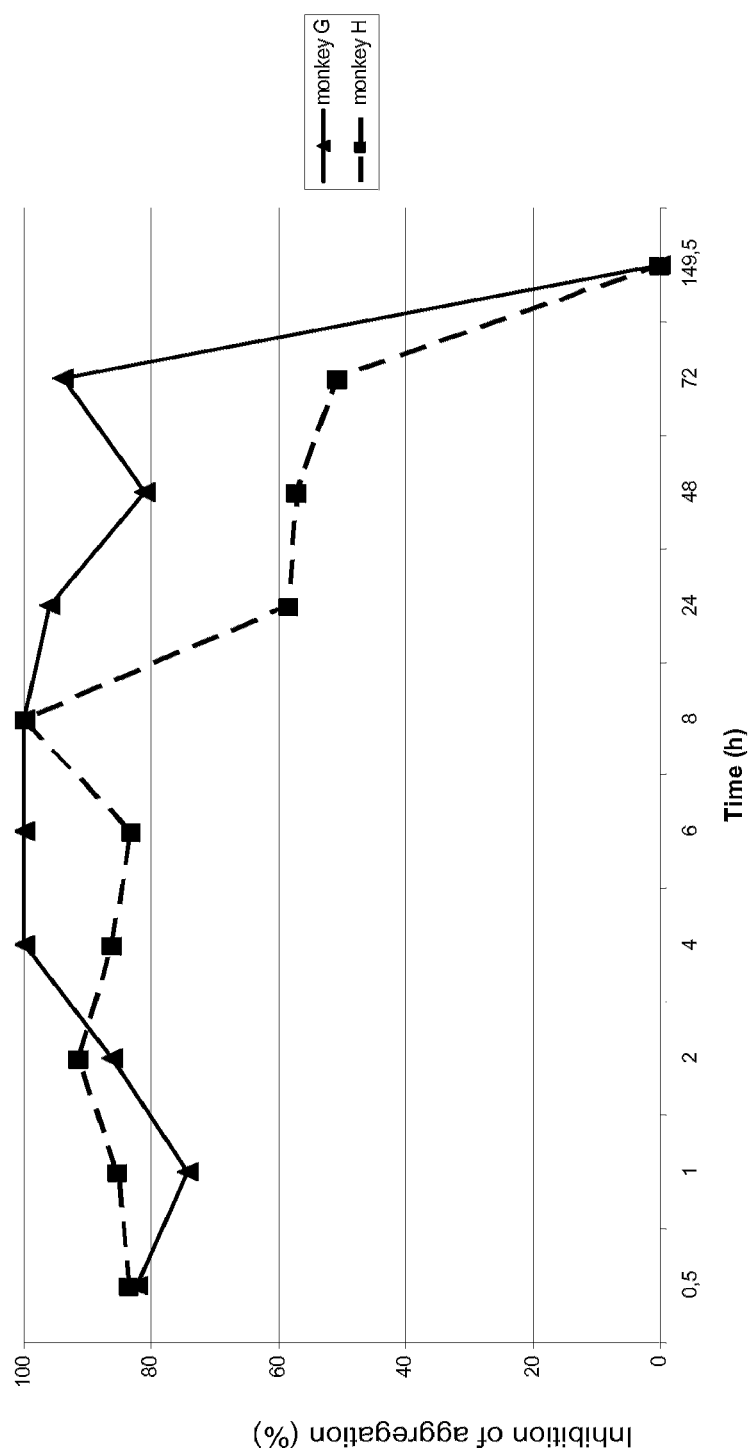

To compare the respective dose regimen, percent inhibition of whole blood platelet aggregation is calculated relative to the pre-dose value of each individual animal. The PBS vehicle group revealed up to 67% of inhibition of platelet aggregation at 6 hours after IV bolus administration (data not shown). Therefore, at least 80% inhibition of platelet aggregation over at least two consecutive time points was considered to be physiologically relevant. Both two low doses of anti GPVI Fab tested (0.01 and 0.1 mg/kg anti GPVI fab) did not show any relevant inhibition of whole blood aggregation. At 1 mg/kg, 93% platelet inhibition was reached already at 1 hour after administration and stayed above 80% up to 24 hours (apart from a slight decrease in effect at 2 FIG. 10 A). Inhibition of platelet function subsequently decreased over time. At 3 mg/kg the inhibition of platelet aggregation was stable at greater values than 80% during the first 24 hours of observation and sustained until 72 hours with values between 69% and 77% (FIG. 10 B). In both higher dose groups tested the platelet function fully recovered at the last time point (149.5 hrs, FIGS. 10 A and B). Based on this data an $ED_{50}$ was estimated at 0.5 hours post IV bolus administration and revealed 0.5 mg/kg for the tested anti GPVI Fab.

This experiment demonstrates that anti GPVI Fab inhibit ex vivo whole blood platelet aggregation in a dose-dependent manner when compared to vehicle using collagen (1 μg/ml).

Figure 11:
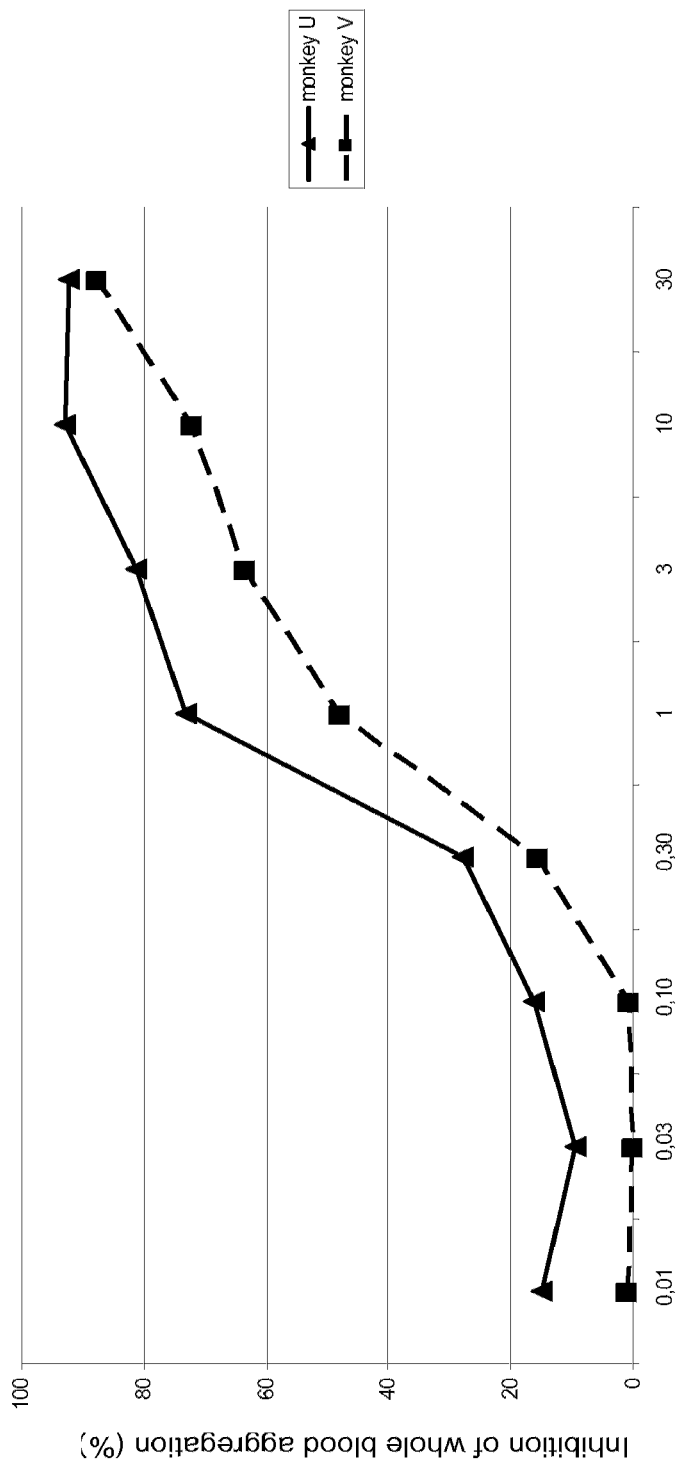
FIG. 11: In vitro activity of anti-GPVI Fab in whole blood platelet aggregation assay (agonist: 1 µg/ml)
Figure 12A:
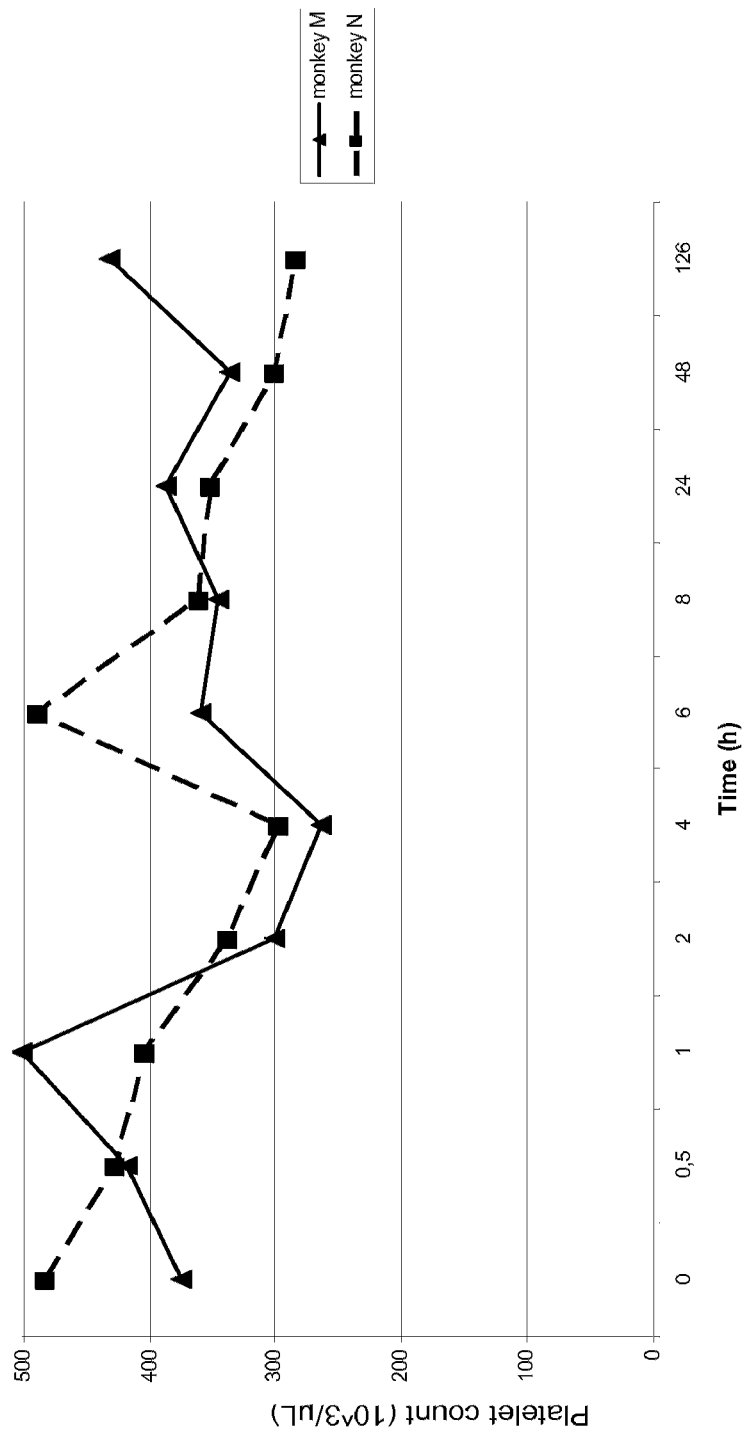
FIG. 12: Effect IV bolus administration of anti-GPVI Fab on platelet count. A—After PBS vehicle at 3 ml/kg (control). B—After 0.01 mg/kg of anti-GPVI FAb. C—After 0.1 mg/kg of anti-GPVI FAb. D—After 1 mg/kg of anti-GPVI FAb. E—After 3 mg/kg of anti-GPVI FAb.
Figure 12C:
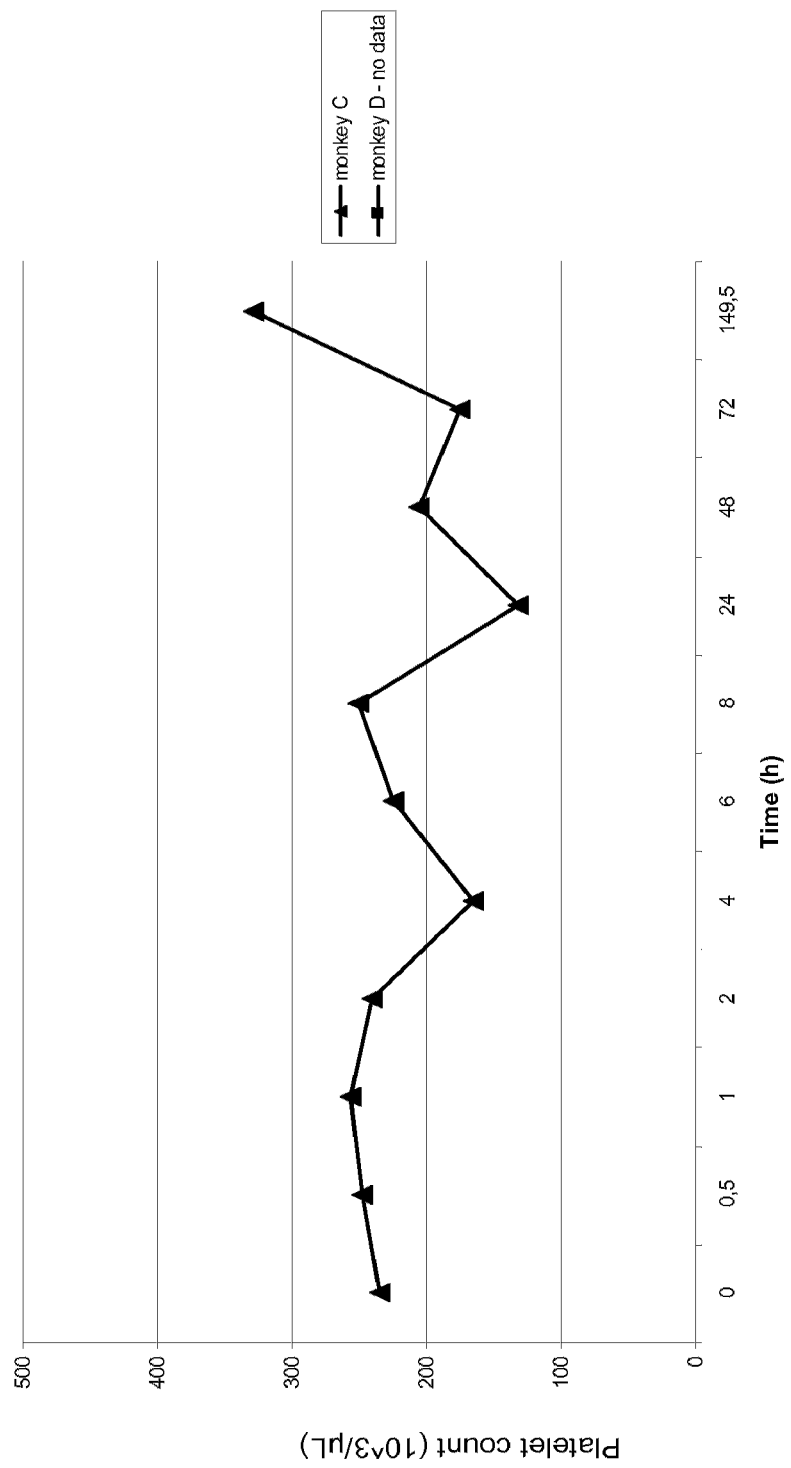
Figure 12D:
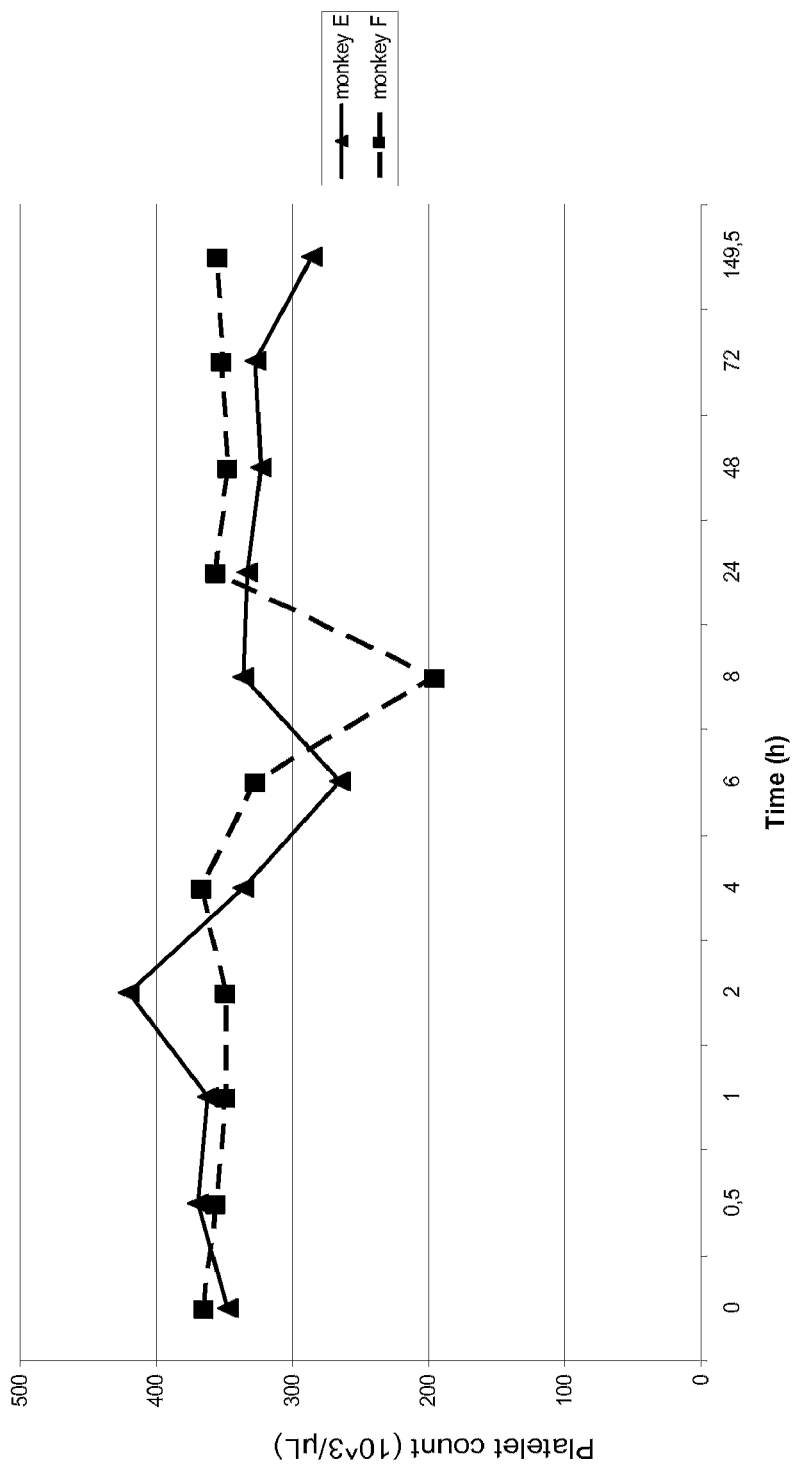
Figure 12E:
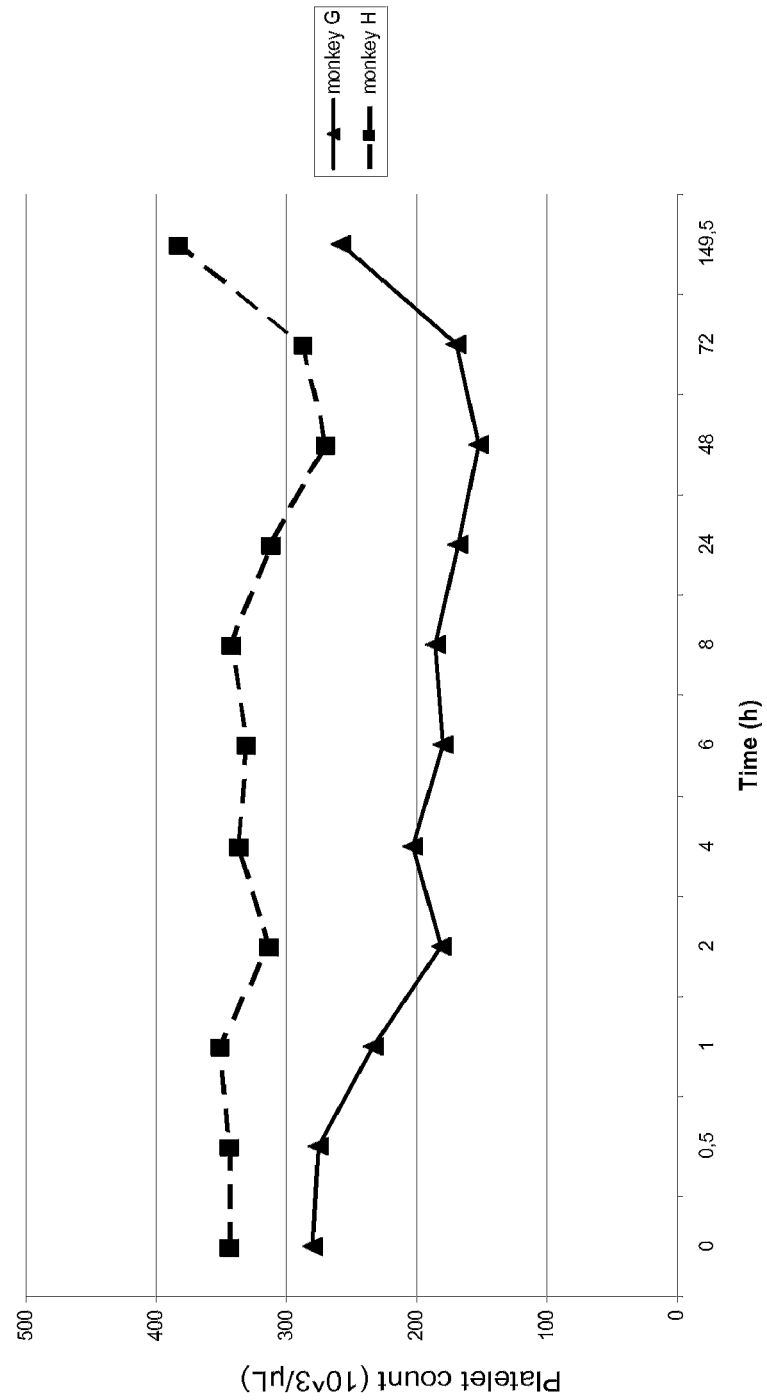
Figure 13B:
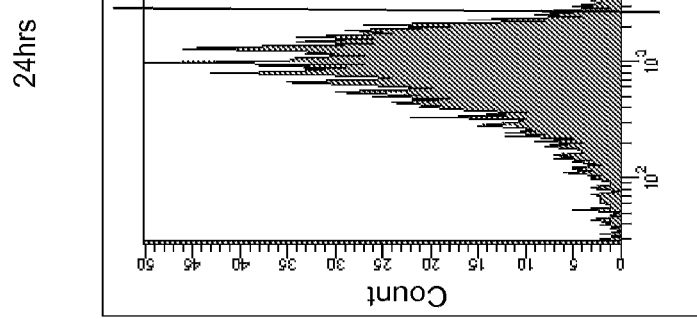
FIG. 13: FACS analysis of GPVI receptor expression on platelets after iv administration of anti-GPVI Fab. The vertical line descriminates between GPVI negatives platelets on the left side and GPVI positive platelets on the right side. A—pre-dose. B—at 24 h after administration. C—at 48 h after administration. D—at 72 h after administration. E—at 150 h after administration.
Figure 13A:
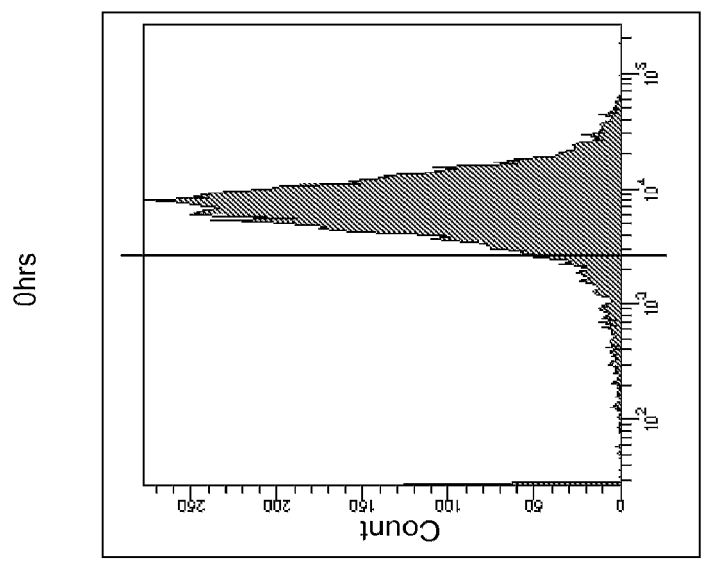
Figure 13C:
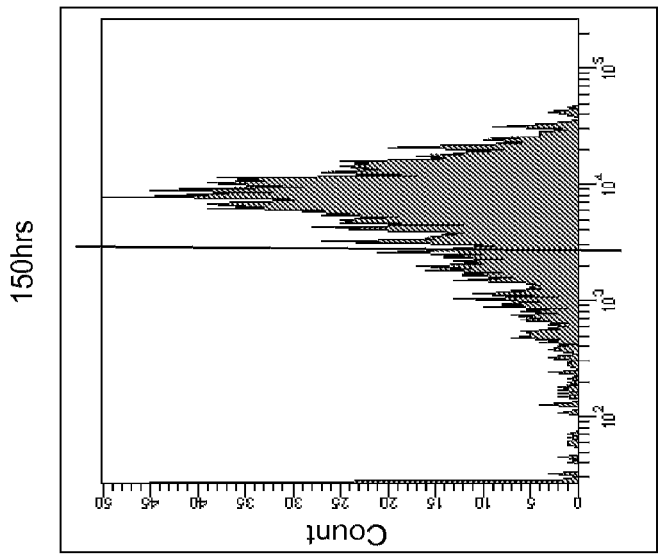
Figure 13D:
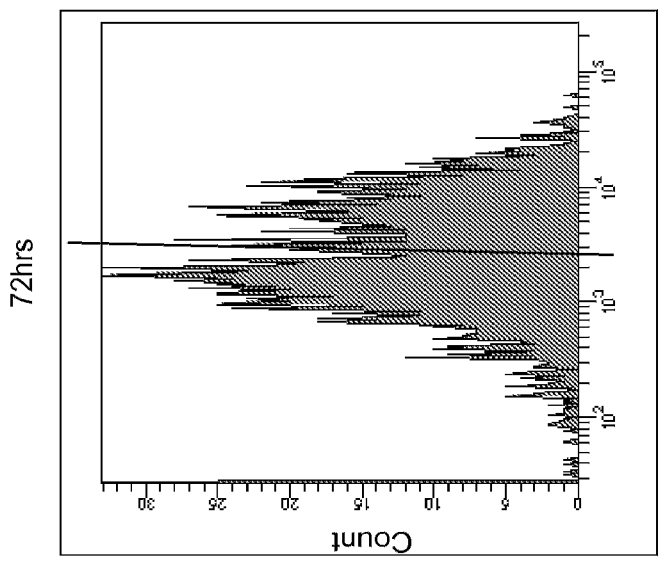
Figure 13E:
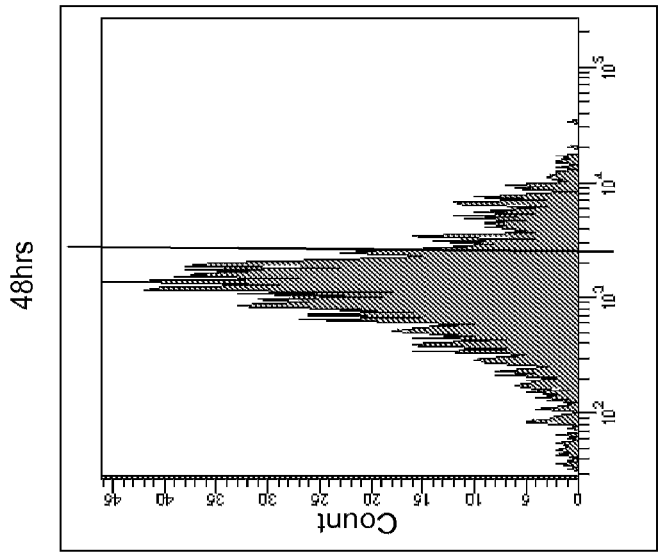

In a separate set of experiments the in vitro activity of the anti GPVI Fab was determined. The calculated $IC_{50}$ revealed 0.81 μg/ml [0.51; 1.28 μg/ml] CV=21.6% (FIG. 11).

6. Hematology Assessment

To monitor the physiological state of hematology during the time-course of the experiment, whole blood cell counts with a particular focus on platelet count were determined. Mean platelet counts at pre-dose varied between $428\times10^3/\mu L$ in PBS vehicle, $369\times10^3/\mu L$ at 0.01 mg/kg anti GPVI Fab, $235\times10^3/\mu L$ at 0.1 mg/kg anti GPVI Fab, $357\times10^3/\mu L$ at 1 mg/kg anti GPVI Fab, and $312\times10^3/\mu L$ at 3 mg/kg anti GPVI Fab (FIG. 12 A-E). During the time-course of the experiment the platelet count did not change substantially (i.e. values below $100\times10^3/\mu L$) and the following platelet count was determined at 126 hours in the PBS vehicle group: $358\times10^3/\mu L$ (FIG. 12 A). In all anti GPVI Fab treated groups the platelet count determined at 149.5 hours revealed the following values: $411\times10^3/\mu L$ at 0.01 mg/kg anti GPVI Fab, $329\times10^3/\mu L$ at 0.1 mg/kg anti GPVI Fab, $321\times10^3/\mu L$ at 1 mg/kg anti GPVI Fab, and $320\times10^3/\mu L$ at 3 mg/kg anti GPVI Fab (FIG. 12 B-E). All other determined hematology parameters, hematocrit, red blood cell count, and hemoglobin were not changed substantially during the time-course of the experiment (data not shown).

These data demonstate that the GPVI Fab do not affect the physiological state of hematology.

7. GPVI Receptor Expression

As shown in FIG. 13, before iv administration of the anti GPVI Fab all platelets were positive for GPVI expression (pre-dose). In blood taken after drug administration no specific signal for GPVI could be observed on the platelet surfaces (24 h). Beginning at 48 h after drug administration a new population of platelets arises, which are GPVI positive. 150 h after drug administration all platelet were again positive for GPVI receptor expression.

This experiment confirms that GPVI Fabs induce GPVI receptor depletion on platelet and that this effect was reversible.

Example 5

Modification of Fab Fragments Properties by Recognition by Auto-Antibodies

A—Determination of the Activatory Component in Donor Plasma

To investigate the importance of IgG's present in plasma for the activatory effect of the anti-GPVI Fab, 51 different blood samples were tested. Samples which have been identified as activatory were depleted of IgG's using protein A.

For the experiments, blood was anticoagulated with 20 μg/ml hirudin and used immediately for the preparation of plasma (centrifugation of blood samples for 10 min at 1600 g). Thereafter, plasma was depleted of IgG's for 2 h at 4° C. using protein A. Protein A was removed by centrifugation and platelets were added at a final concentration of 2×10E8/ml. Anti GPVI-Fab fragments were used at 20 μg/ml. Plasma samples were incubated with the Fab fragments or convulxin (or "cvx", a GP VI specific agonist) for 15 min followed by a staining with the FITC labelled Pac-1 antibody (specific for activated GPIIbIIIa, which is a platelet activation marker) for 30 min. Thereafter, samples were fixed using paraformaldehyde and Pac-1 labelling of platelet was determined in a flow cytometer (BD LSR II).

Figure 14:
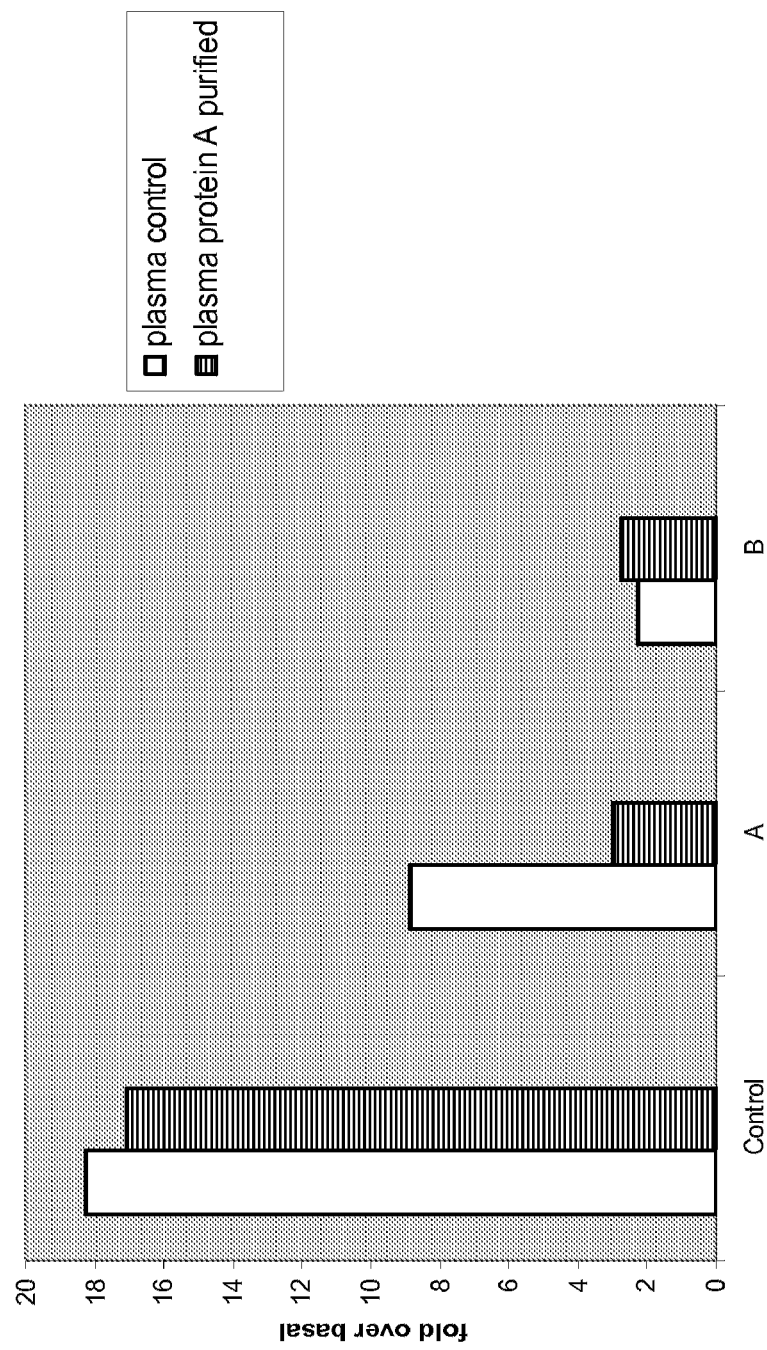
FIG. 14: Effect of anti-GPVI Fab on platelet activation. In control panel, addition of convulxin. In panel A, addition of Fab after IgG depletion. In panel B, addition of modified Fab.

As seen in FIG. 14, on Control panel, treatment of plasma with protein A had no effect on platelet activation by the GPVI specific agonist convulxin (cvx). However, FIG. 14, panel A shows that the activatory effect of Fab was greatly reduced after IgG depletion, suggesting that preformed IgG's are an essential component for this response.

B—Determination of the Expression of Platelet Activation Markers Following Modified Anti GPVI-Fab Fragment Exposer To further investigate the role of plama IgG on activation of platelet activation through Fab, the different Fab fragments were used which were identical in their heavy and light chain (HC and LC) sequence but differ in their C-terminal modification on the heavy chain.

The four different molecules used are described below and illustrated in FIG. 15.

Figure 15:
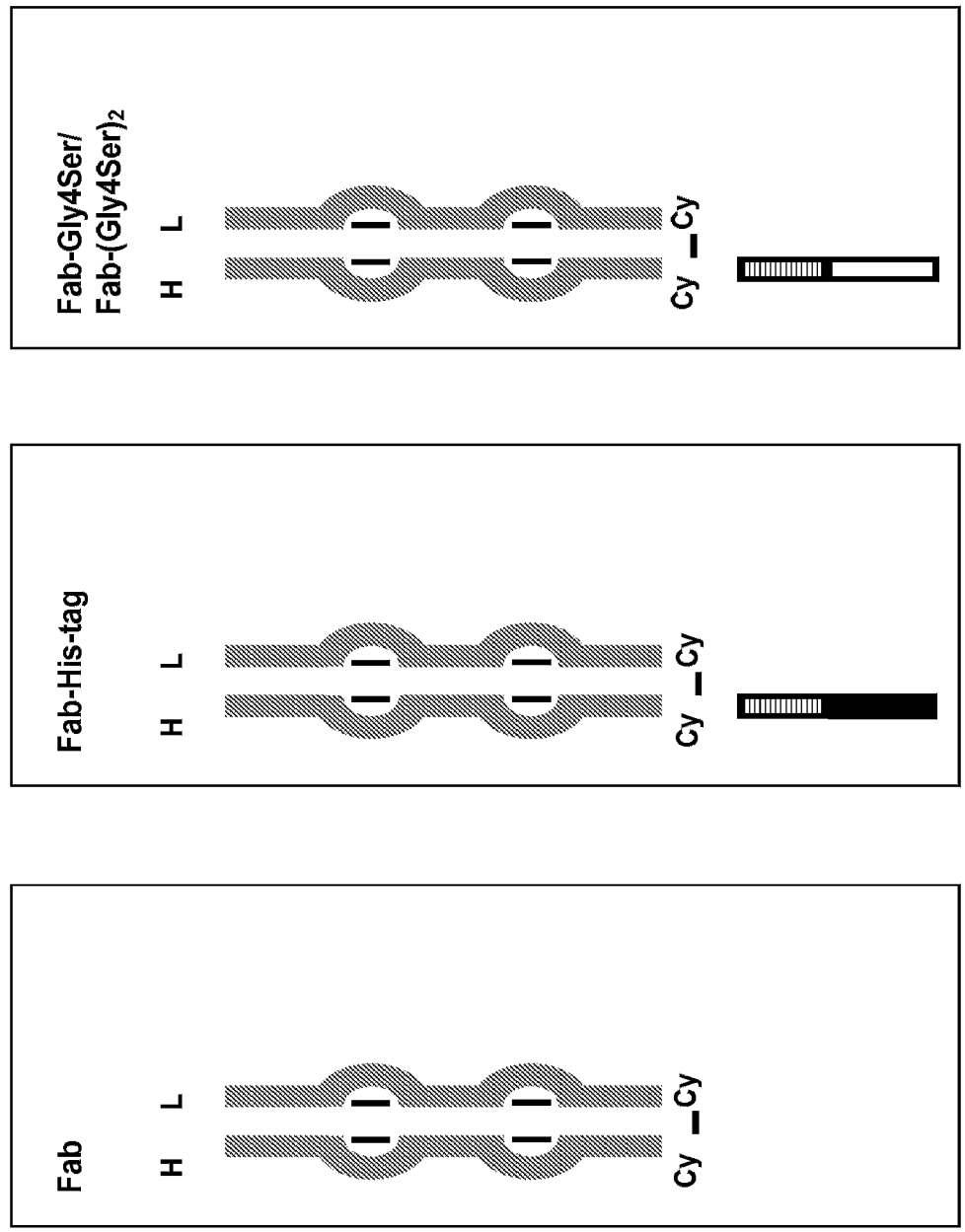
FIG. 15: A—Fab control; B—Fab-His-Tag; C—FabGly4Ser and Fab-(Gly4Ser)2

Fab: control molecule with no C-terminal additional amino acids on HC (FIG. 15 A)

Fab-His-tag: hasHisHisHisHisHis peptide sequence (SEQ ID NO:35) on HC corresponding to the natural occurring sequence plus C-terminal His-tag (FIG. 15 B)

Fab-Gly4Ser: has a GlyGlyGlyGlySer peptide sequence (SEQ ID NO:36) on HC corresponding to the natural occurring sequence plus C-terminal Gly4Ser-tag (FIG. 15 C)

Fab-(Gly4Ser)2: has a GlyGlyGlyGlySerGlyGlyGlyGlySer peptide sequence (SEQ ID NO:36) on HC corresponding to the natural occurring sequence plus C-terminal (Gly4Ser)2-tag (FIG. 15 C)

As illustrated in FIG. 14, panel B, the modified Fab do not induce any activatory, even without IgG depletion, suggesting that modified Fab are not recognized by preformed IgG's.

For the experiments, blood was anticoagulated with 20 μg/ml hirudin and used immediately. Anti GPVI-Fab fragments were used at 20 μg/ml. Blood samples (1-51) were incubated with the Fab fragments for 15 min followed by a staining with the FITC labelled Pac-1 antibody (specific for activated GPIIbIIIa, which is platelet activation marker) for 30 min. Thereafter samples were fixed using paraformaldehyde and Pac-1 labelling of platelet was determined in a flow cytometer (BD LSR II).

The activatory potential of the 4 Fab formats was tested on 51 different blood samples. Fab with no overhang induced a significant increase in Pac-1 binding (defined as >5 fold in 23 samples (corresponds to 42%). In sharp contrast, as seen in Table 19 below, Fabs modified at the C-terminus of the HC were much less active in this test with Fab-His-tag and Fab-Gly4Ser only showing activity on 1 sample and Fab-(Gly4Ser)2 (longest C-terminal extension) was not active over the threshold. This differential activatory pattern is also reflected in the cases of minor activation (2-5 fold over basal). These results indicated that the activatory potential of Fab fragments in this assay is not determined by the antigen binding CDR sequences but appears to reside in the HC C-terminus because the activity greatly reduced by C-terminal modifications of the HC chain. Thus these results suggest that the C-terminal extremity of Fab were recognized by IgG preexisting in patients blood, which induces platelet activation.

TABLE 19

Fold increase in Pac-1 binding to platelets incubated with Fab fragments with no overhang, Fab-His-tag, Fab-Gly4Ser and Fab-(Gly4Ser)2. 51 different samples (donors) were investigated. Grey field represent sample with activation over 5 fold basal values.

| Sample No. | Fab with no overhang | Fab-His-tag | Fab-Gly4Ser | Fab-(Gly4Ser)2 |
|---|---|---|---|---|
| 1 | 42.8 | 0.8 | 18.8 | 1.0 |
| 2 | 7.0 | 1.1 | 0.9 | 1.2 |
| 3 | 9.1 | 1.2 | 1.1 | 0.8 |
| 4 | 33.2 | 1.2 | 1.3 | 1.4 |
| 5 | 7.5 | 3.0 | 2.5 | 1.8 |
| 6 | 7.2 | 0.7 | 0.7 | 0.7 |
| 7 | 1.1 | 1.1 | 1.1 | 1.2 |
| 8 | 1.3 | 1.3 | 1.1 | 1.1 |
| 9 | 1.1 | 0.8 | 0.9 | 0.9 |
| 10 | 1.3 | 1.1 | 1.1 | 0.9 |
| 11 | 1.7 | 1.4 | 1.2 | 2.0 |
| 12 | 1.4 | 0.9 | 0.9 | 0.9 |
| 13 | 164.3 | 2.3 | 1.8 | 2.3 |
| 14 | 1.1 | 1.0 | 1.0 | 1.0 |
| 15 | 13.5 | 1.1 | 1.1 | 1.1 |
| 16 | 24.1 | 1.3 | 1.0 | 0.9 |
| 17 | 6.0 | 2.0 | 1.8 | 1.5 |
| 18 | 8.7 | 1.4 | 1.5 | 1.2 |
| 19 | 2.9 | 0.9 | 0.9 | 0.9 |
| 20 | 0.9 | 0.9 | 0.9 | 0.9 |
| 21 | 1.4 | 1.0 | 1.0 | 1.1 |
| 22 | 2.0 | 0.8 | 0.8 | 0.8 |
| 23 | 3.4 | 0.8 | 0.9 | 0.9 |
| 24 | 3.1 | 1.2 | 1.0 | 1.2 |
| 25 | 147.6 | 2.2 | 2.0 | 1.2 |
| 26 | 36.9 | 1.1 | 1.1 | 1.2 |
| 27 | 1.9 | 0.8 | 0.9 | 0.9 |
| 28 | 2.8 | 1.1 | 1.0 | 0.9 |
| 29 | 1.5 | 0.9 | 1.2 | 1.3 |
| 30 | 2.7 | 1.1 | 1.1 | 0.9 |
| 31 | 75.3 | 1.0 | 1.0 | 1.0 |
| 32 | 12.0 | 1.7 | 2.0 | 0.7 |
| 33 | 1.4 | 0.8 | 0.9 | 0.9 |
| 34 | 113.3 | 0.9 | 0.9 | 0.8 |
| 35 | 1.9 | 0.9 | 0.8 | 1.1 |
| 36 | 31.9 | 1.0 | 0.9 | 0.9 |
| 37 | 8.5 | 17.4 | 1.0 | 1.1 |
| 38 | 4.2 | 1.0 | 0.9 | 1.1 |
| 39 | 0.7 | 0.6 | 0.7 | 0.5 |
| 40 | 1.3 | 0.9 | 0.9 | 1.1 |
| 41 | 1.2 | 1.0 | 0.9 | 1.0 |
| 42 | 1.2 | 1.0 | 1.1 | 1.2 |
| 43 | 3.7 | 0.9 | 0.9 | 0.7 |
| 44 | 1.5 | 1.3 | 1.4 | 1.2 |
| 45 | 5.9 | 1.3 | 1.2 | 1.1 |
| 46 | 60.4 | 3.8 | 3.0 | 3.1 |
| 47 | 0.9 | 0.8 | 0.8 | 0.8 |
| 48 | 30.3 | 1.1 | 1.0 | 1.0 |
| 49 | 38.0 | 1.9 | 2.0 | 2.0 |
| 50 | 14.3 | 1.3 | 1.4 | 1.4 |
| 51 | 0.9 | 1.0 | 0.9 | 0.9 |

The invention claimed is:

1. A method for preventing recognition of a therapeutic antibody Fab fragment by pre-existing anti-Fab antibodies comprising attaching a molecule to the c-terminus of the Fab fragment that masks a Fab-specific neoepitope at the c-terminus of the Fab fragment without interfering with the binding of the antibody Fab fragment to its target, thereby preventing recognition of the Fab-specific neoepitope by the pre-existing anti-Fab antibodies and preventing platelet activation and associated side effects, wherein the antibody Fab fragment is an antibody Fab fragment that specifically binds to human platelet membrane protein Glycoprotein VI (GPVI) and induces a GPVI depletion phenotype, wherein the antibody Fab fragment binds to a conformational epitope of human GPVI and contacts human GPVI amino acid residues Ser 43, Arg 67, and Asp 81.

2. The method of claim 1, wherein the Fab fragment comprises:

(a) complementarity determining regions (CDRs) of a heavy chain variable region (HCVR) having the amino acid sequences of SEQ ID NO: 18, SEQ ID NO: 19, and SEQ ID NO: 20; and (b) complementarity determining regions (CDRs) of a light chain variable region (LCVR) having the amino acid sequences of SEQ ID NO: 21, SEQ ID NO: 22, and SEQ ID NO: 23; and wherein at least 2 amino acid residues of each CDR can be changed to other amino acid residues without directly disrupting contact with a GPVI epitope residue.

3. The method of claim 1, wherein the antibody Fab fragment comprises a heavy chain comprising the amino acid sequence of SEQ ID NO.6 and a light chain comprising the amino acid sequence of SEQ ID NO.8, or sequences having at least 80% identity with the amino acid sequence of SEQ ID NO: 6 or SEQ ID NO: 8, as long as the antibody Fab fragment binding specificity is maintained.

4. The method of claim 1, wherein the Fab fragment comprises a combination of a heavy chain variable region (HCVR) amino acid sequence and a light chain variable region (LCVR) amino acid sequence selected from the group consisting of:

(a) LCVR (SEQ ID NO.15) and HCVR (SEQ ID NO.10);

(b) LCVR (SEQ ID NO.15) and HCVR (SEQ ID NO.11);

(c) LCVR (SEQ ID NO.15) and HCVR (SEQ ID NO.12);

(d) LCVR (SEQ ID NO.15) and HCVR (SEQ ID NO.13);

(e) LCVR (SEQ ID NO.15) and HCVR (SEQ ID NO.14);

(f) LCVR (SEQ ID NO.16) and HCVR (SEQ ID NO.11);

(g) LCVR (SEQ ID NO.17) and HCVR (SEQ ID NO.11); and (h) LCVR (SEQ ID NO.17) and HCVR (SEQ ID NO.13).

5. The method of claim 1, wherein the molecule which is attached to the c-terminus of the Fab fragment is a peptide comprising an amino acid sequence selected from the group consisting of GlyGlyGlyGlySer (SEQ ID NO:36) and (GlyGlyGlyGlySer)2 (SEQ ID NO:37).

6. The method of claim 2, wherein the molecule which is attached to the c-terminus of the Fab fragment is a peptide comprising an amino acid sequence selected from the group consisting of GlyGlyGlyGlySer (SEQ ID NO:36) and (GlyGlyGlyGlySer)2 (SEQ ID NO:37).

7. The method of claim 3, wherein the molecule which is attached to the c-terminus of the Fab fragment is a peptide comprising an amino acid sequence selected from the group consisting of GlyGlyGlyGlySer (SEQ ID NO:36) and (GlyGlyGlyGlySer)2 (SEQ ID NO:37).

8. The method of claim 4, wherein the molecule which is attached to the c-terminus of the Fab fragment is a peptide comprising an amino acid sequence selected from the group consisting of GlyGlyGlyGlySer (SEQ ID NO:36) and (GlyGlyGlyGlySer)2 (SEQ ID NO:37).

* * * * *

SEQUENCE LISTING

<160> NUMBER OF SEQ ID NOS: 39

<210> SEQ ID NO 1
<211> LENGTH: 1337
<212> TYPE: DNA
<213> ORGANISM: Homo sapiens

```
<220> FEATURE:
<221> NAME/KEY: CDS
<222> LOCATION: (1)..(1329)

<400> SEQUENCE: 1 atg tct cca tcc ccg acc gcc ctc ttc tgt ctt ggg ctg tgt ctg ggg      48
Met Ser Pro Ser Pro Thr Ala Leu Phe Cys Leu Gly Leu Cys Leu Gly
1               5                   10                  15 cgt gtg cca gcg cag agt gga ccg ctc ccc aag ccc tcc ctc cag gct      96
Arg Val Pro Ala Gln Ser Gly Pro Leu Pro Lys Pro Ser Leu Gln Ala
            20                  25                  30 ctg ccc agc tcc ctg gtg ccc ctg gag aag cca gtg acc ctc cgg tgc     144
Leu Pro Ser Ser Leu Val Pro Leu Glu Lys Pro Val Thr Leu Arg Cys
        35                  40                  45 cag gga cct ccg ggc gtg gac ctg tac cgc ctg gag aag ctg agt tcc     192
Gln Gly Pro Pro Gly Val Asp Leu Tyr Arg Leu Glu Lys Leu Ser Ser
50                  55                  60 agc agg tac cag gat cag gca gtc ctc ttc atc ccg gcc atg aag aga     240
Ser Arg Tyr Gln Asp Gln Ala Val Leu Phe Ile Pro Ala Met Lys Arg
65                  70                  75                  80 agt ctg gct gga cgc tac cgc tgc tcc tac cag aac gga agc ctc tgg     288
Ser Leu Ala Gly Arg Tyr Arg Cys Ser Tyr Gln Asn Gly Ser Leu Trp
                85                  90                  95 tcc ctg ccc agc gac cag ctg gag ctc gtt gcc acg gga gtt ttt gcc     336
Ser Leu Pro Ser Asp Gln Leu Glu Leu Val Ala Thr Gly Val Phe Ala
            100                 105                 110 aaa ccc tcg ctc tca gcc cag ccc ggc ccg gcg gtg tcg tca gga ggg     384
Lys Pro Ser Leu Ser Ala Gln Pro Gly Pro Ala Val Ser Ser Gly Gly
        115                 120                 125 gac gta acc cta cag tgt cag act cgg tat ggc ttt gac caa ttt gct     432
Asp Val Thr Leu Gln Cys Gln Thr Arg Tyr Gly Phe Asp Gln Phe Ala
130                 135                 140 ctg tac aag gaa ggg gac cct gcg ccc tac aag aat ccc gag aga tgg     480
Leu Tyr Lys Glu Gly Asp Pro Ala Pro Tyr Lys Asn Pro Glu Arg Trp
145                 150                 155                 160 tac cgg gct agt ttc ccc atc atc acg gtg acc gcc gcc cac agc gga     528
Tyr Arg Ala Ser Phe Pro Ile Ile Thr Val Thr Ala Ala His Ser Gly
                165                 170                 175 acc tac cga tgc tac agc ttc tcc agc agg gac cca tac ctg tgg tcg     576
Thr Tyr Arg Cys Tyr Ser Phe Ser Ser Arg Asp Pro Tyr Leu Trp Ser
            180                 185                 190 gcc ccc agc gac ccc ctg gag ctt gtg gtc aca gga acc gac cct atc     624
Ala Pro Ser Asp Pro Leu Glu Leu Val Val Thr Gly Thr Asp Pro Ile
        195                 200                 205 ccc gag gag ccc aaa tct tgt gac aaa act cac aca tgc cca ccg tgc     672
Pro Glu Glu Pro Lys Ser Cys Asp Lys Thr His Thr Cys Pro Pro Cys
210                 215                 220 cca gca cct gaa ctc ctg ggg gga ccg tca gtc ttc ctc ttc ccc cca     720
Pro Ala Pro Glu Leu Leu Gly Gly Pro Ser Val Phe Leu Phe Pro Pro
225                 230                 235                 240 aaa ccc aag gac acc ctc atg atc tcc cgg acc cct gag gtc aca tgc     768
Lys Pro Lys Asp Thr Leu Met Ile Ser Arg Thr Pro Glu Val Thr Cys
                245                 250                 255 gtg gtg gtg gac gtg agc cac gaa gac cct gag gtc aag ttc aac tgg     816
Val Val Val Asp Val Ser His Glu Asp Pro Glu Val Lys Phe Asn Trp
            260                 265                 270 tac gtg gac ggc gtg gag gtg cat aat gcc aag aca aag ccg cgg gag     864
Tyr Val Asp Gly Val Glu Val His Asn Ala Lys Thr Lys Pro Arg Glu
        275                 280                 285
```

-continued

```
gag cag tac aac agc acg tac cgt gtg gtc agc gtc ctc acc gtc ctg      912
Glu Gln Tyr Asn Ser Thr Tyr Arg Val Val Ser Val Leu Thr Val Leu
    290                 295                 300 cac cag gac tgg ctg aat ggc aag gag tac aag tgc aag gtc tcc aac      960
His Gln Asp Trp Leu Asn Gly Lys Glu Tyr Lys Cys Lys Val Ser Asn
305                 310                 315                 320 aaa gcc ctc cca gcc ccc atc gag aaa acc atc tcc aaa gcc aaa ggg     1008
Lys Ala Leu Pro Ala Pro Ile Glu Lys Thr Ile Ser Lys Ala Lys Gly
                325                 330                 335 cag ccc cga gaa cca cag gtg tac acc ctg ccc cca tcc cgg gat gag     1056
Gln Pro Arg Glu Pro Gln Val Tyr Thr Leu Pro Pro Ser Arg Asp Glu
            340                 345                 350 ctg acc aag aac cag gtc agc ctg acc tgc ctg gtc aaa ggc ttc tat     1104
Leu Thr Lys Asn Gln Val Ser Leu Thr Cys Leu Val Lys Gly Phe Tyr
        355                 360                 365 ccc agc gac atc gcc gtg gag tgg gag ggc aat ggg cag ccg gag aac     1152
Pro Ser Asp Ile Ala Val Glu Trp Glu Gly Asn Gly Gln Pro Glu Asn
    370                 375                 380 aac tac aag acc acg cct ccc gtg ctg gac tcc gac ggc tcc ttc ttc     1200
Asn Tyr Lys Thr Thr Pro Pro Val Leu Asp Ser Asp Gly Ser Phe Phe
385                 390                 395                 400 ctc tac agc aag ctc acc gtg gac aag agc agg tgg cag cag ggg aac     1248
Leu Tyr Ser Lys Leu Thr Val Asp Lys Ser Arg Trp Gln Gln Gly Asn
                405                 410                 415 gtc ttc tca tgc tcc gtg atg cat gag gct ctg cac aac cac tac acg     1296
Val Phe Ser Cys Ser Val Met His Glu Ala Leu His Asn His Tyr Thr
            420                 425                 430 cag aag agc ctc tcc ctg tct ccg ggt aaa tga gcggccgc                1337
Gln Lys Ser Leu Ser Leu Ser Pro Gly Lys
        435                 440

<210> SEQ ID NO 2
<211> LENGTH: 442
<212> TYPE: PRT
<213> ORGANISM: Homo sapiens

<400> SEQUENCE: 2

Met Ser Pro Ser Pro Thr Ala Leu Phe Cys Leu Gly Leu Cys Leu Gly
1               5                   10                  15

Arg Val Pro Ala Gln Ser Gly Pro Leu Pro Lys Pro Ser Leu Gln Ala
            20                  25                  30

Leu Pro Ser Ser Leu Val Pro Leu Glu Lys Pro Val Thr Leu Arg Cys
        35                  40                  45

Gln Gly Pro Pro Gly Val Asp Leu Tyr Arg Leu Glu Lys Leu Ser Ser
    50                  55                  60

Ser Arg Tyr Gln Asp Gln Ala Val Leu Phe Ile Pro Ala Met Lys Arg
65                  70                  75                  80

Ser Leu Ala Gly Arg Tyr Arg Cys Ser Tyr Gln Asn Gly Ser Leu Trp
                85                  90                  95

Ser Leu Pro Ser Asp Gln Leu Glu Leu Val Ala Thr Gly Val Phe Ala
            100                 105                 110

Lys Pro Ser Leu Ser Ala Gln Pro Gly Pro Ala Val Ser Ser Gly Gly
        115                 120                 125

Asp Val Thr Leu Gln Cys Gln Thr Arg Tyr Gly Phe Asp Gln Phe Ala
    130                 135                 140

Leu Tyr Lys Glu Gly Asp Pro Ala Pro Tyr Lys Asn Pro Glu Arg Trp
145                 150                 155                 160

Tyr Arg Ala Ser Phe Pro Ile Ile Thr Val Thr Ala Ala His Ser Gly
```

|  |  |  | 165 |  |  |  | 170 |  |  |  | 175 |  |
| --- | --- | --- | --- | --- | --- | --- | --- | --- | --- | --- | --- | --- |

Thr Tyr Arg Cys Tyr Ser Phe Ser Ser Arg Asp Pro Tyr Leu Trp Ser
            180                 185                 190

Ala Pro Ser Asp Pro Leu Glu Leu Val Val Thr Gly Thr Asp Pro Ile
        195                 200                 205

Pro Glu Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Gly Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

```
<210> SEQ ID NO 3
<211> LENGTH: 679
<212> TYPE: DNA
<213> ORGANISM: Homo sapiens
<220> FEATURE:
<221> NAME/KEY: CDS
<222> LOCATION: (1)..(672)

<400> SEQUENCE: 3
``` atg tct cca tcc ccg acc gcc ctc ttc tgt ctt ggg ctg tgt ctg ggg    48
Met Ser Pro Ser Pro Thr Ala Leu Phe Cys Leu Gly Leu Cys Leu Gly
1               5                   10                  15 cgt gtg cca gcg cag agt gga ccg ctc ccc aag ccc tcc ctc cag gct    96
Arg Val Pro Ala Gln Ser Gly Pro Leu Pro Lys Pro Ser Leu Gln Ala
            20                  25                  30 ctg ccc agc tcc ctg gtg ccc ctg gag aag cca gtg acc ctc cgg tgc   144
Leu Pro Ser Ser Leu Val Pro Leu Glu Lys Pro Val Thr Leu Arg Cys
        35                  40                  45 cag gga cct ccg ggc gtg gac ctg tac cgc ctg gag aag ctg agt tcc   192
Gln Gly Pro Pro Gly Val Asp Leu Tyr Arg Leu Glu Lys Leu Ser Ser
    50                  55                  60

```
agc agg tac cag gat cag gca gtc ctc ttc atc ccg gcc atg aag aga    240
Ser Arg Tyr Gln Asp Gln Ala Val Leu Phe Ile Pro Ala Met Lys Arg
 65              70                  75                  80 agt ctg gct gga cgc tac cgc tgc tcc tac cag aac gga agc ctc tgg    288
Ser Leu Ala Gly Arg Tyr Arg Cys Ser Tyr Gln Asn Gly Ser Leu Trp
                 85                  90                  95 tcc ctg ccc agc gac cag ctg gag ctc gtt gcc acg gga gtt ttt gcc    336
Ser Leu Pro Ser Asp Gln Leu Glu Leu Val Ala Thr Gly Val Phe Ala
            100                 105                 110 aaa ccc tcg ctc tca gcc cag ccc ggc ccg gcg gtg tcg tca gga ggg    384
Lys Pro Ser Leu Ser Ala Gln Pro Gly Pro Ala Val Ser Ser Gly Gly
        115                 120                 125 gac gta acc cta cag tgt cag act cgg tat ggc ttt gac caa ttt gct    432
Asp Val Thr Leu Gln Cys Gln Thr Arg Tyr Gly Phe Asp Gln Phe Ala
130                 135                 140 ctg tac aag gaa ggg gac cct gcg ccc tac aag aat ccc gag aga tgg    480
Leu Tyr Lys Glu Gly Asp Pro Ala Pro Tyr Lys Asn Pro Glu Arg Trp
145                 150                 155                 160 tac cgg gct agt ttc ccc atc atc acg gtg acc gcc gcc cac agc gga    528
Tyr Arg Ala Ser Phe Pro Ile Ile Thr Val Thr Ala Ala His Ser Gly
                165                 170                 175 acc tac cga tgc tac agc ttc tcc agc agg gac cca tac ctg tgg tcg    576
Thr Tyr Arg Cys Tyr Ser Phe Ser Ser Arg Asp Pro Tyr Leu Trp Ser
            180                 185                 190 gcc ccc agc gac ccc ctg gag ctt gtg gtc aca gga acc gaa aat ctt    624
Ala Pro Ser Asp Pro Leu Glu Leu Val Val Thr Gly Thr Glu Asn Leu
        195                 200                 205 tat ttt caa ggt aag gat cat cat cat cat cat cat ggg gat tag        672
Tyr Phe Gln Gly Lys Asp His His His His His His Gly Asp
    210                 215                 220 cggccgc                                                            679

<210> SEQ ID NO 4
<211> LENGTH: 223
<212> TYPE: PRT
<213> ORGANISM: Homo sapiens

<400> SEQUENCE: 4

Met Ser Pro Ser Pro Thr Ala Leu Phe Cys Leu Gly Leu Cys Leu Gly
1               5                   10                  15

Arg Val Pro Ala Gln Ser Gly Pro Leu Pro Lys Pro Ser Leu Gln Ala
                20                  25                  30

Leu Pro Ser Ser Leu Val Pro Leu Glu Lys Pro Val Thr Leu Arg Cys
            35                  40                  45

Gln Gly Pro Pro Gly Val Asp Leu Tyr Arg Leu Glu Lys Leu Ser Ser
        50                  55                  60

Ser Arg Tyr Gln Asp Gln Ala Val Leu Phe Ile Pro Ala Met Lys Arg
65              70                  75                  80

Ser Leu Ala Gly Arg Tyr Arg Cys Ser Tyr Gln Asn Gly Ser Leu Trp
                85                  90                  95

Ser Leu Pro Ser Asp Gln Leu Glu Leu Val Ala Thr Gly Val Phe Ala
            100                 105                 110

Lys Pro Ser Leu Ser Ala Gln Pro Gly Pro Ala Val Ser Ser Gly Gly
        115                 120                 125

Asp Val Thr Leu Gln Cys Gln Thr Arg Tyr Gly Phe Asp Gln Phe Ala
130                 135                 140

Leu Tyr Lys Glu Gly Asp Pro Ala Pro Tyr Lys Asn Pro Glu Arg Trp
```

|     |     |     |     | 145 |     |     |     | 150 |     |     |     | 155 |     |     |     | 160 |
| --- | --- | --- | --- | --- | --- | --- | --- | --- | --- | --- | --- | --- | --- | --- | --- | --- |

Tyr Arg Ala Ser Phe Pro Ile Ile Thr Val Thr Ala Ala His Ser Gly
                    165                    170                    175

Thr Tyr Arg Cys Tyr Ser Phe Ser Ser Arg Asp Pro Tyr Leu Trp Ser
            180                    185                    190

Ala Pro Ser Asp Pro Leu Glu Leu Val Val Thr Gly Thr Glu Asn Leu
              195                    200                    205

Tyr Phe Gln Gly Lys Asp His His His His His His Gly Asp
    210                    215                    220

```
<210> SEQ ID NO 5
<211> LENGTH: 1374
<212> TYPE: DNA
<213> ORGANISM: Mus musculus
<220> FEATURE:
<221> NAME/KEY: CDS
<222> LOCATION: (1)..(1374)

<400> SEQUENCE: 5 atg gct gtc ctg gca tta ctc ttc tgc ctg gta aca ttc cca agc tgt        48
Met Ala Val Leu Ala Leu Leu Phe Cys Leu Val Thr Phe Pro Ser Cys
1               5                   10                  15 atc ctt tcc cag gtg cag ctg aag gag tca gga cct ggc ctg gtg gcg        96
Ile Leu Ser Gln Val Gln Leu Lys Glu Ser Gly Pro Gly Leu Val Ala
            20                  25                  30 ccc tca cag agc ctg tcc atc aca tgc acc gtc tca ggg ttc tca tta       144
Pro Ser Gln Ser Leu Ser Ile Thr Cys Thr Val Ser Gly Phe Ser Leu
        35                  40                  45 acc ggc tat ggt gta aac tgg gtt cgc cag cct cca gga aag ggt ctg       192
Thr Gly Tyr Gly Val Asn Trp Val Arg Gln Pro Pro Gly Lys Gly Leu
    50                  55                  60 gag tgg ctg gga atg ata tgg ggt gat gga agc aca gac tat aat tca       240
Glu Trp Leu Gly Met Ile Trp Gly Asp Gly Ser Thr Asp Tyr Asn Ser
65                  70                  75                  80 act ctc aaa tcc aga ctg agc atc agc aag gac aac tcc aag agc caa       288
Thr Leu Lys Ser Arg Leu Ser Ile Ser Lys Asp Asn Ser Lys Ser Gln
                85                  90                  95 gtt ttc tta aaa atg aac agt ctg caa act gat gac aca gcc agg tac       336
Val Phe Leu Lys Met Asn Ser Leu Gln Thr Asp Asp Thr Ala Arg Tyr
            100                 105                 110 tac tgt gcc aga gat ctt cct atg gac tac tgg ggt caa gga acc tca       384
Tyr Cys Ala Arg Asp Leu Pro Met Asp Tyr Trp Gly Gln Gly Thr Ser
        115                 120                 125 gtc acc gtc tcc tca gcc aaa acg aca ccc cca tct gtc tat cca ctg       432
Val Thr Val Ser Ser Ala Lys Thr Thr Pro Pro Ser Val Tyr Pro Leu
    130                 135                 140 gcc cct gga tct gct gcc caa act aac tcc atg gtg acc ctg gga tgc       480
Ala Pro Gly Ser Ala Ala Gln Thr Asn Ser Met Val Thr Leu Gly Cys
145                 150                 155                 160 ctg gtc aag ggc tat ttc cct gag cca gtg aca gtg acc tgg aac tct       528
Leu Val Lys Gly Tyr Phe Pro Glu Pro Val Thr Val Thr Trp Asn Ser
                165                 170                 175 gga tcc ctg tcc agc ggt gtg cac acc ttc cca gct gtc ctg cag tct       576
Gly Ser Leu Ser Ser Gly Val His Thr Phe Pro Ala Val Leu Gln Ser
            180                 185                 190 gac ctc tac act ctg agc agc tca gtg act gtc ccc tcc agc acc tgg       624
Asp Leu Tyr Thr Leu Ser Ser Ser Val Thr Val Pro Ser Ser Thr Trp
        195                 200                 205 ccc agc gag acc gtc acc tgc aac gtt gcc cac ccg gcc agc agc acc       672
Pro Ser Glu Thr Val Thr Cys Asn Val Ala His Pro Ala Ser Ser Thr
```

```
                      210                 215                 220
aag gtg gac aag aaa att gtg ccc agg gat tgt ggt tgt aag cct tgc      720
Lys Val Asp Lys Lys Ile Val Pro Arg Asp Cys Gly Cys Lys Pro Cys
225                 230                 235                 240 ata tgt aca gtc cca gaa gta tca tct gtc ttc atc ttc ccc cca aag      768
Ile Cys Thr Val Pro Glu Val Ser Ser Val Phe Ile Phe Pro Pro Lys
                245                 250                 255 ccc aag gat gtg ctc acc att act ctg act cct aag gtc acg tgt gtt      816
Pro Lys Asp Val Leu Thr Ile Thr Leu Thr Pro Lys Val Thr Cys Val
            260                 265                 270 gtg gta gac atc agc aag gat gat ccc gag gtc cag ttc agc tgg ttt      864
Val Val Asp Ile Ser Lys Asp Asp Pro Glu Val Gln Phe Ser Trp Phe
        275                 280                 285 gta gat gat gtg gag gtg cac aca gct cag acg caa ccc cgg gag gag      912
Val Asp Asp Val Glu Val His Thr Ala Gln Thr Gln Pro Arg Glu Glu
    290                 295                 300 cag ttc aac agc act ttc cgc tca gtc agt gaa ctt ccc atc atg cac      960
Gln Phe Asn Ser Thr Phe Arg Ser Val Ser Glu Leu Pro Ile Met His
305                 310                 315                 320 cag gac tgg ctc aat ggc aag gag ttc aaa tgc agg gtc aac agt gca     1008
Gln Asp Trp Leu Asn Gly Lys Glu Phe Lys Cys Arg Val Asn Ser Ala
                325                 330                 335 gct ttc cct gcc ccc atc gag aaa acc atc tcc aaa acc aaa ggc aga     1056
Ala Phe Pro Ala Pro Ile Glu Lys Thr Ile Ser Lys Thr Lys Gly Arg
            340                 345                 350 ccg aag gct cca cag gtg tac acc att cca cct ccc aag gag cag atg     1104
Pro Lys Ala Pro Gln Val Tyr Thr Ile Pro Pro Pro Lys Glu Gln Met
        355                 360                 365 gcc aag gat aaa gtc agt ctg acc tgc atg ata aca gac ttc ttc cct     1152
Ala Lys Asp Lys Val Ser Leu Thr Cys Met Ile Thr Asp Phe Phe Pro
    370                 375                 380 gaa gac att act gtg gag tgg cag tgg aat ggg cag cca gcg gag aac     1200
Glu Asp Ile Thr Val Glu Trp Gln Trp Asn Gly Gln Pro Ala Glu Asn
385                 390                 395                 400 tac aag aac act cag ccc atc atg gac aca gat ggc tct tac ttc gtc     1248
Tyr Lys Asn Thr Gln Pro Ile Met Asp Thr Asp Gly Ser Tyr Phe Val
                405                 410                 415 tac agc aag ctc aat gtg cag aag agc aac tgg gag gca gga aat act     1296
Tyr Ser Lys Leu Asn Val Gln Lys Ser Asn Trp Glu Ala Gly Asn Thr
            420                 425                 430 ttc acc tgc tct gtg tta cat gag ggc ctg cac aac cac cat act gag     1344
Phe Thr Cys Ser Val Leu His Glu Gly Leu His Asn His His Thr Glu
        435                 440                 445 aag agc ctc tcc cac tct cct ggt aag tga                             1374
Lys Ser Leu Ser His Ser Pro Gly Lys
    450                 455

<210> SEQ ID NO 6
<211> LENGTH: 457
<212> TYPE: PRT
<213> ORGANISM: Mus musculus

<400> SEQUENCE: 6

Met Ala Val Leu Ala Leu Leu Phe Cys Leu Val Thr Phe Pro Ser Cys
1               5                   10                  15

Ile Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45
```

-continued

```
Thr Gly Tyr Gly Val Asn Trp Val Arg Gln Pro Pro Gly Lys Gly Leu
    50                  55                  60
Glu Trp Leu Gly Met Ile Trp Gly Asp Gly Ser Thr Asp Tyr Asn Ser
65                  70                  75                  80
Thr Leu Lys Ser Arg Leu Ser Ile Ser Lys Asp Asn Ser Lys Ser Gln
                85                  90                  95
Val Phe Leu Lys Met Asn Ser Leu Gln Thr Asp Asp Thr Ala Arg Tyr
            100                 105                 110
Tyr Cys Ala Arg Asp Leu Pro Met Asp Tyr Trp Gly Gln Gly Thr Ser
            115                 120                 125
Val Thr Val Ser Ser Ala Lys Thr Thr Pro Pro Ser Val Tyr Pro Leu
130                 135                 140
Ala Pro Gly Ser Ala Ala Gln Thr Asn Ser Met Val Thr Leu Gly Cys
145                 150                 155                 160
Leu Val Lys Gly Tyr Phe Pro Glu Pro Val Thr Val Thr Trp Asn Ser
                165                 170                 175
Gly Ser Leu Ser Ser Gly Val His Thr Phe Pro Ala Val Leu Gln Ser
            180                 185                 190
Asp Leu Tyr Thr Leu Ser Ser Ser Val Thr Val Pro Ser Ser Thr Trp
            195                 200                 205
Pro Ser Glu Thr Val Thr Cys Asn Val Ala His Pro Ala Ser Ser Thr
210                 215                 220
Lys Val Asp Lys Lys Ile Val Pro Arg Asp Cys Gly Cys Lys Pro Cys
225                 230                 235                 240
Ile Cys Thr Val Pro Glu Val Ser Ser Val Phe Ile Phe Pro Pro Lys
                245                 250                 255
Pro Lys Asp Val Leu Thr Ile Thr Leu Thr Pro Lys Val Thr Cys Val
            260                 265                 270
Val Val Asp Ile Ser Lys Asp Asp Pro Glu Val Gln Phe Ser Trp Phe
            275                 280                 285
Val Asp Asp Val Glu Val His Thr Ala Gln Thr Gln Pro Arg Glu Glu
290                 295                 300
Gln Phe Asn Ser Thr Phe Arg Ser Val Ser Glu Leu Pro Ile Met His
305                 310                 315                 320
Gln Asp Trp Leu Asn Gly Lys Glu Phe Lys Cys Arg Val Asn Ser Ala
                325                 330                 335
Ala Phe Pro Ala Pro Ile Glu Lys Thr Ile Ser Lys Thr Lys Gly Arg
            340                 345                 350
Pro Lys Ala Pro Gln Val Tyr Thr Ile Pro Pro Pro Lys Glu Gln Met
            355                 360                 365
Ala Lys Asp Lys Val Ser Leu Thr Cys Met Ile Thr Asp Phe Phe Pro
370                 375                 380
Glu Asp Ile Thr Val Glu Trp Gln Trp Asn Gly Gln Pro Ala Glu Asn
385                 390                 395                 400
Tyr Lys Asn Thr Gln Pro Ile Met Asp Thr Asp Gly Ser Tyr Phe Val
                405                 410                 415
Tyr Ser Lys Leu Asn Val Gln Lys Ser Asn Trp Glu Ala Gly Asn Thr
            420                 425                 430
Phe Thr Cys Ser Val Leu His Glu Gly Leu His Asn His His Thr Glu
            435                 440                 445
Lys Ser Leu Ser His Ser Pro Gly Lys
450                 455
```

```
<210> SEQ ID NO 7
<211> LENGTH: 702
<212> TYPE: DNA
<213> ORGANISM: Mus musculus
<220> FEATURE:
<221> NAME/KEY: CDS
<222> LOCATION: (1)..(702)

<400> SEQUENCE: 7 atg aga ccg tct att cag ttc ctg ggg ctc ttg ttg ttc tgg ctt cat      48
Met Arg Pro Ser Ile Gln Phe Leu Gly Leu Leu Leu Phe Trp Leu His
1               5                   10                  15 ggt gct cag tgt gac atc cag atg aca cag tct cca tcc tca ctg tct      96
Gly Ala Gln Cys Asp Ile Gln Met Thr Gln Ser Pro Ser Ser Leu Ser
                20                  25                  30 gca tct ctg gga ggc aaa gtc acc atc act tgt aag gca agc caa gac     144
Ala Ser Leu Gly Gly Lys Val Thr Ile Thr Cys Lys Ala Ser Gln Asp
            35                  40                  45 att aac aag tat att gct tgg tac caa cac aag cct gga aaa ggt cct     192
Ile Asn Lys Tyr Ile Ala Trp Tyr Gln His Lys Pro Gly Lys Gly Pro
        50                  55                  60 agc ctg ctc ata cat tac aca tct act tta cag cca ggc atc cca tca     240
Ser Leu Leu Ile His Tyr Thr Ser Thr Leu Gln Pro Gly Ile Pro Ser
65                  70                  75                  80 agg ttc agt gga agt ggg tct ggg aga gat tat tcc ttc agc atc agc     288
Arg Phe Ser Gly Ser Gly Ser Gly Arg Asp Tyr Ser Phe Ser Ile Ser
                85                  90                  95 aac ctg gag cct gaa gat att gca act tat tat tgt cta cag tat gct     336
Asn Leu Glu Pro Glu Asp Ile Ala Thr Tyr Tyr Cys Leu Gln Tyr Ala
                100                 105                 110 aat ctt ctg acg ttc ggt gga ggc acc aag ctg gag atc aaa cgg gct     384
Asn Leu Leu Thr Phe Gly Gly Gly Thr Lys Leu Glu Ile Lys Arg Ala
            115                 120                 125 gat gct gca cca act gta tcc atc ttc cca cca tcc agt gag cag tta     432
Asp Ala Ala Pro Thr Val Ser Ile Phe Pro Pro Ser Ser Glu Gln Leu
        130                 135                 140 aca tct gga ggt gcc tca gtc gtg tgc ttc ttg aac aac ttc tac ccc     480
Thr Ser Gly Gly Ala Ser Val Val Cys Phe Leu Asn Asn Phe Tyr Pro
145                 150                 155                 160 aaa gac atc aat gtc aag tgg aag att gat ggc agt gaa cga caa aat     528
Lys Asp Ile Asn Val Lys Trp Lys Ile Asp Gly Ser Glu Arg Gln Asn
                165                 170                 175 ggc gtc ctg aac agt tgg act gat cag gac agc aaa gac agc acc tac     576
Gly Val Leu Asn Ser Trp Thr Asp Gln Asp Ser Lys Asp Ser Thr Tyr
                180                 185                 190 agc atg agc agc acc ctc acg ttg acc aag gac gag tat gaa cga cat     624
Ser Met Ser Ser Thr Leu Thr Leu Thr Lys Asp Glu Tyr Glu Arg His
            195                 200                 205 aac agc tat acc tgt gag gcc act cac aag aca tca act tca ccc att     672
Asn Ser Tyr Thr Cys Glu Ala Thr His Lys Thr Ser Thr Ser Pro Ile
        210                 215                 220 gtc aag agc ttc aac agg aat gag tgc tag                             702
Val Lys Ser Phe Asn Arg Asn Glu Cys
225                 230

<210> SEQ ID NO 8
<211> LENGTH: 233
<212> TYPE: PRT
<213> ORGANISM: Mus musculus

<400> SEQUENCE: 8

Met Arg Pro Ser Ile Gln Phe Leu Gly Leu Leu Leu Phe Trp Leu His
```

```
              1               5                  10                 15
          Gly Ala Gln Cys Asp Ile Gln Met Thr Gln Ser Pro Ser Ser Leu Ser
                         20                  25                 30

Ala Ser Leu Gly Gly Lys Val Thr Ile Thr Cys Lys Ala Ser Gln Asp
                         35                  40                 45

Ile Asn Lys Tyr Ile Ala Trp Tyr Gln His Lys Pro Gly Lys Gly Pro
                50                  55                  60

Ser Leu Leu Ile His Tyr Thr Ser Thr Leu Gln Pro Gly Ile Pro Ser
          65                  70                  75                 80

Arg Phe Ser Gly Ser Gly Ser Gly Arg Asp Tyr Ser Phe Ser Ile Ser
                         85                  90                 95

Asn Leu Glu Pro Glu Asp Ile Ala Thr Tyr Tyr Cys Leu Gln Tyr Ala
                        100                 105                110

Asn Leu Leu Thr Phe Gly Gly Gly Thr Lys Leu Glu Ile Lys Arg Ala
                        115                 120                125

Asp Ala Ala Pro Thr Val Ser Ile Phe Pro Pro Ser Ser Glu Gln Leu
          130                 135                 140

Thr Ser Gly Gly Ala Ser Val Val Cys Phe Leu Asn Asn Phe Tyr Pro
          145                 150                 155                160

Lys Asp Ile Asn Val Lys Trp Lys Ile Asp Gly Ser Glu Arg Gln Asn
                        165                 170                175

Gly Val Leu Asn Ser Trp Thr Asp Gln Asp Ser Lys Asp Ser Thr Tyr
                        180                 185                190

Ser Met Ser Ser Thr Leu Thr Leu Thr Lys Asp Glu Tyr Glu Arg His
                        195                 200                205

Asn Ser Tyr Thr Cys Glu Ala Thr His Lys Thr Ser Thr Ser Pro Ile
                        210                 215                 220

Val Lys Ser Phe Asn Arg Asn Glu Cys
          225                 230

<210> SEQ ID NO 9
<211> LENGTH: 226
<212> TYPE: PRT
<213> ORGANISM: Artificial
<220> FEATURE:
<223> OTHER INFORMATION: Mouse-human hybrid sequence

<400> SEQUENCE: 9

Gln Val Gln Leu Lys Glu Ser Gly Pro Gly Leu Val Ala Pro Ser Gln
          1               5                  10                 15

Ser Leu Ser Ile Thr Cys Thr Val Ser Gly Phe Ser Leu Thr Gly Tyr
                         20                  25                 30

Gly Val Asn Trp Val Arg Gln Pro Pro Gly Lys Gly Leu Glu Trp Leu
                         35                  40                 45

Gly Met Ile Trp Gly Asp Gly Ser Thr Asp Tyr Asn Ser Thr Leu Lys
                50                  55                  60

Ser Arg Leu Ser Ile Ser Lys Asp Asn Ser Lys Ser Gln Val Phe Leu
          65                  70                  75                 80

Lys Met Asn Ser Leu Gln Thr Asp Asp Thr Ala Arg Tyr Tyr Cys Ala
                         85                  90                 95

Arg Asp Leu Pro Met Asp Tyr Trp Gly Gln Gly Thr Ser Val Thr Val
                        100                 105                110

Ser Ser Ala Ser Thr Lys Gly Pro Ser Val Phe Pro Leu Ala Pro Ser
                        115                 120                125

Ser Lys Ser Thr Ser Gly Gly Thr Ala Ala Leu Gly Cys Leu Val Lys
```

```
                   130                 135                 140
Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Gln Thr Tyr Ile Cys Asn Val Asn His Lys Pro Ser Asn Thr Lys Val
                195                 200                 205

Asp Lys Lys Val Glu Pro Lys Ser Cys Ala Ala Ala His His His His
            210                 215                 220

His His
225

<210> SEQ ID NO 10
<211> LENGTH: 222
<212> TYPE: PRT
<213> ORGANISM: Artificial
<220> FEATURE:
<223> OTHER INFORMATION: Mouse-human hybrid sequence

<400> SEQUENCE: 10

Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
                20                  25                  30

Gly Val Asn Trp Val Arg Gln Pro Pro Ser Arg Gly Leu Glu Trp Leu
            35                  40                  45

Gly Met Ile Trp Gly Asp Gly Ser Thr Asp Tyr Gln Ser Thr Leu Lys
        50                  55                  60

Ser Arg Leu Ser Ile Ser Lys Asp Thr Ser Lys Ser Gln Val Phe Leu
65                  70                  75                  80

Lys Met Asn Ser Leu Thr Thr Asp Asp Thr Ala Arg Tyr Tyr Cys Ala
                85                  90                  95

Arg Asp Leu Pro Met Asp Tyr Trp Gly Gln Gly Thr Ser Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Gln Thr Tyr Ile Cys Asn Val Asn His Lys Pro Ser Asn Thr Lys Val
                195                 200                 205

Asp Lys Lys Val Glu Pro Lys Ser Cys Asp Lys Thr His Thr
            210                 215                 220

<210> SEQ ID NO 11
<211> LENGTH: 222
<212> TYPE: PRT
<213> ORGANISM: Artificial
<220> FEATURE:
<223> OTHER INFORMATION: Mouse-human hybrid sequence
```

<400> SEQUENCE: 11

```
Gln Val Gln Leu Gln Glu Ser Gly Pro Gly Leu Val Ala Pro Ser Gln
1               5                   10                  15
Ser Leu Ser Ile Thr Cys Thr Val Ser Gly Phe Ser Leu Thr Gly Tyr
            20                  25                  30
Gly Val Asn Trp Val Arg Gln Pro Pro Ser Arg Gly Leu Glu Trp Leu
        35                  40                  45
Gly Met Ile Trp Gly Asp Gly Ser Thr Asp Tyr Gln Ser Thr Leu Lys
    50                  55                  60
Ser Arg Leu Ser Ile Ser Lys Asp Asn Ser Lys Ser Gln Val Phe Leu
65                  70                  75                  80
Lys Met Asn Ser Leu Thr Thr Asp Asp Thr Ala Arg Tyr Tyr Cys Ala
                85                  90                  95
Arg Asp Leu Pro Met Asp Tyr Trp Gly Gln Gly Thr Ser Val Thr Val
            100                 105                 110
Ser Ser Ala Ser Thr Lys Gly Pro Ser Val Phe Pro Leu Ala Pro Ser
        115                 120                 125
Ser Lys Ser Thr Ser Gly Gly Thr Ala Ala Leu Gly Cys Leu Val Lys
    130                 135                 140
Asp Tyr Phe Pro Glu Pro Val Thr Val Ser Trp Asn Ser Gly Ala Leu
145                 150                 155                 160
Thr Ser Gly Val His Thr Phe Pro Ala Val Leu Gln Ser Ser Gly Leu
                165                 170                 175
Tyr Ser Leu Ser Ser Val Val Thr Val Pro Ser Ser Ser Leu Gly Thr
            180                 185                 190
Gln Thr Tyr Ile Cys Asn Val Asn His Lys Pro Ser Asn Thr Lys Val
        195                 200                 205
Asp Lys Lys Val Glu Pro Lys Ser Cys Asp Lys Thr His Thr
    210                 215                 220
```

<210> SEQ ID NO 12
<211> LENGTH: 222
<212> TYPE: PRT
<213> ORGANISM: Artificial
<220> FEATURE:
<223> OTHER INFORMATION: Mouse-human hybrid sequence

<400> SEQUENCE: 12

```
Glu Val Gln Leu Leu Glu Ser Gly Pro Gly Leu Val Ala Pro Ser Gly
1               5                   10                  15
Ser Leu Ser Ile Thr Cys Thr Val Ser Gly Phe Ser Leu Thr Gly Tyr
            20                  25                  30
Gly Val Asn Trp Val Arg Gln Pro Pro Gly Lys Gly Leu Glu Trp Leu
        35                  40                  45
Gly Met Ile Trp Gly Asp Gly Ser Thr Asp Tyr Gln Ser Thr Leu Lys
    50                  55                  60
Ser Arg Leu Ser Ile Ser Lys Asp Asn Ser Lys Ser Gln Val Phe Leu
65                  70                  75                  80
Lys Met Asn Ser Leu Arg Thr Asp Asp Thr Ala Arg Tyr Tyr Cys Ala
                85                  90                  95
Arg Asp Leu Pro Met Asp Tyr Trp Gly Leu Gly Thr Ser Val Thr Val
            100                 105                 110
Ser Ser Ala Ser Thr Lys Gly Pro Ser Val Phe Pro Leu Ala Pro Ser
        115                 120                 125
```

```
Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Leu Gly Thr
                180                 185                 190

Gln Thr Tyr Ile Cys Asn Val Asn His Lys Pro Ser Asn Thr Lys Val
                195                 200                 205

Asp Lys Lys Val Glu Pro Lys Ser Cys Asp Lys Thr His Thr
210                 215                 220
```

<210> SEQ ID NO 13
<211> LENGTH: 222
<212> TYPE: PRT
<213> ORGANISM: Artificial
<220> FEATURE:
<223> OTHER INFORMATION: Mouse-human hybrid sequence

<400> SEQUENCE: 13

```
Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Tyr Tyr
                20                  25                  30

Gly Val Asn Trp Val Arg Gln Pro Pro Ser Arg Gly Leu Glu Trp Leu
                35                  40                  45

Gly Met Ile Trp Gly Asp Gly Ser Thr Asp Tyr Gln Ser Thr Leu Lys
50                  55                  60

Ser Arg Leu Ser Ile Ser Lys Asp Asn Ser Lys Ser Gln Val Phe Leu
65                  70                  75                  80

Lys Met Asn Ser Leu Thr Thr Asp Asp Thr Ala Arg Tyr Tyr Cys Ala
                85                  90                  95

Arg Asp Leu Pro Met Asp Tyr Trp Gly Gln Gly Thr Ser Val Thr Val
                100                 105                 110

Ser Ser Ala Ser Thr Lys Gly Pro Ser Val Phe Pro Leu Ala Pro Ser
                115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Leu Gly Thr
                180                 185                 190

Gln Thr Tyr Ile Cys Asn Val Asn His Lys Pro Ser Asn Thr Lys Val
                195                 200                 205

Asp Lys Lys Val Glu Pro Lys Ser Cys Asp Lys Thr His Thr
210                 215                 220
```

<210> SEQ ID NO 14
<211> LENGTH: 222
<212> TYPE: PRT
<213> ORGANISM: Artificial
<220> FEATURE:
<223> OTHER INFORMATION: Mouse-human hybrid sequence

<400> SEQUENCE: 14

```
Gln Val Gln Leu Gln Glu Ser Gly Pro Gly Leu Val Ala Pro Ser Gln
  1               5                  10                  15

Ser Leu Ser Ile Thr Cys Thr Val Ser Gly Phe Ser Leu Thr Gly Tyr
             20                  25                  30

Gly Val Asn Trp Val Arg Gln Pro Pro Ser Arg Gly Leu Glu Trp Leu
             35                  40                  45

Gly Met Ile Trp Gly Asp Gly Ser Thr Asp Tyr Gln Ser Thr Leu Lys
 50                  55                  60

Ser Arg Leu Ser Ile Ser Lys Asp Asn Ser Lys Ser Gln Val Phe Leu
 65                  70                  75                  80

Lys Met Asn Ser Leu Thr Thr Asp Thr Ala Arg Tyr Tyr Cys Ala
                 85                  90                  95

Arg Asp Leu Pro Met Asp Glu Trp Gly Gln Gly Thr Ser Val Thr Val
                100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Leu Gly Thr
                180                 185                 190

Gln Thr Tyr Ile Cys Asn Val Asn His Lys Pro Ser Asn Thr Lys Val
            195                 200                 205

Asp Lys Lys Val Glu Pro Lys Ser Cys Asp Lys Thr His Thr
210                 215                 220

<210> SEQ ID NO 15
<211> LENGTH: 213
<212> TYPE: PRT
<213> ORGANISM: Artificial
<220> FEATURE:
<223> OTHER INFORMATION: Mouse-human hybrid sequence

<400> SEQUENCE: 15

Asp Ile Gln Met Thr Gln Ser Pro Ser Ser Leu Ser Ala Ser Val Gly
  1               5                  10                  15

Gly Arg Val Thr Ile Thr Cys Lys Ala Ser Gln Asp Ile Asn Lys Tyr
             20                  25                  30

Ile Ala Trp Tyr Gln His Lys Pro Gly Lys Gly Pro Ser Leu Leu Ile
             35                  40                  45

His Tyr Thr Ser Thr Leu Gln Pro Gly Val Pro Ser Arg Phe Ser Gly
 50                  55                  60

Ser Gly Ser Gly Arg Asp Tyr Ser Phe Ser Ile Ser Asn Leu Gln Pro
 65                  70                  75                  80

Glu Asp Ile Ala Thr Tyr Tyr Cys Leu Gln Tyr Ala Asn Leu Leu Thr
                 85                  90                  95

Phe Gly Gly Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140
```

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
                195                 200                 205

Asn Arg Gly Glu Cys
        210

<210> SEQ ID NO 16
<211> LENGTH: 213
<212> TYPE: PRT
<213> ORGANISM: Artificial
<220> FEATURE:
<223> OTHER INFORMATION: Mouse-human hybrid sequence

<400> SEQUENCE: 16

Asp Ile Gln Met Thr Gln Ser Pro Ser Ser Leu Ser Ala Ser Val Gly
1               5                   10                  15

Gly Arg Val Thr Ile Thr Cys Lys Ala Ser Gln Asp Ile Asn Lys Tyr
            20                  25                  30

Ile Ala Trp Tyr Gln His Lys Pro Gly Lys Pro Ser Leu Leu Ile
        35                  40                  45

His Tyr Thr Ser Thr Leu Gln Pro Gly Val Pro Ser Arg Phe Ser Gly
    50                  55                  60

Ser Gly Ser Gly Arg Asp Tyr Ser Phe Ser Ile Ser Asn Leu Gln Pro
65                  70                  75                  80

Glu Asp Ile Ala Thr Tyr Tyr Cys Leu Gln Tyr Ala His Leu Leu Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 17
<211> LENGTH: 213
<212> TYPE: PRT
<213> ORGANISM: Artificial
<220> FEATURE:
<223> OTHER INFORMATION: Mouse-human hybrid sequence

<400> SEQUENCE: 17

Asp Ile Gln Met Thr Gln Ser Pro Ser Ser Leu Ser Ala Ser Val Gly

```
                1               5                   10                  15
            Gly Arg Val Thr Ile Thr Cys Lys Ala Ser Gln Asp Ile Asn Lys Tyr
                            20                  25                  30
            Ile Ala Trp Tyr Gln His Lys Pro Gly Lys Gly Pro Ser Leu Leu Ile
                            35                  40                  45
            His Tyr Thr Ser Thr Leu Gln Pro Gly Val Pro Ser Arg Phe Ser Gly
                            50                  55                  60
            Ser Gly Ser Gly Arg Asp Tyr Ser Phe Ser Ile Ser Asn Leu Gln Pro
             65                  70                  75                  80
            Glu Asp Ile Ala Thr Tyr Tyr Cys Leu Gln Tyr Ala Leu Leu Leu Thr
                            85                  90                  95
            Phe Gly Gly Gly Thr Lys Leu Glu Ile Lys Arg Thr Val Ala Ala Pro
                            100                 105                 110
            Ser Val Phe Ile Phe Pro Pro Ser Asp Glu Gln Leu Lys Ser Gly Thr
                            115                 120                 125
            Ala Ser Val Val Cys Leu Leu Asn Asn Phe Tyr Pro Arg Glu Ala Lys
                            130                 135                 140
            Val Gln Trp Lys Val Asp Asn Ala Leu Gln Ser Gly Asn Ser Gln Glu
            145                 150                 155                 160
            Ser Val Thr Glu Gln Asp Ser Lys Asp Ser Thr Tyr Ser Leu Ser Ser
                            165                 170                 175
            Thr Leu Thr Leu Ser Lys Ala Asp Tyr Glu Lys His Lys Val Tyr Ala
                            180                 185                 190
            Cys Glu Val Thr His Gln Gly Leu Ser Ser Pro Val Thr Lys Ser Phe
                            195                 200                 205
            Asn Arg Gly Glu Cys
            210

<210> SEQ ID NO 18
<211> LENGTH: 10
<212> TYPE: PRT
<213> ORGANISM: Mus musculus

<400> SEQUENCE: 18

Gly Phe Ser Leu Thr Gly Tyr Gly Val Asn
 1               5                  10

<210> SEQ ID NO 19
<211> LENGTH: 16
<212> TYPE: PRT
<213> ORGANISM: Mus musculus

<400> SEQUENCE: 19

Met Ile Trp Gly Asp Gly Ser Thr Asp Tyr Gln Ser Thr Leu Lys Ser
 1               5                  10                  15

<210> SEQ ID NO 20
<211> LENGTH: 5
<212> TYPE: PRT
<213> ORGANISM: Mus musculus

<400> SEQUENCE: 20

Leu Pro Met Asp Tyr
 1               5

<210> SEQ ID NO 21
<211> LENGTH: 11
<212> TYPE: PRT
<213> ORGANISM: Mus musculus
```

```
<400> SEQUENCE: 21

Lys Ala Ser Gln Asp Ile Asn Lys Tyr Ile Ala
1               5                   10

<210> SEQ ID NO 22
<211> LENGTH: 7
<212> TYPE: PRT
<213> ORGANISM: Mus musculus

<400> SEQUENCE: 22

Thr Ser Thr Leu Gln Pro Gly
1               5

<210> SEQ ID NO 23
<211> LENGTH: 8
<212> TYPE: PRT
<213> ORGANISM: Mus musculus

<400> SEQUENCE: 23

Leu Gln Tyr Ala Asn Leu Leu Thr
1               5

<210> SEQ ID NO 24
<211> LENGTH: 23
<212> TYPE: DNA
<213> ORGANISM: Artificial
<220> FEATURE:
<223> OTHER INFORMATION: Primer 5'-GeneRacer

<400> SEQUENCE: 24
cgactggagc acgaggacac tga                                              23

<210> SEQ ID NO 25
<211> LENGTH: 21
<212> TYPE: DNA
<213> ORGANISM: Artificial
<220> FEATURE:
<223> OTHER INFORMATION: Primer RACEMOG1-3'

<400> SEQUENCE: 25
tatgcaaggc ttacaaccac a                                                21

<210> SEQ ID NO 26
<211> LENGTH: 24
<212> TYPE: DNA
<213> ORGANISM: Artificial
<220> FEATURE:
<223> OTHER INFORMATION: Primer CKFOR-3'

<400> SEQUENCE: 26
ctcattcctg ttgaagctct tgac                                             24

<210> SEQ ID NO 27
<211> LENGTH: 615
<212> TYPE: DNA
<213> ORGANISM: Macaca fascicularis
<220> FEATURE:
<221> NAME/KEY: CDS
<222> LOCATION: (1)..(615)

<400> SEQUENCE: 27 atg tct cca tcc ccg acc gcc ctc ttc tgt ctt ggg ctg tgt ctg ggg      48
Met Ser Pro Ser Pro Thr Ala Leu Phe Cys Leu Gly Leu Cys Leu Gly
1               5                   10                  15
```

-continued

| | |
|---|---|
| cgt gtg cca gcg cag agt gga ccg ctc ccc aag ccc tcc ctc cag gct<br>Arg Val Pro Ala Gln Ser Gly Pro Leu Pro Lys Pro Ser Leu Gln Ala<br>          20                    25                   30 | 96 |
| ctg ccc agc tcc ctg gtg ccc ctg gag aag cca gtg acc ctc cgg tgc<br>Leu Pro Ser Ser Leu Val Pro Leu Glu Lys Pro Val Thr Leu Arg Cys<br>          35                    40                   45 | 144 |
| cag gga cct ccg ggc gtg gac ctg tac cgc ctg gag aag ctg agt tcc<br>Gln Gly Pro Pro Gly Val Asp Leu Tyr Arg Leu Glu Lys Leu Ser Ser<br> 50                       55                   60 | 192 |
| agc agg tac cag gat cag gca gtc ctc ttc atc ccg gcc atg aag aga<br>Ser Arg Tyr Gln Asp Gln Ala Val Leu Phe Ile Pro Ala Met Lys Arg<br>65                    70                   75                   80 | 240 |
| agt ctg gct gga cgc tac cgc tgc tcc tac cag aac gga agc ctc tgg<br>Ser Leu Ala Gly Arg Tyr Arg Cys Ser Tyr Gln Asn Gly Ser Leu Trp<br>                    85                    90                   95 | 288 |
| tcc ccg ccc agc gac cag ctg gag ctc gtt gcc acg gga gtt ttt gcc<br>Ser Pro Pro Ser Asp Gln Leu Glu Leu Val Ala Thr Gly Val Phe Ala<br>                  100                  105                 110 | 336 |
| aaa ccc tcg ctc tca gcc cag ccc ggc ccg gcg gtg tcg tca gga ggg<br>Lys Pro Ser Leu Ser Ala Gln Pro Gly Pro Ala Val Ser Ser Gly Gly<br>          115                    120                  125 | 384 |
| gac gta acc cta cag tgt cag act cgg tat ggc ttt gac caa ttt gct<br>Asp Val Thr Leu Gln Cys Gln Thr Arg Tyr Gly Phe Asp Gln Phe Ala<br>130                    135                   140 | 432 |
| ctg tac aag gaa ggg gac cct gcg ccc tac aag aat ccc gag aga tgg<br>Leu Tyr Lys Glu Gly Asp Pro Ala Pro Tyr Lys Asn Pro Glu Arg Trp<br>145                    150                   155                 160 | 480 |
| tac cgg gct agt ttc ccc atc atc acg gtg acc gcc gcc cac agc gga<br>Tyr Arg Ala Ser Phe Pro Ile Ile Thr Val Thr Ala Ala His Ser Gly<br>                  165                  170                 175 | 528 |
| acc tac cga tgc tac agc ttc tcc agc ggg gac cca tac ctg tgg tca<br>Thr Tyr Arg Cys Tyr Ser Phe Ser Ser Gly Asp Pro Tyr Leu Trp Ser<br>          180                    185                  190 | 576 |
| gcc ccc agc gac ccc ctg gag ctt atg gtc aca gga acc<br>Ala Pro Ser Asp Pro Leu Glu Leu Met Val Thr Gly Thr<br>195                    200                   205 | 615 |

<210> SEQ ID NO 28
<211> LENGTH: 205
<212> TYPE: PRT
<213> ORGANISM: Macaca fascicularis

<400> SEQUENCE: 28

Met Ser Pro Ser Pro Thr Ala Leu Phe Cys Leu Gly Leu Cys Leu Gly
1               5                   10                  15

Arg Val Pro Ala Gln Ser Gly Pro Leu Pro Lys Pro Ser Leu Gln Ala
            20                  25                  30

Leu Pro Ser Ser Leu Val Pro Leu Glu Lys Pro Val Thr Leu Arg Cys
        35                  40                  45

Gln Gly Pro Pro Gly Val Asp Leu Tyr Arg Leu Glu Lys Leu Ser Ser
    50                  55                  60

Ser Arg Tyr Gln Asp Gln Ala Val Leu Phe Ile Pro Ala Met Lys Arg
65                  70                  75                  80

Ser Leu Ala Gly Arg Tyr Arg Cys Ser Tyr Gln Asn Gly Ser Leu Trp
                85                  90                  95

Ser Pro Pro Ser Asp Gln Leu Glu Leu Val Ala Thr Gly Val Phe Ala
            100                 105                 110

Lys Pro Ser Leu Ser Ala Gln Pro Gly Pro Ala Val Ser Ser Gly Gly
        115                 120                 125

```
Asp Val Thr Leu Gln Cys Gln Thr Arg Tyr Gly Phe Asp Gln Phe Ala
            130                 135                 140

Leu Tyr Lys Glu Gly Asp Pro Ala Pro Tyr Lys Asn Pro Glu Arg Trp
145                 150                 155                 160

Tyr Arg Ala Ser Phe Pro Ile Ile Thr Val Thr Ala Ala His Ser Gly
                165                 170                 175

Thr Tyr Arg Cys Tyr Ser Phe Ser Ser Gly Asp Pro Tyr Leu Trp Ser
            180                 185                 190

Ala Pro Ser Asp Pro Leu Glu Leu Met Val Thr Gly Thr
                195                 200                 205

<210> SEQ ID NO 29
<211> LENGTH: 228
<212> TYPE: PRT
<213> ORGANISM: Artificial
<220> FEATURE:
<223> OTHER INFORMATION: Mouse-human hybrid sequence

<400> SEQUENCE: 29

Glu Val Gln Leu Leu Glu Ser Gly Pro Gly Leu Val Ala Pro Ser Gly
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Gln Ser Thr Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Arg Thr Asp Thr Ala Arg Tyr Tyr Cys Ala
                85                  90                  95

Arg Asp Leu Pro Met Asp Tyr Trp Gly Leu Gly Thr Ser Val Thr Val
                100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr His His
    210                 215                 220

His His His His
225

<210> SEQ ID NO 30
<211> LENGTH: 227
<212> TYPE: PRT
<213> ORGANISM: Artificial
<220> FEATURE:
<223> OTHER INFORMATION: Mouse-human hybrid sequence
```

```
<400> SEQUENCE: 30

Glu Val Gln Leu Leu Glu Ser Gly Pro Gly Leu Val Ala Pro Ser Gly
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Gln Ser Thr Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Arg Thr Asp Asp Thr Ala Arg Tyr Tyr Cys Ala
                85                  90                  95

Arg Asp Leu Pro Met Asp Tyr Trp Gly Leu Gly Thr Ser Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Gly Gly
    210                 215                 220

Gly Gly Ser
225

<210> SEQ ID NO 31
<211> LENGTH: 232
<212> TYPE: PRT
<213> ORGANISM: Artificial
<220> FEATURE:
<223> OTHER INFORMATION: Mouse-human hybrid sequence

<400> SEQUENCE: 31

Glu Val Gln Leu Leu Glu Ser Gly Pro Gly Leu Val Ala Pro Ser Gly
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Gln Ser Thr Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Arg Thr Asp Asp Thr Ala Arg Tyr Tyr Cys Ala
                85                  90                  95

Arg Asp Leu Pro Met Asp Tyr Trp Gly Leu Gly Thr Ser Val Thr Val
            100                 105                 110
```

```
Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Gly Gly
210                 215                 220

Gly Gly Ser Gly Gly Gly Ser
225                 230
```

<210> SEQ ID NO 32
<211> LENGTH: 319
<212> TYPE: PRT
<213> ORGANISM: Homo sapiens

<400> SEQUENCE: 32

```
Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
            20                  25                  30

Gly Val Asp Leu Tyr Arg Leu Glu Lys Leu Ser Ser Ser Arg Tyr Gln
        35                  40                  45

Asp Gln Ala Val Leu Phe Ile Pro Ala Met Lys Arg Ser Leu Ala Gly
    50                  55                  60

Arg Tyr Arg Cys Ser Tyr Gln Asn Gly Ser Leu Trp Ser Leu Pro Ser
65                  70                  75                  80

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
            100                 105                 110

Gln Cys Gln Thr Arg Tyr Gly Phe Asp Gln Phe Ala Leu Tyr Lys Glu
        115                 120                 125

Gly Asp Pro Ala Pro Tyr Lys Asn Pro Glu Arg Trp Tyr Arg Ala Ser
    130                 135                 140

Phe Pro Ile Ile Thr Val Thr Ala Ala His Ser Gly Thr Tyr Arg Cys
145                 150                 155                 160

Tyr Ser Phe Ser Ser Arg Asp Pro Tyr Leu Trp Ser Ala Pro Ser Asp
                165                 170                 175

Pro Leu Glu Leu Val Val Thr Gly Thr Ser Val Thr Pro Ser Arg Leu
            180                 185                 190

Pro Thr Glu Pro Pro Ser Ser Val Ala Glu Phe Ser Glu Ala Thr Ala
        195                 200                 205

Glu Leu Thr Val Ser Phe Thr Asn Lys Val Phe Thr Thr Glu Thr Ser
    210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys Gly Asn Leu Val Arg Ile Cys Leu Gly
                245                 250                 255
```

Ala Val Ile Leu Ile Ile Leu Ala Gly Phe Leu Ala Glu Asp Trp His
            260                 265                 270

Ser Arg Arg Lys Arg Leu Arg His Arg Gly Arg Ala Val Gln Arg Pro
        275                 280                 285

Leu Pro Pro Leu Pro Pro Leu Pro Gln Thr Arg Lys Ser His Gly Gly
    290                 295                 300

Gln Asp Gly Gly Arg Gln Asp Val His Ser Arg Gly Leu Cys Ser
305                 310                 315

<210> SEQ ID NO 33
<211> LENGTH: 226
<212> TYPE: PRT
<213> ORGANISM: Mus musculus

<400> SEQUENCE: 33

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Gln Ser Thr Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Asp Leu Pro Met Asp Tyr Trp Gly Gln Gly Thr Ser Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Ala Ala Ala His His His
    210                 215                 220

His His
225

<210> SEQ ID NO 34
<211> LENGTH: 213
<212> TYPE: PRT
<213> ORGANISM: Mus musculus

<400> SEQUENCE: 34

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Ser Leu Leu Ile
             35                  40                  45

His Tyr Thr Ser Thr Leu Gln Pro Gly Ile Pro Ser Arg Phe Ser Gly
 50                  55                  60

Ser Gly Ser Gly Arg Asp Tyr Ser Phe Ser Ile Ser Asn Leu Glu Pro
 65                  70                  75                  80

Glu Asp Ile Ala Thr Tyr Tyr Cys Leu Gln Tyr Ala Asn Leu Leu Thr
                 85                  90                  95

Phe Gly Gly Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
    210

<210> SEQ ID NO 35
<211> LENGTH: 5
<212> TYPE: PRT
<213> ORGANISM: Artificial
<220> FEATURE:
<223> OTHER INFORMATION: Mouse-human hybrid sequence

<400> SEQUENCE: 35

His His His His His
1               5

<210> SEQ ID NO 36
<211> LENGTH: 5
<212> TYPE: PRT
<213> ORGANISM: Artificial
<220> FEATURE:
<223> OTHER INFORMATION: Mouse-human hybrid sequence

<400> SEQUENCE: 36

Gly Gly Gly Gly Ser
1               5

<210> SEQ ID NO 37
<211> LENGTH: 10
<212> TYPE: PRT
<213> ORGANISM: Artificial
<220> FEATURE:
<223> OTHER INFORMATION: Mouse-human hybrid sequence

<400> SEQUENCE: 37

Gly Gly Gly Gly Ser Gly Gly Gly Gly Ser
1               5                   10

-continued

```
<210> SEQ ID NO 38
<211> LENGTH: 6
<212> TYPE: PRT
<213> ORGANISM: Mus musculus

<400> SEQUENCE: 38

Asp Leu Pro Met Asp Tyr
1               5

<210> SEQ ID NO 39
<211> LENGTH: 8
<212> TYPE: PRT
<213> ORGANISM: Mus musculus

<400> SEQUENCE: 39

Tyr Thr Ser Thr Leu Gln Pro Gly
1               5
```